(12) United States Patent
Ehlis et al.

(10) Patent No.: US 7,311,897 B2
(45) Date of Patent: Dec. 25, 2007

(54) SYMMETRICAL TRIAZINE DERIVATIVES

(75) Inventors: Thomas Ehlis, Freiburg (DE); Stefan Müller, Rheinfelden (DE); Pascal Hayoz, Hofstetten (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 815 days.

(21) Appl. No.: 10/804,676

(22) Filed: Mar. 19, 2004

(65) Prior Publication Data

US 2004/0191191 A1    Sep. 30, 2004

(30) Foreign Application Priority Data

Mar. 20, 2003  (EP)  ................... 03100758
Jul. 29, 2003   (EP)  ................... 03102325

(51) Int. Cl.
  A61Q 17/04    (2006.01)
  A61Q 19/00    (2006.01)
  A61K 8/00     (2006.01)

(52) U.S. Cl. ................ 424/59; 424/60; 424/400; 424/401

(58) Field of Classification Search .......... 424/59, 424/60, 400, 401
See application file for complete search history.

(56) References Cited

U.S. PATENT DOCUMENTS

| 6,225,467 B1 | 5/2001 | Esteghamatian et al. .... 544/180 |
| 6,242,598 B1 | 6/2001 | Stevenson et al. ......... 544/216 |
| 2002/0155073 A1 | 10/2002 | Fankhauser et al. ....... 424/59 |

FOREIGN PATENT DOCUMENTS

| EP | 0941989 | 9/1999 |
| GB | 1061521 | 3/1967 |
| WO | 98/22447 | 5/1998 |
| WO | 00/78277 | 12/2000 |

*Primary Examiner*—Shelly A. Dodson
(74) *Attorney, Agent, or Firm*—Kevin T. Mensfield

(57) ABSTRACT

Disclosed is the use of the compounds of formula

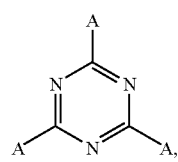

(1)

wherein

A is a radical of formula

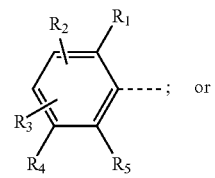

(1a)

or

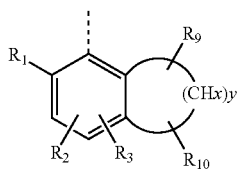

(1b)

$R_1$ and $R_5$ independently from each other are hydrogen; $C_1$-$C_{18}$alkyl; or $C_6$-$C_{12}$aryl;

$R_2$, $R_3$ and $R_4$ independently from each other are hydrogen; or a radical of formula

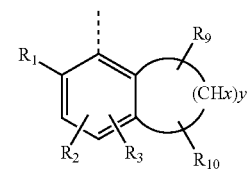

(1c)

wherein, in formula (1a), at least one of the radicals $R_2$, $R_3$ and $R_4$ are a radical of formula (1c);

$R_6$, $R_7$, $R_8$, $R_9$ and $R_{10}$ independently from each other are hydrogen; hydroxy; halogen; $C_1$-$C_{18}$alkyl; $C_1$-$C_{18}$alkoxy; $C_6$-$C_{12}$aryl; biphenylyl; $C_6$-$C_{12}$aryloxy; $C_1$-$C_{18}$alkylthio; carboxy; —COOM; $C_1$-$C_{18}$-alkylcarboxyl; aminocarbonyl; or mono- or di-$C_1$-$C_{18}$alkylamino; $C_1$-$C_{10}$acylamino; —COOH;

M is an alkali metal ion;

x is 1 or 2; and y is a number from 2 to 10;

for the protection of human and animal hair and skin against the damaging effect of UV radiation.

The compounds of formula (1) are high effective UV absorbers for cosmetic formulations aund can be—depending on their physical properties be used in micronized or soluble form.

37 Claims, No Drawings

SYMMETRICAL TRIAZINE DERIVATIVES

The present invention relates to the use of specific symmetrical triazine derivatives for the protection of human and animal hair and skin against the damaging effect of UV radiation, cosmetic compositions comprising these triazine derivatives and process for preparation of these compounds.

Triazines which are symmetrically substituted by biphenyl or naphthyl are known, for example from U.S. Pat. No. 6,225,467. They are used as for electroluminescent devices.

Surprisingly it has been found that these compounds can be used as highly effective UV absorbers for cosmetic applications.

Therefore, the present invention refers to the non-therapeutic use of the compounds of formula (1)

wherein
A is a radical of formula (1a)

; or (1b)

$R_1$ and $R_5$ independently from each other are hydrogen; $C_1$-$C_{18}$alkyl; or $C_6$-$C_{12}$aryl;
$R_2$, $R_3$ and $R_4$ independently from each other are hydrogen; or a radical of formula (1c)

wherein at least one of the radicals $R_2$, $R_3$ and $R_4$ are a radical of formula (1c);
$R_6$, $R_7$, $R_8$, $R_9$ and $R_{10}$ independently from each other are hydrogen; hydroxy; halogen; $C_1$-$C_{18}$alkyl; $C_1$-$C_{18}$alkoxy; $C_6$-$C_{12}$aryl; biphenylyl; $C_6$-$C_{12}$aryloxy; $C_1$-$C_{18}$alkylthio; carboxy —COOM; $C_1$-$C_{18}$-alkylcarboxyl; aminocarbonyl; or mono- or di-$C_1$-$C_{18}$alkylamino; $C_1$-$C_{10}$acylamino; —COOH;

M is an alkali metal ion;
x is 1 or 2; and
y is a number from 2 to 10;
for the protection of human and animal hair and skin against the damaging effect of UV radiation.

$C_1$-$C_{18}$alkyl according to the definition for the radicals of the compound of formula (1) are straight-chain or branched alkyl radicals like methyl, ethyl, n-propyl, isopropyl, n-butyl, sec.butyl, tert.butyl, amyl, isoamyl or tert.amyl, hexyl, 2-ethylhexyl, heptyl, octyl, isooctyl, nonyl, decyl, undecyl, dodecyl, tetradecyl, pentadecyl, hexadecyl, heptadecyl or octadecyl $C_1$-$C_{18}$alkyl according to the definition for the radicals of the compound of formula (1) may be substituted by methoxyethyl, ethoxypropyl, 2-ethylhexyl, hydroxyethyl, chloropropyl, N,N-diethylaminopropyl, cyanoethyl, phenethyl, benzyl, p-tert-butylphenethyl, p-tert-octylphenoxyethyl, 3-(2,4-di-tert-amylphenoxy)-propyl, ethoxycarbonylmethyl-2-(2-hydroxyethoxy)ethyl, or 2-furylethyl.

$C_1$-$C_{18}$alkyl according to the definition for the radicals of the compound of formula (1) are for example methoxy, ethoxy, n-propoxy, isopropoxy, n-butoxy, sec.butoxy, tert.butoxy, amyloxy, isoamyloxy or tert.amyloxy, hexyloxy, heptyloxy, octyloxy, isooctyloxy, nonyloxy, decyloxy, undecyloxy, dodecyloxy, tetradecyloxy, pentadecyloxy, hexadecyloxy, heptadecyloxy or octadecyloxy.

$C_6$-$C_{10}$aryl according to the definition for the radicals of the compound of formula (1) is for example naphthyl und preferably phenyl.

Preferably compounds of formula (2)

are used, wherein
$R_1$, $R_5$, $R_6$, $R_7$ und $R_8$ are defined as in formula (1).
In formula (2) $R_1$ and $R_5$ are preferably hydrogen.
Most preferably compounds of formula (1) or (2) are used wherein $R_6$ and $R_8$ are hydrogen.
Compounds of formula (1) of preferred interest are those, wherein
$R_7$ is hydrogen; hydroxy; $C_1$-$C_5$alkyl; $C_1$-$C_5$alkoxy; —COOM; —COOH; or $COOR_{10}$;
M is an alkali metal ion; and
$R_{10}$ is $C_1$-$C_5$alkyl.

Furthermore compounds of formula
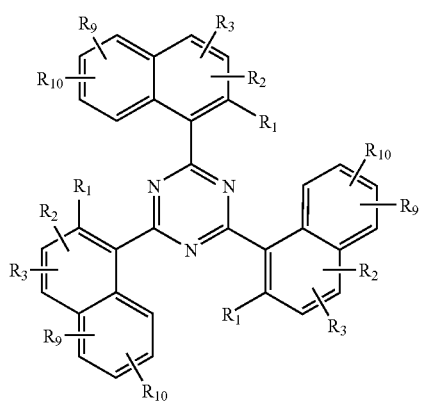
(3)
are preferably used, wherein
$R_1$, $R_2$, $R_3$, $R_9$ and $R_{10}$ are defined as in formula (1).
Preferably compounds of formula (3) are used, wherein
$R_1$, $R_2$, $R_3$, $R_9$ and $R_{10}$ are hydrogen; or, independently from each other, $C_1$-$C_{18}$alkyl.
Examples of triazine derivatives, which are preferably used in the present invention are the compounds of formula
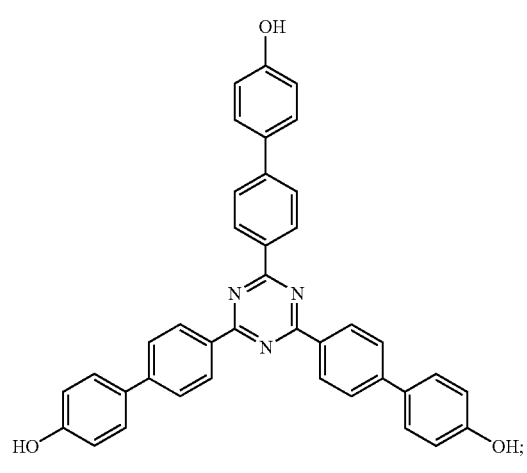
(4)
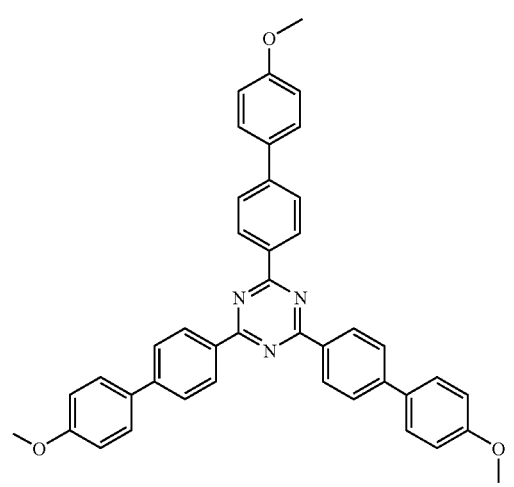
(5)
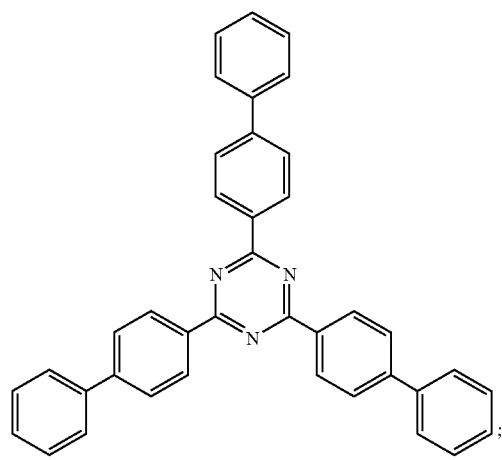
(6)
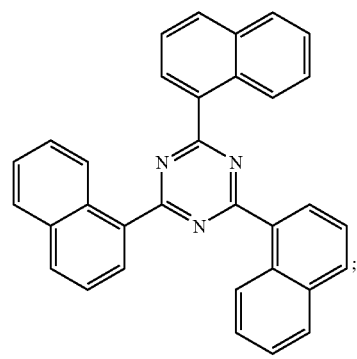
(7)

-continued

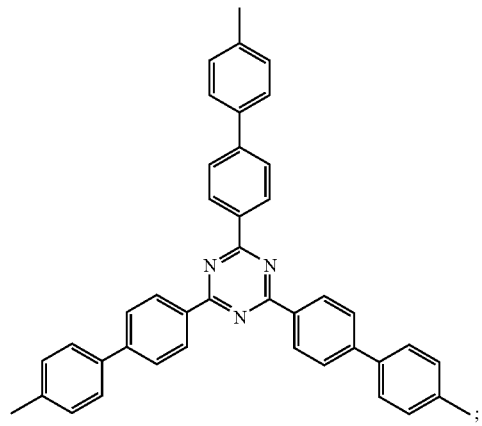
(8)

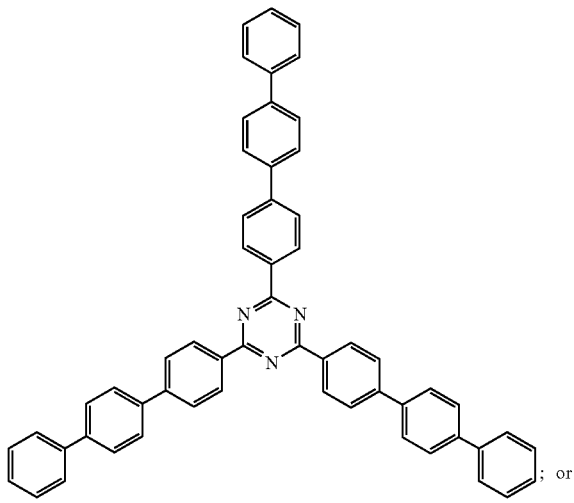
(9) ; or

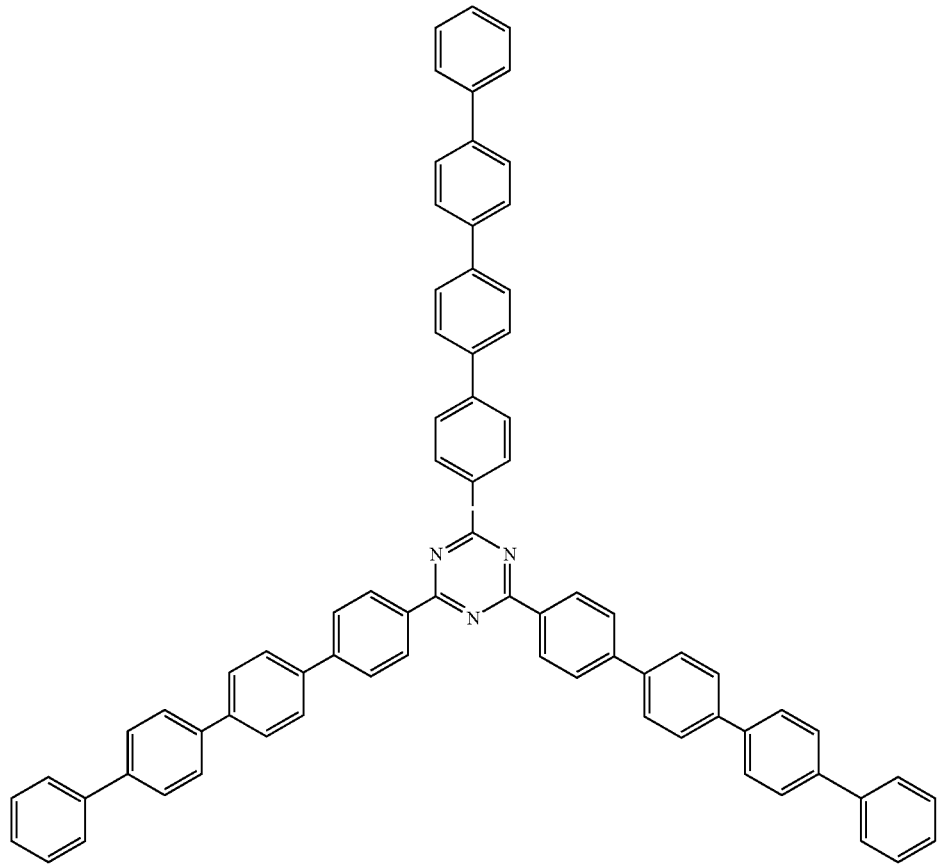
(10)

The compounds of the formula (1) according to the present invention are particularly suitable as UV filters, i.e. for protecting ultraviolet-sensitive organic materials, in particular the skin and hair of humans and animals, from the harmful effects of UV radiation. These compounds are therefore suitable as sunscreens in cosmetic, pharmaceutical and veterinary medical preparations. These compounds can be used both in dissolved form and in the micronized state.

The UV absorbers according to the present invention—depending on the substituents of the triazine aryl groups $R_1$, $R_2$ $R_5$, $R_6$, $R_7$, $R_8$, $R_9$ and $R_{10}$ in formulae (1a), (1b) or (1c)—can be used either in the dissolved state (soluble organic filters, solubelized organic filters) or in the micronised state (nanoscalar organic filters, particulate organic filters, UV-absorber pigments).

The triazine derivatives of formula (1) which have no alkyl substituents or only lower-alkyl substituents are characterized by a poor oil-solubility and a high melting point. They are therefore suitable in particular as UV absorbers in the micronized state.

Any known process suitable for the preparation of microparticles can be used for the preparation of the micronised UV absorbers, for example:

wet-milling (low viscous micronisation process for pumpable dispersions), with a hard grinding medium, for example zirconium silicate balls in a ball mill and a protective surfactant or a protective polymer in water or in a suitable organic solvent;

wet-kneading (high viscous micronisation process non pump-able pastes) using a continuous or discontinuous (batch) kneader. For a wet-kneading process a solvent (water or cosmetically acceptable oils), a grinding-aid (surfactant, emulsifier) and a polymeric grinding aid may be used.

Both processes may be used respectively spray-drying from a suitable solvent, for example aqueous suspensions or suspensions containing organic solvents, or true solutions in water, ethanol, dichloroethane, toluene or N-methylpyrrolidone etc.

by the expansion according to the RESS process (Rapid Expansion of Supercritical Solutions) of supercritical fluids (e.g. $CO_2$) in which the UV filter or filters is/are dissolved, or the expansion of fluid carbon dioxide together with a solution of one or more UV filters in a suitable organic solvent;

by reprecipitation from suitable solvents, including supercritical fluids (GASR process=Gas Anti-Solvent Recrystallisation/PCA process=Precipitation with Compressed Anti-solvents).

As milling apparatus for the preparation of the micronised organic UV absorbers there may be used, for example, a jet mill, ball mill, vibratory mill or hammer mill, preferably a high-speed mixing mill. Even more preferablyused are modern ball mills; manufactures of these mill-types are for example Netzsch (LMZ-mill), Drais (DCP-viscoflow or cosmo), Bühler AG (centrifugal mills) or Bachhofer. The grinding is preferably carried out with a grinding aid. As kneading apparatus for the preparation of the micronised organic UV absorbers examples are typically sigma-hook batch kneaders but also serial batch kneaders (IKA-Werke) or continuous kneaders (Contiuna from Werner und Pfleiderer).

Useful low molecular weight grinding aids for all the above micronizing processes are surfactants and emulsifies as disclosed below in the chapters "emulsifiers" and "surfactants" and "fatty alcohols".

Useful polymeric grinding aids for water dispersion are cosmetically acceptable water soluble polymers with Mn>500 g/mol for example acrylates (Salcare types), modified or non-modified polysaccharides, polyglucosides or xanthan gum. Furthermore an alkylated vinylpyrrolidone polymer, a vinylpyrrolidone/vinyl acetate copolymer, an acyl glutamate, an alkyl polyglucoside, ceteareth-25 or a phospholipid may be used. Oil dispersions may contain cosmetically acceptable waxy polymers or natural waxes as polymeric grinding aid in order to adjust viscosity during and after processing. Examples of other useful polymeric grinding aids are dieclosed below in the chapter "polymers".

Useful solvents for the grinding process are water, brine, (poly-)ethylenglycol, glycerine or cosmetically acceptable oils. Other useful sovents are disclosed below in the chapters "esters of fatty acids", "natural and synthetic triglycerides including glyceryl esters and derivatives", "perlescent waxes", "hydrocarbon oils" and "silicones or siloxanes".

The micronised UV absorbers so obtained usually have an average particle size from 0.02 to 2, preferably from 0.03 to 1.5, and more especially from 0.05 to 1.0 micrometer.

The UV absorbers according to the present invention can also be used as dry substrates in powder form. For that purpose the UV absorbers are subjected to known grinding methods, such as vacuum atomization, countercurrent spray-drying etc. Such powders have a particle size from 0.1 micrometer to 2 micrometer. In order to avoid the occurrence of agglomeration, the UV absorbers may be coated with a surface-active compound prior to the pulverization process, for example with an anionic, non-ionic or amphoteric surfactant, e.g. a phospholipid or a known polymer, such as PVP, an acrylate etc.

The UV absorbers according to the present invention can also be used in specific carriers for cosmetics, for example in solid lipid nanoparticles (SLN) or in inert sol-gel microcapsules wherein the UV absorbers are encapsulated (Pharmazie, 2001 (6), p. 783-786). Lipid nanoparticles (CLN,= Crystalline Lipid Nanoparticles) as described in Internat. J. Pharmaceutics, 2002, 242, P. 373-375 can be used as active carrier for UV filter according to the invention (for example the compound of formula 6).

The cosmetic formulations or pharmaceutical compositions according to the present invention may additionally contain one or more than one further UV filter as listed in tables 1-3.

The cosmetic or pharmaceutical preparations can be prepared by physically mixing the UV absorber(s) with the adjuvant using customary methods, for example by simply stirring together the individual components, especially by making use of the dissolution properties of already known cosmetic UV absorbers, like octyl methoxy cinnamate, salicylic acid isooctyl ester, etc. The UV absorber can be used, for example, without further treatment, or in the micronised state, or in the form of a powder.

Cosmetic or pharmaceutical preparations contain from 0.05-40% by weight, based on the total weight of the composition, of one UV absorber or UV absorber mixtures.

Preference is given to the use of mixing ratios of the UV absorber of formula (1) according to the present invention and optionally further light-protective agents (as described in table 1-3) from 1:99 to 99:1, preferably from 1:95 to 95:1 and most preferably from 10:90 to 90:10, based on weight. Of special interest are mixing ratios of from 20:80 to 80:20, preferably from 40:60 to 60:40 and most preferably approximately 50:50. Such mixtures can be used, inter alia, to improve the solubility or to increase UV absorption.

The UV absorbers of formula (1) according to the present invention or combinations of UV filters are useful to protect skin, hair and/or natural or artificial hair color.

TABLE 1

Suitable UV filter substances which can be additionally used with
the UV absorbers according to the present invention p-aminobenzoic acid derivatives, for example 4-dimethylaminobenzoic acid 2-ethylhexyl ester;
salicylic acid derivatives, for example salicylic acid 2-ethylhexyl ester;
benzophenone derivatives, for example 2-hydroxy-4-methoxybenzophenone and its 5-sulfonic acid derivative;
dibenzoylmethane derivatives, for example 1-(4-tert-butylphenyl)-3-(4-methoxyphenyl)-propane-1,3-dione;
diphenylacrylates, for example 2-ethylhexyl 2-cyano-3,3-diphenylacrylate, and 3-(benzo-furanyl) 2-cyanoacrylate;
3-imidazol-4-ylacrylic acid and esters;
benzofuran derivatives, especially 2-(p-aminophenyl)benzofuran derivatives, described in
EP-A-582 189, U.S. Pat. No. 5,338,539, U.S. Pat. No. 5,518,713 and EP-A-613 893;
polymeric UV absorbers, for example the benzylidene malonate derivatives described in EP-A-709 080;
cinnamic acid derivatives, for example the 4-methoxycinnamic acid 2-ethylhexyl ester and
isoamyl ester or cinnamic acid derivatives described in U.S. Pat. No. 5,601,811 and WO 97/00851;
camphor derivatives, for example 3-(4'-methyl)benzylidene-bornan-2-one, 3-benzylidene-bornan-2-one,
N-[2(and 4)-2-oxyborn-3-ylidene-methyl)-benzyl]acrylamide polymer, 3-(4'-trimethylammonium)-benzylidene-
bornan-2-one methyl sulfate, 3,3'-(1,4-phenylenedimethine)-bis(7,7-dimethyl-2-oxo-bicyclo[2.2.1]heptane-1-
methanesulfonic acid) and salts, 3-(4'-sulfo)benzylidene-bornan-2-one and salts; camphorbenzalkonium methosulfate;
hydroxyphenyltriazine compounds, for example 2-(4'-methoxyphenyl)-4,6-bis(2'-hydroxy-4'-n-octyloxyphenyl)-
1,3,5-triazine; 2,4-bis{[4-(3-(2-propyloxy)-2-hydroxy-propyloxy)-2-hydroxy]-phenyl}-6-(4-methoxyphenyl)-1,3,5-
triazine; 2,4-bis{[4-(2-ethyl-hexyloxy)-2-hydroxy]-phenyl}-6-[4-(2-methoxyethyl-carboxyl)-phenylamino]-1,3,5-
triazine; 2,4-bis{[4-(tris(trimethylsilyloxy-silylpropyloxy)-2-hydroxy]-phenyl}-6-(4-methoxyphenyl)-1,3,5-
triazine; 2,4-bis{[4-(2''-methylpropenyloxy)-2-hydroxy]-phenyl}-6-(4-methoxyphenyl)-1,3,5-
triazine; 2,4-bis{[4-(1',1',1',3',5',5',5'-heptamethyltrisilyl-2'''-methyl-propyloxy)-2-hydroxy]-
phenyl}-6-(4-methoxyphenyl)-1,3,5-triazine; 2,4-bis{[4-(3-(2-propyloxy)-2-hydroxy-propyloxy)-
2-hydroxy]-phenyl}-6-[4-ethylcarboxy)-phenylamino]-1,3,5-triazine;
benzotriazole compounds, for example 2,2'-methylene-bis(6-(2H-benzotriazol-2-yl)-4-(1,1,3,3-tetramethylbutyl)-phenol;
trianilino-s-triazine derivatives, for example 2,4,6-trianiline-(p-carbo-2'-ethyl-1'-oxy)-1,3,5-triazine and the
UV absorbers disclosed in U.S. Pat. No. 5,332,568, EP-A-517 104, EP-A-507 691, WO 93/17002 and EP-A-570 838;
2-phenylbenzimidazole-5-sulfonic acid and salts thereof;
menthyl o-aminobenzoates;
physical sunscreens coated or not as titanium dioxide, zinc oxide, iron oxides, mica, MnO, $Fe_2O_3$, $Ce_2O_3$, $Al_2O_3$,
$ZrO_2$. (surface coatings: polymethylmethacrylate, methicone (methylhydrogenpolysiloxane as described in
CAS 9004-73-3), dimethicone, isopropyl titanium triisostearate (as described in CAS 61417-49-0), metal soaps as
magnesium stearate (as described in CAS 4086-70-8), perfluoroalcohol phosphate as C9-15 fluoroalcohol phosphate
(as described in CAS 74499-44-8; JP 5-86984 , JP 4-330007)). The primary particle size is an average
of 15 nm-35 nm and the particle size in dispersion is in the range of 100 nm-300 nm.
aminohydroxy-benzophenone derivatives disclosed in DE 10011317, EP 1133980 and EP 1046391
phenyl-benzimidazole derivatives as disclosed in EP 1167358
the UV absorbers described in "Sunscreens", Eds. N. J. Lowe, N. A. Shaath, Marcel Dekker, Inc., New York and
Basle or in Cosmetics & Toiletries (107), 50ff (1992) also can be used as additional UV protective substances.

TABLE 2

Suitable UV filter substances which can be additionally used with
the UV absorbers according to the present invention

| | |
|---|---|
| DE 100331804 | Tab 1 p 4, tab 2 + 3 p 5 |
| EP 613893 | Ex 1-5 + 15, T 1, pp 6-8 |
| EP 1000950 | Comp. in table 1, pp 18-21 |
| EP 1005855 | T 3, p 13 |
| EP 1008586 | Ex 1-3, pp 13-15 |
| EP 1008593 | Ex 1-8, pp 4-5 |
| EP 1027883 | Compound VII, p 3 |
| EP 1027883 | Comp I-VI, p 3 |
| EP 1028120 | Ex 1-5, pp 5-13 |
| EP 1059082 | Ex 1; T 1, pp 9-11 |
| EP 1060734 | T 1-3, pp 11-14 |
| EP 1064922 | Compounds 1-34, pp 6-14 |
| EP 1081140 | Ex 1-9, pp 11-16 |
| EP 1103549 | Compounds 1-76, pp 39-51 |
| EP 1108712 | 4,5-Dimorpholino-3-hydroxypyridazine |
| EP 1123934 | T 3, p 10 |
| EP 1129695 | Ex 1-7, pp 13-14 |
| EP 1167359 | Ex 1 p11 and ex 2 p 12 |
| EP 1258481 | Ex 1, pp 7, 8 |
| EP 420707 B1 | Ex 3, p 13 (CAS Regno 80142-49-0) |
| EP 503338 | T 1, pp 9-10 |
| EP 517103 | Ex 3, 4, 9, 10 pp 6-7 |
| EP 517104 | Ex 1, T 1, pp 4-5; Ex 8, T 2, pp 6-8 |
| EP 626950 | all compounds |
| EP 669323 | Ex 1-3, p 5 |
| EP 780382 | Ex 1-11, pp 5-7 |
| EP 823418 | Ex 1-4, pp 7-8 |
| EP 826361 | T 1, pp 5-6 |
| EP 832641 | Ex 5 + 6 p 7; t 2, p 8 |
| EP 832642 | Ex 22, T 3 pp, 10-15; T4, p 16 |
| EP 852137 | T 2, pp 41-46 |
| EP 858318 | T 1, p 6 |
| EP 863145 | Ex 1-11, pp 12-18 |
| EP 895776 | Comp. in rows 48-58, p 3; R 25 + 33, p 5 |
| EP 911020 | T 2, p 11-12 |
| EP 916335 | T 2-4, pp 19-41 |
| EP 924246 | T 2, p 9 |
| EP 933376 | Ex 1-15, pp 10-21 |
| EP 944624 | Ex 1 + 2, pp 13-15 |
| EP 945125 | T 3 a + b, pp 14-15 |
| EP 967200 | Ex 2; T 3-5, pp 17-20 |
| EP 969004 | Ex 5, T 1, pp 6-8 |
| JP 2000319629 | CAS Regno. 80142-49-0, 137215-83-9, 307947-82-6 |
| U.S. Pat. No. 5635343 | all compounds on pp 5-10 |
| U.S. Pat. No. 5338539 | Ex 1-9, pp 3 + 4 |
| U.S. Pat. No. 5346691 | Ex 40, p 7; T 5, p 8 |
| U.S. Pat. No. 5801244 | Ex 1-5, pp 6-7 |
| WO 0149686 | Ex 1-5, pp 16-21 |
| WO 0168047 | Tables on pp 85-96 |
| WO 0181297 | Ex 1-3 pp 9-11 |
| WO 0238537 | All componds p 3, compounds on rows 1-10 p 4 |
| WO 9217461 | Ex 1-22, pp 10-20 |
| WO 9220690 | Polymeric comp in examples 3-6 |

TABLE 2-continued

Suitable UV filter substances which can be additionally used with the UV absorbers according to the present invention

| | |
|---|---|
| WO 9301164 | T 1 + 2, pp 13-22 |
| WO 9714680 | Ex 1-3, p 10 |

(Abbreviations
T: table,
R: row,
Comp: compound,
Ex: compound(s) of patent example,
p: page);
the generic scope of the UV absorbers is described in the left-hand column; specific compounds are indicated in the right-hand column

TABLE 3

Suitable UV filter substances and adjuvants which can be additionally used with the UV absorbers according to the present invention

| No. | Chemical Name | CAS No. |
|---|---|---|
| 1 | (+/−)-1,7,7-trimethyl-3-[(4-methylphenyl)methylene]bicyclo-[2.2.1]heptan-2-one; p-methyl benzylidene camphor | 36861-47-9 |
| 2 | 1,7,7-trimethyl-3-(phenylmethylene)bicyclo[2.2.1]heptan-2-one; benzylidene camphor | 15087-24-8 |
| 3 | (2-Hydroxy-4-methoxyphenyl)(4-methylphenyl)methanone | 1641-17-4 |
| 4 | 2,4-dihydroxybenzophenone | 131-56-6 |
| 5 | 2,2',4,4'-tetrahydroxybenzophenone | 131-55-5 |
| 6 | 2-Hydroxy-4-methoxy benzophenone; | 131-57-7 |
| 7 | 2-Hydroxy-4-methoxy benzophenone-5-sulfonic acid | 4065-45-6 |
| 8 | 2,2'-dihydroxy-4,4'-dimethoxybenzophenone | 131-54-4 |
| 9 | 2,2'-Dihydroxy-4-methoxybenzophenone | 131-53-3 |
| 10 | Alpha-(2-oxoborn-3-ylidene)toluene-4-sulphonic acid and its salts; Mexoryl SL | 56039-58-8 |
| 11 | 1-[4-(1,1-dimethylethyl)phenyl]-3-(4-methoxyphenyl)propane-1,3-dione; avobenzone | 70356-09-1 |
| 12 | Methyl N,N,N-trimethyl-4-[(4,7,7-trimethyl-3-oxobicyclo[2,2,1]hept-2-ylidene)methyl]anilinium sulphate; Mexoryl SO | 52793-97-2 |
| 22 | 3,3,5-Trimethyl cyclohexyl-2-hydroxy benzoate; homosalate | 118-56-9 |
| 23 | Isopentyl p-methoxycinnamate; isoamyl methoxy cinnamate | 71617-10-2 |
| 27 | Menthyl-o-aminobenzoate | 134-09-8 |
| 28 | Menthyl salicylate | 89-46-3 |
| 29 | 2-Ethylhexyl 2-cyano,3,3-diphenylacrylate; octocrylene | 6197-30-4 |
| 30 | 2-ethylhexyl 4-(dimethylamino)benzoate | 21245-02-3 |
| 31 | 2-ethylhexyl 4-methoxycinnamate; octyl methoxy cinnamate | 5466-77-3 |
| 32 | 2-ethylhexyl salicylate | 118-60-5 |
| 33 | Benzoic acid, 4,4',4''-(1,3,5-triazine-2,4,6-triyltriimino)tris-, tris(2-ethylhexyl)ester; 2,4,6-Trianilino-(p-carbo-2'-ethylhexyl-1'-oxi)-1,3,5-triazine; octyl triazone | 88122-99-0 |
| 34 | 4-aminobenzoic acid | 150-13-0 |
| 35 | Benzoic acid, 4-amino-, ethyl ester, polymer with oxirane | 113010-52-9 |
| 38 | 2-phenyl-1H-benzimidazole-5-sulphonic acid; phenylbenzimidazolsulfonic acid | 27503-81-7 |
| 39 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 40 | Triethanolamine salicylate | 2174-16-5 |
| 41 | 3,3'-(1,4-phenylenedimethylene)bis[7,7-dimethyl-2-oxo-bicyclo[2.2.1]heptane-1 methanesulfonic acid]; Cibafast H | 90457-82-2 |
| 42 | Titanium dioxide | 13463-67-7 |
| 44 | Zinc oxide | 1314-13-2 |
| 45 | 2,2'-Methylene-bis-[6-(2H-benzotriazol-2-yl)-4-(1,1,3,3-tetramethyl-butyl)-phenol]; Tinosorb M | 103597-45-1 |
| 46 | 2,4-bis{[4-(2-ethylhexyloxy)-2-hydroxy]-phenyl}-6-(4-methoxyphenyl)-(1,3,5)-triazine; Tinosorb S | 187393-00-6 |
| 47 | 1H-Benzimidazole-4,6-disulfonic acid, 2,2'-(1,4-phenylene)bis-, disodium salt | 180898-37-7 |
| 48 | Benzoic acid, 4,4'-[[6-[[4-[[(1,1-dimethylethyl)amino]carbonyl]phenyl]amino]1,3,5-triazine-2,4-diyl]diimino]bis-, bis(2-ethylhexyl)ester; diethylhexyl butamido triazone; Uvasorb HEB | 154702-15-5 |
| 49 | Phenol, 2-(2H-benzotriazol-2-yl)-4-methyl-6-[2-methyl-3-[1,3,3,3-tetramethyl-1-[(trimethylsilyl)oxy]disiloxanyl]propyl]-; drometrizole trisiloxane; Mexoryl XL | 155633-54-8 |
| 50 | Dimethicodiethylbenzalmalonate; Polysilicone 15; Parsol SLX | 207574-74-1 |
| 51 | Benzenesulfonic acid, 3-(2H-benzotriazol-2-yl)-4-hydroxy-5-(1-methylpropyl)-, monosodium salt; Tinogard HS | 92484-48-5 |
| 52 | Benzoic acid, 2-[4-(diethylamino)-2-hydroxybenzoyl]-, hexyl ester; Uvinul a plus | 302776-68-7 |

TABLE 3-continued

Suitable UV filter substances and adjuvants which can be additionally used with the UV absorbers according to the present invention

| No. | Chemical Name | CAS No. |
|---|---|---|
| 53 | 1-Dodecanaminium, N-[3-[[4-(dimethylamino)benzoyl]amino]propyl]N,N-dimethyl-, salt with 4-methylbenzenesulfonic acid (1:1); Escalol HP610 | 156679-41-3 |
| 54 | 1-Propanaminium, N,N,N-trimethyl-3-[(1-oxo-3-phenyl-2-propenyl)-amino]-, chloride | 177190-98-6 |
| 55 | 1H-Benzimidazole-4,6-disulfonic acid, 2,2'-(1,4-phenylene)bis- | 170864-82-1 |
| 56 | 1,3,5-Triazine, 2,4,6-tris(4-methoxyphenyl)- | 7753-12-0 |
| 57 | 1,3,5-Triazine, 2,4,6-tris[4-[(2-ethylhexyl)oxy]phenyl]- | 208114-14-1 |
| 58 | 1-Propanaminium, 3-[[3-[3-(2H-benzotriazol-2-yl)-5-(1,1-dimethylethyl)-4-hydroxyphenyl]-1-oxopropyl]amino]-N,N-diethyl-N-methyl-, methyl sulfate (salt) | 340964-15-0 |
| 59 | 2-Propenoic acid, 3-(1H-imidazol-4-yl)- | 104-98-3 |
| 60 | Benzoic acid, 2-hydroxy-, [4-(1-methylethyl)phenyl]methyl ester | 94134-93-7 |
| 61 | 1,2,3-Propanetriol,1-(4-aminobenzoate); glyceryl PABA | 136-44-7 |
| 62 | Benzeneacetic acid, 3,4-dimethoxy-a-oxo- | 4732-70-1 |
| 63 | 2-Propenoic acid, 2-cyano-3,3-diphenyl-, ethyl ester | 5232-99-5 |
| 64 | Anthralinic acid, p-menth-3-yl ester | 134-09-8 |
| 65 | 2,2'-bis(1,4-phenylene)-1H-benzimidazole-4,6-disulphonic acid mono sodium salt or Disodium phenyl dibenzimidazole tetrasulfonate or Neoheliopan AP | 349580-12-7, |
| 66 | 1,3,5-Triazine-2,4,6-triamine, N,N'-bis[4-[5-(1,1-dimethylpropyl)-2-benzoxazolyl]phenyl]-N''-(2-ethylhexyl)- or Uvasorb K2A | 288254-16-0 |
| 67 | Merocyanine derivatives as described in WO 2004006878 and in IPCOM000022279D | |

68

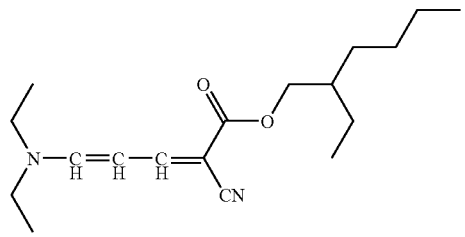

| | | |
|---|---|---|
| 68 | sterols (cholesterol, lanosterol, phytosterols), as described in WO 0341675 | |
| 69 | mycosporines and/or mycosporine-like amino acids as described in WO 2002039974, e.g. Helioguard 365 from Milbelle AG, isolated mycosporine like amino acids from the red alga *porphyra umbilicalis* (INCI: *Porphyra Umbilicalis*) that are encapsulated into liposomes,) | |
| 70 | alpha-lipoic-acid as described in DE 10229995 | |
| 71 | synthetic organic polymers as described in EP 1371358, [0033]-[0041] | |
| 72 | phyllosilicates as described in EP 1371357 [0034]-[0037] | |
| 73 | silica compounds as described in EP 1371356, [0033]-[0041] | |
| 74 | inorganic particles as described in DE 10138496 [0043]-[0055] | |
| 75 | latex particles as described in DE 10138496 [0027]-[0040] | |
| 76 | 1H-Benzimidazole-4,6-disulfonic acid, 2,2'-(1,4-phenylene)bis-, disodium salt; Bisimidazylate; Neo Heliopan APC | 180898-37-7 |

Preferably, the following UV filter combinations are of special interest:

UV-filter combinations (A) comprising ($a_1$) at least one symmetrical triazine derivatives of formula (1) and ($a_2$) at least one aminobenzophenone derivative of formula

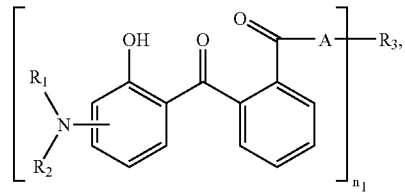

wherein $R_1$ and $R_2$ independently from each other are; $C_1$-$C_{20}$alkyl; $C_2$-$C_{20}$alkenyl; $C_3$-$C_{10}$cycloalkyl; $C_3$-$C_{10}$cycloalkenyl; or $R_1$ and $R_2$ together with the linking nitrogen atom form a 5- or 6-membered heterocyclic ring;

$n_1$ is a number from 1 to 4;

when $n_1$=1, $R_3$ is a saturated or unsaturated heterocyclic radical; hydroxy-$C_1$-$C_5$alkyl; cyclohexyl,M optionally substituted with one or more $C_1$-$C_5$alkyl; phenyl optionally substituted with a heterocyclic radical, aminocarbonyl or $C_1$-$C_5$alkylcarboxy;

when $n_1$ is 2, $R_3$ is an alkylene-, cycloalkylene, alkenylene or phenylene radical which is optionally substituted by a carbonyl- or carboxy group; a radical of formula .—$CH_2$—C≡C—$CH_2$—. or $R_3$ together with A forms a bivalent radical of the formula

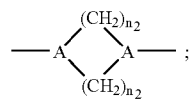

(1a)

wherein $n_2$ is a number from 1 to 3;

when $n_1$ is 3, $R_3$ is an alkanetriyl radical;

wenn $n_1$ is 4, $R_3$ is an alkanetetrayl radical;

A is —O—; or —N($R_5$)—; and $R_5$ is hydrogen; $C_1$-$C_5$alkyl; or hydroxy-$C_1$-$C_5$alkyl.

Most preferred are UV-filter combinations (A1) comprising ($a_3$) at least one compound of formula (6) and/or (9); and ($a_4$) the compound of formula

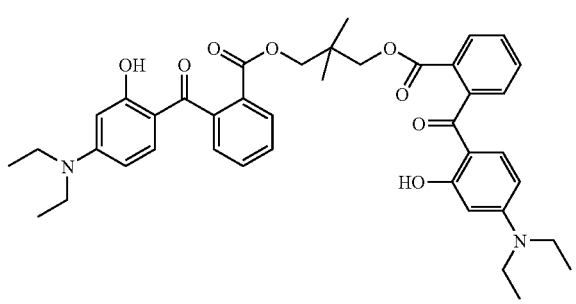

UV-filter combinations (B) comprising ($b_1$) at least one symmetrical triazine derivatives of formula (1); and ($b_2$) at least one aminobenzophenone derivative of the formula

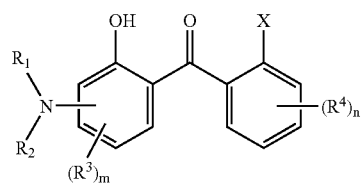

wherein $R^1$ and $R^2$ independently from each other is hydrogen, $C_1$-$C_{20}$alkyl; $C_2$-$C_{20}$alkenyl; $C_3$-$C_{10}$cycloalkenyl; wherein $R^1$ and $R^2$ may form a five- or six-membered ring;

$R^3$ and $R^4$ independently from each other is $C_1$-$C_{20}$alkyl; $C_2$-$C_{20}$alkenyl; $C_3$-$C_{10}$cycloalkenyl, $C_1$-$C_{20}$alkoxy, $C_1$-$C_{20}$alkoxycarbonyl, $C_1$-$C_{20}$alkylamino, di($C_1$-$C_{20}$alkyl)amino, optionally substituted aryl or Heteroaryl;

X is hydrogen; COOR$^5$; or CONR$^6$R$^7$;

$R^5$, $R^6$, $R^7$ independently from each other are hydrogen, $C_1$-$C_{20}$alkyl; $C_2$-$C_{20}$alkenyl; $C_3$-$C_{10}$cycloalkyl; $C_3$-$C_{10}$cycloalkenyl; (Y—O)$_q$-Z; optionally substituted aryl;

Y is —($CH_2$)$_2$—; —($CH_2$)$_3$—; —($CH_2$)$_4$—; —CH($CH_3$)—$CH_2$—;

Z is —$CH_2$—$CH_3$; —$CH_2$—$CH_2$—$CH_3$; —$CH_2$—$CH_2$—$CH_2$—$CH_3$; CH($CH_3$)—$CH_3$;

m is 0; 1; 2; or 3;

n is 0; 1; 2; 3; or 4; and q is a number from 1 to 20.

Most preferred are UV-filter combinations (B1) comprising ($b_3$) the compound of formula (6) and/or (9); and ($b_4$) the compound of formula

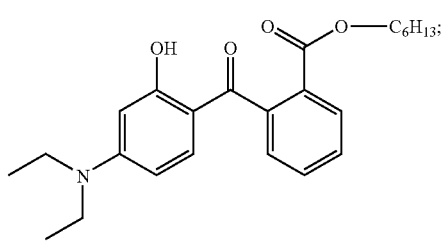

UV-filter combinations (C) comprising ($c_1$) at least one symmetrical triazine derivatives of formula (1); and ($c_2$) at least one benzotriazole derivative of formula

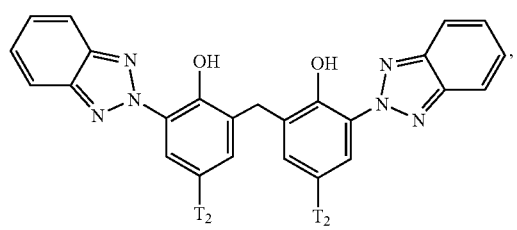

wherein $T_2$ is $C_1$-$C_{10}$alkyl or phenyl-substituted $C_1$-$C_4$alkyl;

Most preferred are UV-filter combinations (C1) comprising
($c_3$) the compound of formula (6) and/or (9); and
($c_4$) the micronized compound of formula

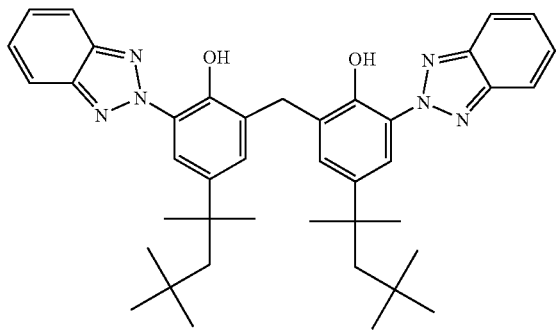

UV-filter combinations (D) comprising
($d_1$) at least one symmetrical triazine derivatives of formula (1); and
($d_2$) at least one compound of formula

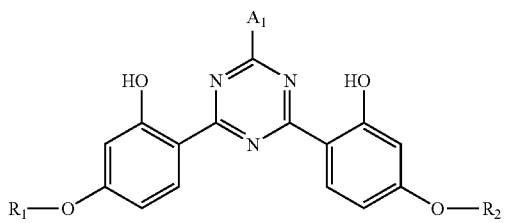

(4a)

in which
$R_1$ and $R_2$, independently of one another, are $C_3$-$C_{18}$alkyl; $C_2$-$C_{18}$alkenyl; a radical of the formula —$CH_2$—CH(—OH)—$CH_2$—O-$T_1$; or
$R_1$ and $R_2$ are a radical of the formula

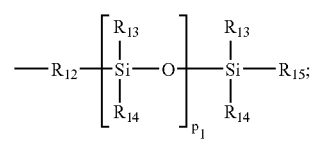

$R_{12}$ is a direct bond; a straight-chain or branched $C_1$-$C_4$alkylene radical or a radical of the formula —$C_{m_1}H_{2m_1}$— or —$C_{m_1}H_{2m_1}$—O—;

$R_{13}$, $R_{14}$ and $R_{15}$, independently of one another, are $C_1$-$C_{18}$alkyl; $C_1$-$C_{18}$alkoxy or a radical of the formula

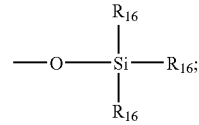

$R_{16}$ is $C_1$-$C_5$alkyl;
$m_1$ and $m_3$, independently of one another, are 1 to 4;
$p_1$ is 0; or a number from 1 to 5;
$A_1$ is a radical of the formula

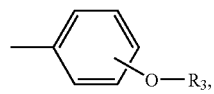
(1b)

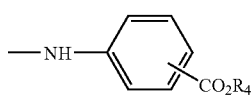
(1c)

of the formula

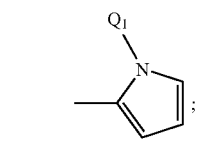
(1d)

$R_3$ is hydrogen; $C_1$-$C_{10}$alkyl, —$(CH_2CHR_5$—O$)_{n_1}$—$R_4$; or a radical of the formula

—$CH_2$—CH(—OH)—$CH_2$—O-$T_1$;

$R_4$ is hydrogen; M; $C_1$-$C_5$alkyl; or a radical of the formula
—$(CH_2)_{m_2}$—O-$T_1$;
$R_5$ is hydrogen; or methyl;
$T_1$ is hydrogen; or $C_1$-$C_8$alkyl;
$Q_1$ $C_1$-$C_{18}$alkyl;
M is a metal cation;
$m_2$ is 1 to 4; and
$n_1$ is 1-16.

Most preferred are UV-filter combinations (D1) comprising
($d_3$) the compound of formula (6) and/or (9); and
($d_4$) the compound of formula

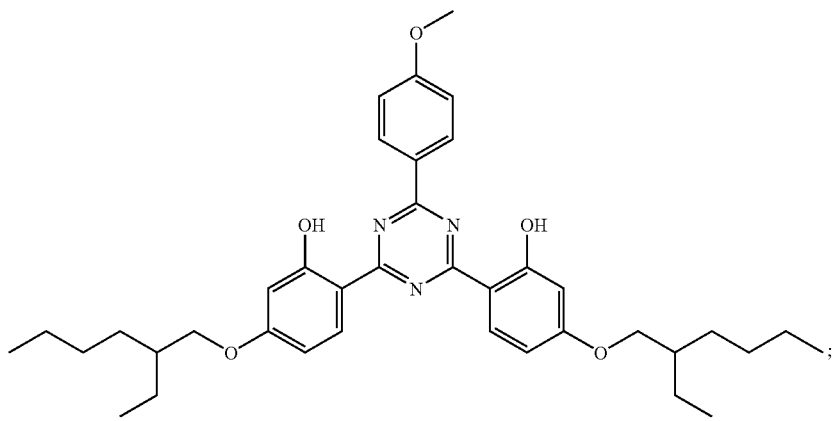

UV-filter combinations (E) comprising
($e_1$) at least one symmetrical triazine derivatives of formula (1) and
($e_2$) at least one hydroxyphenyltriazine compound of formula

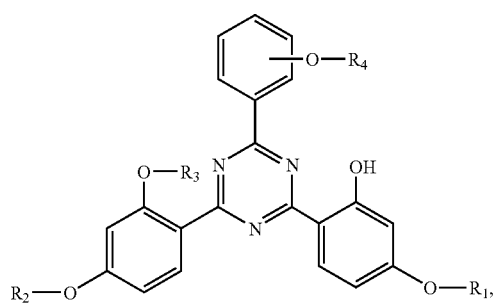

(1)

wherein
$R_1$, $R_2$ and $R_3$ are each independently of the others $C_1$-$C_{18}$alkyl; $C_2$-$C_{10}$alkenyl; or phenyl-$C_1$-$C_4$alkyl; and
$R_4$ is hydrogen; or $C_1$-$C_5$alkyl.

Most preferred are UV-filter combinations (E1) comprising
($e_3$) the compound of formula (6) and/or (9); and
($e_4$) the compound of formula

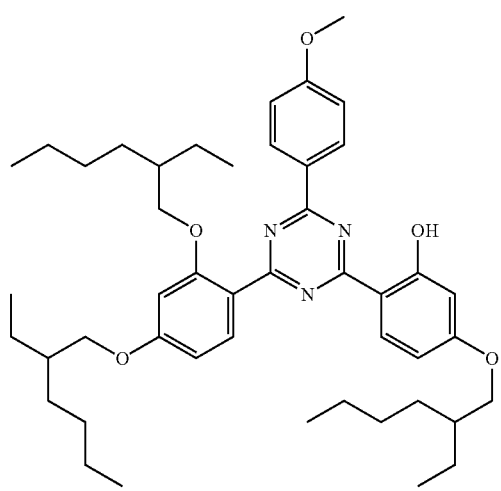

UV-filter combinations (F) comprising
($f_1$) at least one symmetrical triazine derivatives of formula (1); and
($f_2$) at least one dibenzoylmethane derivative of formula

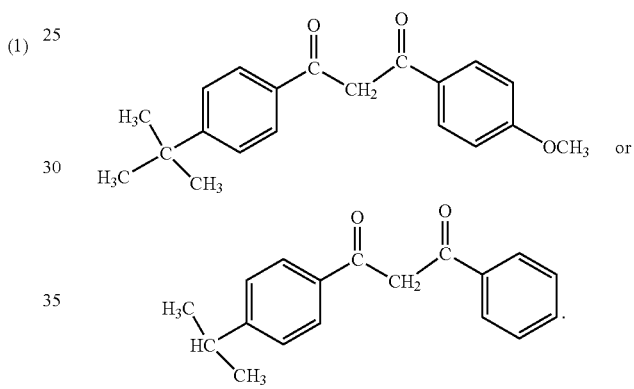

Most preferred are UV-filter combinations (F1) comprising
($f_3$) the compound of formula (6) and/or (9); and
($f_4$) 1-[4-(1,1-dimethylethyl)phenyl]-3-(4-methoxyphenyl)propane-1,3-dione (Avobenzone);

UV-filter combinations (G) comprising
($g_1$) at least one symmetrical triazine derivative of formula (1), preferably the compound of formula (6) and/or (9); and
($g_2$) disodium phenyl dibenzimidazole tetrasulfonate (Heliopan AP).

UV-filter combinations (H) comprising
($h_1$) at least one symmetrical triazine derivatives of formula (1); and
($h_2$) benzoxazole-substituted triazines of formula (h21)

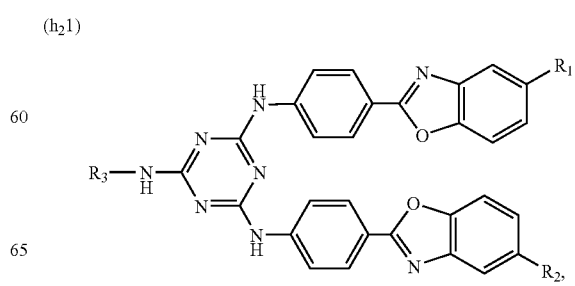

wherein
R$_1$, R$_2$ and R$_3$ independently from each other are branched or unbranched C$_1$-C$_{12}$alkyl.

Most preferred are UV-filter combinations comprising
(h$_3$) the compound of formula (6) and/or (9); and
(h$_4$) 1,3,5-triazine-2,4,6-triamine, N,N'-bis[4-[5-(1,1-dimethylpropyl)-2-benzoxazolyl]phenyl]-N''-(2-ethylhexyl); (CAS No. 288254-16-0).

Furthermore, UV filter combination (H2) comprising
(h$_5$) the compound of formula (6) or (9); and
(h$_6$) at least one of the compound of formula (h$_2$1), wherein
(h$_{61}$) R$_1$ and R$_2$ are tert.amyl; and R$_3$ is tert.butyl; or wherein
(h$_{62}$) R$_1$ and R$_2$ are tert.butyl and R$_3$ is tert.octyl; or wherein
(h$_{63}$) R$_1$ and R$_2$ are tert.butyl; and R$_3$ is 2-ethylhexyl; or wherein
(h$_{64}$) R$_1$ and R$_2$ are tert.amyl; and R$_3$ is 2-ethylhexyl;
are of preferred interest.

UV-filter combinations (I) comprising
(i$_1$) at least one symmetrical triazine derivatives of formula (1), preferably the compound of formula (6) and/or (9); and
(i$_2$) 2-(2H-benzotriazol-2-yl)4-methyl-6-[2-methyl-3-[1,3,3,3-tetramethyl-1-[(trimethyl-silyl)oxy]disiloxanyl]propyl]-; (CAS-No. 155633-54-8; Drometrizole Trisiloxane; Mexoryl XL);

UV-filter combinations (K) comprising
(k$_1$) at least one symmetrical triazine derivatives of formula (1), preferably the compound of formula (6) and/or (9); and
(k$_2$) siloxanes and silicones, di-Me, 1-[[4-[3-ethoxy-2-(ethoxycarbonyl)-3-oxo-1-propenyl]phenoxy]methyl]ethenyl Me, 3-[4-[3-ethoxy-2-(ethoxycarbonyl)-3-oxo-1-propenyl]-phenoxy]-1-propenyl Me, Me hydrogen (Dimethicodiethylbenzalmalonate; CAS-No. 207574-74-1);

UV-filter combinations (L) comprising
(l$_1$) at least one symmetrical triazine derivatives of formula (1), preferably the compound of formula (6) and/or (9); and
(l$_2$) (±)-1,7,7-trimethyl-3-[(4-methylphenyl)methylene]bicyclo[2.2.1]heptan-2-one; p-methyl benzylidene camphor;

UV-filter combinations (M) comprising
(m$_1$) at least one symmetrical triazine derivatives of formula (1), preferably the compound of formula (6) and/or (9); and
(m$_2$)-(2-oxoborn-3-ylidene)toluene-4-sulphonic acid and its salts (Mexoryl SL);

UV-filter combinations (N) comprising
(n$_1$) at least one symmetrical triazine derivatives of formula (1), preferably the compound of formula (6) and/or (9); and
(n$_2$) methyl N,N,N-trimethyl4-[(4,7,7-trimethyl-3-oxobicyclo[2,2,1]hept-2-ylidene)methyl]-anilinium sulphate (Mexoryl SO);

UV-filter combinations (O) comprising
(o$_1$) at least one symmetrical triazine derivatives of formula (1), preferably the compound of formula (6) and/or (9); and
(o$_2$) 2-ethylhexyl 2-cyano,3,3-diphenylacrylate (Octocrylene);

UV-filter combinations (P) comprising
(p$_1$) at least one symmetrical triazine derivatives of formula (1), preferably the micronized compound of formula (6) and/or (9); and
(p$_2$) 2-ethylhexyl 4-methoxycinnamate (octyl methoxy cinnamate);

UV-filter combinations (Q) comprising
(q$_1$) at least one symmetrical triazine derivative of formula (1), preferably the compound of formula (6) and/or (9); and
(q$_2$) benzoic acid, 4,4'4''-(1,3,5-triazine-2,4,6-triyltriimino) tris-,tris(2-ethylhexyl)ester; 2,4,6-Trianilino-(p-carbo-2'-ethylhexyl-1'-oxi)-1,3,5-triazine (Octyl Triazone);

UV-filter combinations (R) comprising
(r$_1$) at least one symmetrical triazine derivative of formula (1), preferably the compound of formula (6) and/or (9); and
(r$_2$) 2-phenyl-1H-benzimidazole-5-sulphonic acid (Phenylbenzimidazolsulfonic Acid);

UV-filter combinations (S) comprising
(s$_1$) at least one symmetrical triazine derivative of formula (1), preferably the compound of formula (6) and/or (9); and
(s2) benzoic acid,4,4'-[[6-[[4-[[(1,1-dimethylethyl)amino]carbonyl]phenyl]amino]1,3,5-triazine-2,4-diyl]diimino]bis-,bis(2-ethylhexyl)ester; diethylhexyl butamido triazone (Uvasorb HEB).

In the compositions (A)-(S) the compound of formula (1), (6) and (9) respectively are preferably present in the composition in micronized form.

The compounds of formula (1) may also be used as as an anti-wrinkle perception modifier (see Example 29). This is a futher object of the present invention.

Preferably, the following combinations comprising UV absorbersare of special interest:

| No. | A | | CAS No. of A | B:<br>UV absorber dispersion comprising the compound of formula (101) according to Example 6 or 7 |
|---|---|---|---|---|
| Comb 001 | (+/−)-1,7,7-trimethyl-3-[(4-methylphenyl)methylene]bicyclo[2.2.1]heptan-2-one; p-methyl benzylidene camphor | | 36861-47-9 | X |
| Comb 002 | 1,7,7-trimethyl-3-(phenylmethyllene)-bicyclo[2.2.1]heptan-2-one; benzylidene camphor | | 15087-24-8 | X |
| Comb 003 | (2-Hydroxy-4-methoxyphenyl)(4-methylphenyl)methanone | | 1641-17-4 | X |
| Comb 004 | 2,4-dihydroxybenzophenone | | 131-56-6 | X |
| Comb 005 | 2,2',4,4'-tetrahydroxybenzophenone | | 131-55-5 | X |

-continued

| No. | A | CAS No. of A | B:<br>UV absorber dispersion comprising the compound of formula (101) according to Example 6 or 7 |
|---|---|---|---|
| Comb 006 | 2-Hydroxy-4-methoxy benzophenone; | 131-57-7 | X |
| Comb 007 | 2-Hydroxy-4-methoxy benzophenone-5-sulfonic acid | 4065-45-6 | X |
| Comb 008 | 2,2'-dihydroxy-4,4'-dimethoxybenzophenone | 131-54-4 | X |
| Comb 009 | 2,2'-Dihydroxy-4-methoxybenzophenone | 131-53-3 | X |
| Comb 010 | Alpha-(2-oxoborn-3-ylidene)toluene-4-sulphonic acid and its salts; Mexoryl SL | 56039-58-8 | X |
| Comb 011 | 1-[4-(1,1-dimethylethyl)phenyl]-3-(4-methoxyphenyl)propane-1,3-dione; avobenzone | 70356-09-1 | X |
| Comb 012 | Methyl N,N,N-trimethyl-4-[(4,7,7-trimethyl-3-oxobicyclo[2,2,1]hept-2-ylidene)methyl]anilinium sulphate; Mexoryl SO | 52793-97-2 | X |
| Comb 013 | 3,3,5-Trimethyl cyclohexyl-2-hydroxy benzoate; homosalate | 118-56-9 | X |
| Comb 014 | Isopentyl p-methoxycinnamate; isoamyl methoxy cinnamate | 71617-10-2 | X |
| Comb 015 | Menthyl-o-aminobenzoate | 134-09-8 | X |
| Comb 016 | Menthyl salicylate | 89-46-3 | X |
| Comb 017 | 2-Ethylhexyl 2-cyano,3,3-diphenylacrylate; octocrylene | 6197-30-4 | X |
| Comb 018 | 2-ethylhexyl 4-(dimethylamino)benzoate | 21245-02-3 | X |
| Comb 019 | 2-ethylhexyl 4-methoxycinnamate; octyl methoxy cinnamate | 5466-77-3 | X |
| Comb 020 | 2-ethylhexyl salicylate | 118-60-5 | X |
| Comb 021 | Benzoic acid, 4,4',4''-(1,3,5-triazine-2,4,6-triyltriimino)tris-, tris(2-ethyl-hexyl)ester; 2,4,6-Trianilino-(p-carbo-2'-ethylhexyl-1'-oxi)-1,3,5-triazine; octyl triazone | 88122-99-0 | X |
| Comb 022 | 4-aminobenzoic acid | 150-13-0 | X |
| Comb 023 | Benzoic acid, 4-amino-, ethyl ester, polymer with oxirane | 113010-52-9 | X |
| Comb 024 | 2-phenyl-1H-benzimidazole-5-sulphonic acid; phenylbenzimidazolsulfonic acid | 27503-81-7 | X |
| Comb 025 | 2-Propenamide, N-[[4-[(4,7,7-trimethyl-3-oxobicyclo[2.2.1]hept-2-ylidene)methyl]phenyl]methyl]-, homopolymer | 147897-12-9 | X |
| Comb 026 | Triethanolamine salicylate | 2174-16-5 | X |
| Comb 027 | 3,3'-(1,4-phenylenedimethylene)bis[7,7-dimethyl-2-oxo-bicyclo[2.2.1]heptane-1-methanesulfonic acid]; Cibafast H | 90457-82-2 | X |
| Comb 028 | Titanium dioxide | 13463-67-7 | X |
| Comb 029 | Zinc oxide | 1314-13-2 | X |
| Comb 030 | 2,2'-Methylene-bis-[6-(2H-benzotriazol-2-yl)-4-(1,1,3,3-tetramethylbutyl)-phenol]; Tinosorb M | 103597-45-1 | X |
| Comb 031 | 2,4-bis{[4-(2-ethylhexyloxy)-2-hydroxy]-phenyl}-6-(4-methoxyphenyl)-(1,3,5)-triazine; Tinosorb S | 187393-00-6 | X |
| Comb 032 | 1H-Benzimidazole-4,6-disulfonic acid, 2,2'-(1,4-phenylene)bis-, disodium salt | 180898-37-7 | X |
| Comb 033 | Benzoic acid, 4,4'-[[6-[[[(1,1-dimethyl-ethyl)amino]carbonyl]phenyl]amino]1,3,5-triazine-2,4-diyl]diimino]bis-, bis(2-ethylhexyl)ester; diethylhexyl butamido triazone; Uvasorb HEB | 154702-15-5 | X |
| Comb | Phenol, 2-(2H-benzotriazol-2-yl)-4-methyl- | 155633-54-8 | X |

-continued

| No. | A | CAS No. of A | B: UV absorber dispersion comprising the compound of formula (101) according to Example 6 or 7 |
|---|---|---|---|
| 034 | 6-[2-methyl-3-[1,3,3,3-tetramethyl-1-[(trimethylsilyl)oxy]disiloxanyl]propyl]-; drometrizole trisiloxane; Mexoryl XL | | |
| Comb 035 | Dimethicodiethylbenzalmalonate; Polysilicone 15; Parsol SLX | 207574-74-1 | X |
| Comb 036 | Benzenesulfonic acid, 3-(2H-benzotriazol-2-yl)-4-hydroxy-5-(1-methylpropyl)-, monosodium salt ; Tinogard HS | 92484-48-5 | X |
| Comb 037 | Benzoic acid, 2-[4-(diethylamino)-2-hydroxybenzoyl]-, hexyl ester; Uvinul a plus | 302776-68-7 | X |
| Comb 038 | 1-Dodecanaminium, N-[3-[[4-(dimethyl-amino)benzoyl]amino]propyl]N,N-dimethyl-, salt with 4-methylbenzene-sulfonic acid (1:1); Escalol HP610 | 156679-41-3 | X |
| Comb 039 | 1-Propanaminium, N,N,N-trimethyl-3-[(1-oxo-3-phenyl-2-propenyl)amino]-, chloride | 177190-98-6 | X |
| Comb 040 | 1H-Benzimidazole-4,6-disulfonic acid, 2,2'-(1,4-phenylene)bis- | 170864-82-1 | X |
| Comb 041 | 1,3,5-Triazine, 2,4,6-tris(4-methoxy-phenyl)- | 7753-12-0 | X |
| Comb 042 | 1,3,5-Triazine, 2,4,6-tris[4-[(2-ethyl-hexyl)oxy]phenyl]- | 208114-14-1 | X |
| Comb 043 | 1-Propanaminium, 3-[[3-[3-(2H-benzo-triazol-2-yl)-5-(1,1-dimethylethyl)-4-hydroxyphenyl]-1-oxopropyl]amino]-N,N-diethyl-N-methyl-, methyl sulfate (salt) | 340964-15-0 | X |
| Comb 044 | 2-Propenoic acid, 3-(1H-imidazol-4-yl)- | 104-98-3 | X |
| Comb 045 | Benzoic acid, 2-hydroxy-, [4-(1-methyl-ethyl)phenyl]methyl ester | 94134-93-7 | X |
| Comb 046 | 1,2,3-Propanetriol,1-(4-aminobenzoate); glyceryl PABA | 136-44-7 | X |
| Comb 047 | Benzeneacetic acid, 3,4-dimethoxy-a-oxo- | 4732-70-1 | X |
| Comb 048 | 2-Propenoic acid, 2-cyano-3,3-diphenyl-, ethyl ester | 5232-99-5 | X |
| Comb 049 | Anthralinic acid, p-menth-3-yl ester | 134-09-8 | X |
| Comb 050 | 2,2'-bis(1,4-phenylene)-1H-benzimidazole-4,6-disulphonic acid mono sodium salt or Disodium phenyl dibenzimidazole tetrasulfonate (Neoheliopan AP) | 349580-12-7, | X |
| Comb 051 | 1,3,5-Triazine-2,4,6-triamine, N,N'-bis[4-[5-(1,1-dimethylpropyl)-2-benzoxazolyl]-phenyl]-N''-(2-ethylhexyl)- or Uvasorb K2A | 288254-16-0 | X |
| Comb 052 | Merocyanine derivatives as described in WO 2004006878 and in IPCOM000022279D | | X |
| Comb 053 | | | X |
| Comb 054 | sterols (cholesterol, lanosterol, phyto-sterols), as described in WO 0341675 | | X |
| Comb 55 | mycosporines and/or mycosporine-like amino acids as described in WO 2002039974, e.g. Helioguard 365 from Milbelle AG, isolated mycosporine like amino acids from the red alga *porphyra umbilicalis* (INCI: *Porphyra Umbilicalis*) that are encapsulated into liposomes,) | | X |
| Comb 056 | alpha-lipoic-acid as described in DE 10229995 | | X |
| Comb 057 | synthetic organic polymers as described in EP 1371358, [0033]-[0041] | | X |
| Comb | phyllosilicates as described in EP | | X |

| No. | A | CAS No. of A | B: UV absorber dispersion comprising the compound of formula (101) according to Example 6 or 7 |
|---|---|---|---|
| Comb 058 | silica compounds as described in 1371357 [0034]-[0037] | | X |
| Comb 059 | silica compounds as described in EP 1371356, [0033]-[0041] | | X |
| Comb 060 | inorganic particles as described in DE 10138496 [0043]-[0055] | | X |
| Comb 061 | latex particles as described in DE 10138496 [0027]-[0040] | | X |

Furthermore, the following specific UV filter combinations are of specific interest:

| No. | A | CAS No. of A | UV absorber dispersion comprising the compound of formula (103) prepared according to Example 5 or 6 |
|---|---|---|---|
| Comb 062 | (+/−)-1,7,7-trimethyl-3-[(4-methylphenyl)-methylene]bicyclo[2.2.1]heptan-2-one; p-methyl benzylidene camphor | 36861-47-9 | X |
| Comb 063 | 1,7,7-trimethyl-3-(phenylmethylene)bi-cyclo[2.2.1]heptan-2-one; benzylidene camphor | 15087-24-8 | X |
| Comb 064 | (2-Hydroxy-4-methoxyphenyl)(4-methylphenyl)methanone | 1641-17-4 | X |
| Comb 065 | 2,4-dihydroxybenzophenone | 131-56-6 | X |
| Comb 066 | 2,2',4,4'-tetrahydroxybenzophenone | 131-55-5 | X |
| Comb 067 | 2-Hydroxy-4-methoxy benzophenone; | 131-57-7 | X |
| Comb 068 | 2-Hydroxy-4-methoxy benzophenone-5-sulfonic acid | 4065-45-6 | X |
| Comb 069 | 2,2'-dihydroxy-4,4'-dimethoxybenzophenone | 131-54-4 | X |
| Comb 070 | 2,2'-Dihydroxy-4-methoxybenzophenone | 131-53-3 | X |
| Comb 071 | Alpha-(2-oxoborn-3-ylidene)toluene-4-sulphonic acid and its salts; Mexoryl SL | 56039-58-8 | X |
| Comb 072 | 1-[4-(1,1-dimethylethyl)phenyl]-3-(4-methoxyphenyl)propane-1,3-dione; avobenzone | 70356-09-1 | X |
| Comb 073 | Methyl N,N,N-trimethyl-4-[(4,7,7-trimethyl-3-oxobicyclo[2,2,1]hept-2-ylidene)methyl]-anilinium sulphate; Mexoryl SO | 52793-97-2 | X |
| Comb 074 | 3,3,5-Trimethyl cyclohexyl-2-hydroxy benzoate; homosalate | 118-56-9 | X |
| Comb 075 | Isopentyl p-methoxycinnamate; isoamyl methoxy cinnamate | 71617-10-2 | X |
| Comb 076 | Menthyl-o-aminobenzoate | 134-09-8 | X |
| Comb 077 | Menthyl salicylate | 89-46-3 | X |
| Comb 078 | 2-Ethylhexyl 2-cyano,3,3-diphenylacrylate; octocrylene | 6197-30-4 | X |
| Comb 079 | 2-ethylhexyl 4-(dimethylamino)benzoate | 21245-02-3 | X |
| Comb 080 | 2-ethylhexyl 4-methoxycinnamate; octyl methoxy cinnamate | 5466-77-3 | X |
| Comb 081 | 2-ethylhexyl salicylate | 118-60-5 | X |
| Comb 082 | Benzoic acid,4,4',4''-(1,3,5-triazine-2,4,6-triyltriimino)tris-, tris(2-ethylhexyl)ester; 2,4,6-Trianilino-(p-carbo-2'-ethylhexyl-1'-oxi)-1,3,5-triazine; octyl triazone | 88122-99-0 | X |
| Comb 083 | 4-aminobenzoic acid | 150-13-0 | X |

-continued

| No. | A | CAS No. of A | UV absorber dispersion comprising the compound of formula (103) prepared according to Example 5 or 6 |
|---|---|---|---|
| Comb 084 | Benzoic acid, 4-amino-, ethyl ester, polymer with oxirane | 113010-52-9 | X |
| Comb 085 | 2-phenyl-1H-benzimidazole-5-sulphonic acid; phenylbenzimidazolsulfonic acid | 27503-81-7 | X |
| Comb 086 | 2-Propenamide, N-[[4-[(4,7,7-trimethyl-3-oxobicyclo[2.2.1]hept-2-ylidene)methyl]-phenyl]methyl]-, homopolymer | 147897-12-9 | X |
| Comb 087 | Triethanolamine salicylate | 2174-16-5 | X |
| Comb 088 | 3,3'-(1,4-phenylenedimethylene)bis[7,7-dimethyl-2-oxo-bicyclo[2.2.1]heptane-1-methanesulfonic acid]; Cibafast H | 90457-82-2 | X |
| Comb 089 | Titanium dioxide | 13463-67-7 | X |
| Comb 090 | Zinc oxide | 1314-13-2 | X |
| Comb 091 | 2,2'-Methylene-bis-[6-(2H-benzotriazol-2-yl)-4-(1,1,3,3-tetramethylbutyl)-phenol]; Tinosorb M | 103597-45-1 | X |
| Comb 092 | 2,4-bis{[4-(2-ethylhexyloxy)-2-hydroxy]-phenyl}-6-(4-methoxyphenyl)-(1,3,5)-triazine; Tinosorb S | 187393-00-6 | X |
| Comb 093 | 1H-Benzimidazole-4,6-disulfonic acid, 2,2'-(1,4-phenylene)bis-, disodium salt | 180898-37-7 | X |
| Comb 094 | Benzoic acid, 4,4'-[[6-[[4-[[(1,1-dimethylethyl)amino]carbonyl]phenyl]amino] 1,3,5-triazine-2,4-diyl]diimino]bis-, bis(2-ethylhexyl)ester; diethylhexyl butamido triazone; Uvasorb HEB | 154702-15-5 | X |
| Comb 095 | Phenol, 2-(2H-benzotriazol-2-yl)-4-methyl-6-[2-methyl-3-[1,3,3,3-tetramethyl-1-[(trimethylsilyl)oxy]disiloxanyl]propyl]-; drometrizole trisiloxane; Mexoryl XL | 155633-54-8 | X |
| Comb 096 | Dimethicodiethylbenzalmalonate; Polysilicone 15; Parsol SLX | 207574-74-1 | X |
| Comb 097 | Benzenesulfonic acid, 3-(2H-benzotriazol-2-yl)-4-hydroxy-5-(1-methylpropyl)-, monosodium salt; Tinogard HS | 92484-48-5 | X |
| Comb 098 | Benzoic acid, 2-[4-(diethylamino)-2-hydroxy-benzoyl]-, hexyl ester; Uvinul a plus | 302776-68-7 | X |
| Comb 099 | 1-Dodecanaminium, N-[3-[[4-(dimethylamino)benzoyl]amino]propyl]N,N-dimethyl-, salt with 4-methylbenzenesulfonic acid (1:1) (Escalol HP610) | 156679-41-3 | X |
| Comb 100 | 1-Propanaminium, N,N,N-trimethyl-3-[(1-oxo-3-phenyl-2-propenyl)amino]-chloride oxo-3-phenyl-2-propenyl)amino]-, chloride | 177190-98-6 | X |
| Comb 101 | 1H-Benzimidazole-4,6-disulfonic acid, 2,2'-(1,4-phenylene)bis- | 170864-82-1 | X |
| Comb 102 | 1,3,5-Triazine, 2,4,6-tris(4-methoxyphenyl)- | 7753-12-0 | X |
| Comb 103 | 1,3,5-Triazine, 2,4,6-tris[4-[(2-ethylhexyl)-oxy]phenyl]- | 208114-14-1 | X |
| Comb 104 | 1-Propanaminium, 3-[[3-[3-(2H-benzotriazol-2-yl)-5-(1,1-dimethylethyl)-4-hydroxyphenyl]-1-oxopropyl]amino]-N,N-diethyl-N-methyl-, methyl sulfate (salt) | 340964-15-0 | X |
| Comb 105 | 2-Propenoic acid, 3-(1H-imidazol-4-yl)- | 104-98-3 | X |
| Comb 106 | Benzoic acid, 2-hydroxy-, [4-(1-methylethyl)phenyl]methyl ester | 94134-93-7 | X |
| Comb 107 | 1,2,3-Propanetriol, 1-(4-aminobenzoate); glyceryl PABA | 136-44-7 | X |
| Comb 108 | Benzeneacetic acid, 3,4-dimethoxy-a-oxo- | 4732-70-1 | X |
| Comb 109 | 2-Propenoic acid, 2-cyano-3,3-diphenyl-, ethyl ester | 5232-99-5 | X |
| Comb 110 | Anthralinic acid, p-menth-3-yl ester | 134-09-8 | X |

-continued

| No. | A | CAS No. of A | UV absorber dispersion comprising the compound of formula (103) prepared according to Example 5 or 6 |
|---|---|---|---|
| Comb 111 | 2,2'-bis(1,4-phenylene)-1H-benzimidazole-4,6-disulphonic acid mono sodium salt or Disodium phenyl dibenzimidazole tetrasulfonate or Neoheliopan AP | 349580-12-7, | X |
| Comb 112 | 1,3,5-Triazine-2,4,6-triamine, N,N'-bis[4-[5-(1,1-dimethylpropyl)-2-benzoxazolyl]phenyl]-N''-(2-ethylhexyl)- or Uvasorb K2A | 288254-16-0 | X |
| Comb 113 | Merocyanine derivatives as described in WO 2004006878 and IPCOM000022279D | | X |
| Comb 114 | [structure: diethylamino substituted cyanoacrylate, 2-ethylhexyl ester] | | X |
| Comb 115 | sterols (cholesterol, lanosterol, phylosterols), as described in WO 0341675 | | X |
| Comb 116 | mycosporines and/or mycosporine-like amino acids as described in WO 2002039974, e.g. Helioguard 365 from Milbelle AG, isolated mycosporine like amino acids from the red alga *porphyra umbilicalis* (INCI: *Porphyra Umbilicalis*) that are encapsulated into liposomes,) | | X |
| Comb 117 | alpha-lipoic-acid as described in DE 10229995 | | X |
| Comb 118 | synthetic organic polymers as described in EP 1371358, [0033]-[0041] | | X |
| Comb 119 | phyllosilicates as described in EP 1371357 [0034]-[0037] | | X |
| Comb 120 | silica compounds as described in EP 1371356, [0033]-[0041] | | X |
| Comb 121 | inorganic particles as described in DE 10138496 [0043]-[0055] | | X |
| Comb 122 | latex particles as described in DE 10138496 [0027]-[0040] | | X |
| Comb 123 | micronized compound of formula (6) | | X |

Furthermore, the following specific UV filter combinations are of specific interest:

| No. | UV filter (A) | UV filter (B) | UV filter (C) |
|---|---|---|---|
| Comb 124 | 2-ethylhexyl 4-methoxy-cinnamate; octyl methoxy cinnamate | micronized UV absorber of formula (103) | micronized UV absorber of formula (101) |
| Comb 125 | 2-ethylhexyl 4-methoxycinnamate; octyl methoxy cinnamate | Benzoic acid, 2-[4-(diethyl-amino)-2-hydroxybenzoyl]-, hexyl ester; Uvinul a plus | micronized UV absorber of formula (101) |
| Comb 126 | 2-ethylhexyl 4-methoxy-cinnamate; octyl methoxy cinnamate | Benzoic acid, 2-[4-(diethyl-amino)-2-hydroxybenzoyl]-, hexyl ester; Uvinul a plus | micronized UV absorber of formula (103) |
| Comb 127 | 2-ethylhexyl 4-methoxy-cinnamate; octyl methoxy cinnamate | Benzoic acid, 4,4'-[[6-[[4-[[(1,1-dimethylethyl)amino]-carbonyl]phenyl]amino]1,3,5-triazine-2,4-diyl]diimino]bis-, bis(2-ethylhexyl)ester; di-ethylhexyl butamido triazone; Uvasorb HEB | micronized UV absorber of formula (101) |

-continued

| No. | UV filter (A) | UV filter (B) | UV filter (C) |
|---|---|---|---|
| Comb 128 | 2-ethylhexyl 4-methoxy-cinnamate; octyl methoxy cinnamate | 2,2'-bis(1,4-phenylene)-1H-benzimidazole-4,6-disulphonic acid mono sodium salt or Disodium phenyl dibenzimidazole tetrasulfonate or Neoheliopan AP | micronized UV absorber of formula (101) |
| Comb 129 | 2-ethylhexyl 4-methoxy-cinnamate; octyl methoxy cinnamate | 2-Ethylhexyl 2-cyano,3,3-diphenylacrylate; octocrylene | micronized UV absorber of formula (101) |
| Comb 130 | 2-ethylhexyl 4-methoxy-cinnamate; octyl methoxy cinnamate | Benzoic acid, 4,4',4"-(1,3,5-triazine-2,4,6-triyltriimino)tris-, tris(2-ethylhexyl)ester; 2,4,6-Trianilino-(p-carbo-2'-ethyl-hexyl-1'-oxi)-1,3,5-triazine; octyl triazone | micronized UV absorber of formula (101) |
| Comb 131 | 2-ethylhexyl 4-methoxy-cinnamate; octyl methoxy cinnamate | 2-phenyl-1H-benzimidazole-5-sulphonic acid; phenylbenz-imidazolsulfonic acid | micronized UV absorber of formula (101) |
| Comb 132 | 2-ethylhexyl 4-methoxy-cinnamate; octyl methoxy cinnamate | 1-[4-(1,1-dimethylethyl)phenyl]-3-(4-methoxyphenyl)-propane-1,3-dione; avobenzone | micronized UV absorber of formula (101) |
| Comb 133 | 2-ethylhexyl 4-methoxy-cinnamate; octyl methoxy cinnamate | Phenol, 2-(2H-benzotriazol-2-yl)-4-methyl-6-[2-methyl-3-[1,3,3,3-tetramethyl-1-[(trimethylsilyl)oxy]disiloxanyl]propyl]-; drometrizole trisiloxane; Mexoryl XL | micronized UV absorber of formula (101) |
| Comb 134 | 2-ethylhexyl 4-methoxycinnamate; octyl methoxy cinnamate | Dimethicodiethylbenzalmalonate; Polysilicone 15; Parsol SLX | micronized UV absorber of formula (101) |
| Comb 135 | 2-ethylhexyl 4-methoxy-cinnamate; octyl methoxy cinnamate | 2,2'-Methylene-bis-[6-(2H-benzotriazol-2-yl)-4-(1,1,3,3-tetramethylbutyl)-phenol]; Tinosorb M | micronized UV absorber of formula (101) |
| Comb 136 | 2-ethylhexyl 4-methoxy-cinnamate; octyl methoxy cinnamate | 2,4-bis{[4-(2-ethylhexyloxy)-2-hydroxy]-phenyl}-6-(4-methoxyphenyl)-(1,3,5)-triazine; Tinosorb S | micronized UV absorber of formula (101) |
| Comb 137 | 2,4-bis{[4-(2-ethylhexyloxy)-2-hydroxy]-phenyl}-6-(4-methoxyphenyl)-(1,3,5)-triazine; Tinosorb S | 2,2'-Methylene-bis-[6-(2H-benzotriazol-2-yl)-4-(1,1,3,3-tetramethylbutyl)-phenol]; Tinosorb M | micronized UV absorber of formula (101) |
| Comb 138 | Benzoic acid, 2-[4-(diethyl-amino)-2-hydroxybenzoyl]-, hexyl ester; Uvinul a plus | 1-[4-(1,1-dimethylethyl)phenyl]-3-(4-methoxyphenyl)-propane-1,3-dione; avobenzone | micronized UV absorber of formula (101) |
| Comb 139 | 2,4-bis{[4-(2-ethylhexyloxy)-2-hydroxy]-phenyl}-6-(4-methoxyphenyl)-(1,3,5)-triazine; Tinosorb S | 1-[4-(1,1-dimethylethyl)phenyl]-3-(4-methoxyphenyl)propane-1,3-dione; avobenzone | micronized UV absorber of formula (101) |
| Comb 140 | 1-[4-(1,1-dimethylethyl)-phenyl]-3-(4-methoxy-phenyl)propane-1,3-dione; avobenzone | 2,2'-bis(1,4-phenylene)-1H-benzimidazole-4,6-disulphonic acid mono sodium salt or Disodium phenyl dibenzimidazole tetrasulfonate or Neoheliopan AP | micronized UV absorber of formula (101) |

The compounds of formula (1) can be prepared according to known methods as described for example in U.S. Pat. No. 6,225,467.

Furthermore, the compounds of formula (1) may be obtained in a Grignard reaction starting from the corresponding halogen aromatic compounds and a trihalogen triazine.

The cyclotrimerisation of aromatc nitrilic compounds is a further well method for the preparation of symmetrical triazine derivatives of formula (1) achieving minor yields.

Surprisingly a simple method for the preparation of the compounds of formula (1) was found. The reaction of trihalogen-1,3,5-triazines with aromatic compounds in a Friedel-Crafts-reaction delivers high yields of symmetrical triazine derivatives. Suitable aromatic compounds are:

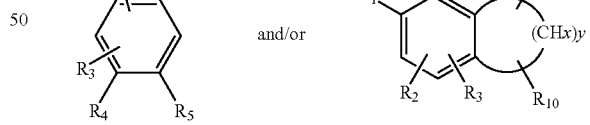

wherein $R_1$-$R_{10}$ are defined as in formula (1).

According to this method the compound of formula (101) can be prepared according to the following reaction scheme:

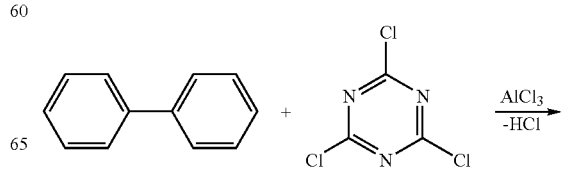

-continued

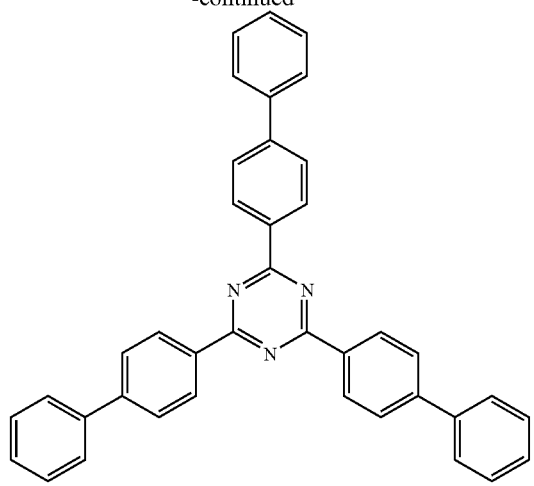

Cyanuric chloride is preferably used as trihalogen-1,3,5-triazine.

The reaction temperature is from −10 to 250° C., preferably from 5-150° C., most preferably from 70-130° C.

Classes of compounds that can be used as catalyst are listed in the table below:

| | |
|---|---|
| Acidic halides | AlCl$_3$, AlBr$_3$, SnCl$_4$, SbCl$_5$, FeCl$_3$ |
| Metal alkyls and alkoxides | AlR$_3$, BR$_3$, ZnR$_2$, Al(OPh)$_3$ |
| Proton acids | HCl, HCl—AlCl$_3$, H$_2$SO$_4$, HF, H$_3$PO$_4$ |
| Acidic oxides and derivatives | zeolites, mixed oxides and solid superacids, clays, heteropolyacids, modified clays |
| Supported acids | H$_3$PO$_4$—SiO$_2$, BF$_3$—Al$_2$O$_3$ |
| Cation-exchange resins | Permutit Q, Amberlite IR 112, Dowex 50, Nafion-silica, Deloxan |
| Other catalysts | Solid superacids, , Heteropolyacids, , Proton or Lewis acids on a support, Nafion and Nafion like composites |

Preferred catalysts are (as single compounds or in combination: AlCl$_3$, AlBr$_3$, BF$_3$, BCl$_3$, BBr$_3$, BeCl$_2$, CdCl$_2$, ZnCl$_2$, GaCl$_3$, GaBr$_3$, FeCl$_3$, SbCl$_3$, BiCl$_3$, TiCl$_4$, ZrCl$_4$, SnCl$_4$, UCl$_4$ and SbCl$_5$.

Advantageously the compounds listed in the table above are used in stoichiometric amounts or in excess.

As co-catalysts are used: alcohols, water, HCl, HF, H$_2$SO$_4$, H$_3$PO$_4$, RCOOH (organic acids), sulfonic acids like for example p-toluene sulfonic acid.

The co-catalysts can also be used in stoichiometric amounts or in excess.

Preferably gaseus HCl is used as co-catalyst.

As catalysts, co-catalysts or promotors compounds or classes of compounds are used:

Cations forming compounds: preferred are alkyl- and acyl-halogenides as well as compounds comprising oxygen-, sulfur-, or halogen-donor atoms.

Adducts: ZnCl$_2$—AlCl$_3$, SnCl$_4$, AlCl$_3$-ketones, AlCl$_3$-Pyridine, AlCl$_3$—RNO$_2$, AlBr$_3$—RNO$_2$, GaCl$_3$—RNO$_2$, SbF$_5$, BF$_3$—OEt$_2$, BF$_3$—C$_6$H$_5$OH; AlCl$_3$-Sulfolane. (R—NO$_2$: nitroaliphatic and nitroaromatic compounds).

Suitable solvents are: aliphatic hydrocarbons, aromatic hydrocarbons, sulfur-hydrocarbons, halogenaromatic compounds, halogenaliphatic compounds, alyl-aryl ethers, alkyl-alkyl ethers, sulfolane, nitroaromatic compounds and nitroaliphatic compounds.

Mostly preferred are: chlorbenzene, 1,2-dichlorbenzene, 1,4-dichlorbenzene, nitrobenzene, nitromethane, tetrachlormethane.

Furthermore, the reaction can be carried out in ionic fluids like for example 1-butylpyridiniume chloride-aluminum(III) chloride and 1-butyl-3-methylimidazolium chloride-aluminum(III) chloride (s. 1-ethyl-3-methylimidazolium halogenoaluminate ionic liquids as solvents for Friedel-Crafts acylation reactions of ferrocene. Journal of the Chemical Society, Dalton Transactions: Inorganic Chemistry 1999 (1), 63).

Surprisingly it was found that the reaction can be carried out in absence of a solvent like 1,2-dichlorobenzene. The reaction runs particularly well when gaseous HCl is discharged into the reaction mixture.

This preparation process has specific significance since the use of halogenated aromatic solvents causes residues of solvents which are only difficult to remove in the end product. These kinds of solvents are inappropriate for cosmetic applications.

The cosmetic or pharmaceutical preparations may be, for example, creams, gels, lotions, alcoholic and aqueous/alcoholic solutions, emulsions, wax/fat compositions, stick preparations, powders or ointments. In addition to the above mentioned UV filters, the cosmetic or pharmaceutical preparations may contain further adjuvants as described below.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight und preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic or pharmaceutical compositions/preparations according to the invention may also contain one or one more additional compounds as described below.

Fatty Alcohols

Guerbet alcohols based on fatty alcohols having from 6 to 18, preferably from 8 to 10 carbon atoms including cetyl alcohol, stearyl alcohol, cetearyl alcohol, oleyl alcohol, octyl-dodecanol, benzoate of C12-C15 alcohols, acetylated lanolin alcohol, etc.

Esters of Fatty Acids

Esters of linear C$_6$-C$_{24}$ fatty acids with linear C$_3$-C$_{24}$ alcohols, esters of branched C$_6$-C$_{13}$carboxylic acids with linear C$_6$-C$_{24}$ fatty alcohols, esters of linear C$_6$-C$_{24}$ fatty acids with branched alcohols, especially 2-ethylhexanol, esters of hydroxycarboxylic acids with linear or branched C$_6$-C$_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols).

Examples of such ester oils are isopropylmyristate, isopropylpalmitate, isopropylstearate, iso-propyl isostea rate, isopropyloleate, n-butylstea rate, n-hexyllau rate, n-decyloleate, isooctyl-stearate, iso-nonylstearate, isononyl isononanoate, 2-ethylhexylpalmitate, 2-hexyllaurate, 2-hexyldecylstearate, 2-octyldodecylpalmitate, oleyloleate, oleylerucate, erucyloleate, erucyl-erucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

Other Adjuvants alpha glucosylrutin (CAS No. 130603-71-3), 2-butyloctyl o-hydroxybenzoate (CAS No. 190085-41-7), vitamin E (CAS No. 1406-184), vitamin E acetate (CAS No. 58-95-7), diethylhexyl 2,6-naphthalate, di-n-butyl adipate, di(2-ethylhexyl)-adipate, di(2-ethylhexyl)-succinate and diisotridecyl acelaat, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Esters of $C_6$-$C_{24}$ fatty alcohols and/or Guerbet alcohols with aromatic carboxylic acids, saturated and/or unsaturated, especially benzoic acid, esters of $C_2$-$C_{12}$dicarboxylic acids with linear or branched alcohols having from 1 to 22 carbon atoms or polyols having from 2 to 10 carbon atoms and from 2 to 6 hydroxy groups, or iminodisuccinic acid and imiondisuccinic acid salts [CAS 7408-20-0] or latex particles, aloe vera, chamomile, ginko biloba, ginseng, coenzyme Q10, laminaria ochroleuca extract, magnolia oborata extract, melalenca alternifolia leaf oil, rubus idaeus seed oil, vaccinium macrocarpon seed oil, pumpkin seed extract, pumpkin seed oil, grape seed extract, carnosine, alpha-arbutin, madecassoside, termino-laside, tetrahydrocurcuminoids (THC), mycosporines, mycosporine like amino acids from the red alga porphyra umbilicalis, mycosporine-like amino acids (as described in WO2002039974), cis-9-octadecenedioic acid, lipoic acid, laurimino dipropiomic acid tocopheryl phosphates (LDTP), microcrystalline cellulose (MCC), polycarbonates as described in WO 0341676, sterols (cholesterol, lanosterol, phytosterols), as described in WO0341675 and linear poly-alpha-glucans as described in U.S. Pat. No. 6,616,935.

Natural or Synthetic Triglycerides Including Glyceryl Esters and Derivatives

Di- or tri-glycerides, based on $C_6$-$C_{18}$ fatty acids, modified by reaction with other alcohols (caprylic/capric triglyceride, wheat germ glycerides, etc.). Fatty acid esters of polyglycerin (polyglyceryl-n such as polyglyceryl4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, macadamia nut oil, olive oil, hydrogenated tallow, apricot kernel oil, hazelnut oil, borago oil, etc.

Waxes including esters of long-chain acids and alcohols as well as compounds having wax-like properties, e.g., carnauba wax, beeswax (white or yellow), lanolin wax, candellila wax, ozokerite, japan wax, paraffin wax, microcrystalline wax, ceresin, cetearyl esters wax, synthetic beeswax,etc. Also, hydrophilic waxes as Cetearyl Alcohol or partial glycerides.

Pearlescent Waxes:

Ikylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Hydrocarbon Oils:

Mineral oil (light or heavy), petrolatum (yellow or white), microcrystalline wax, paraffinic and isoparaffinic compounds, hydrogenated isoparaffinic molecules as polydecenes and polybutene, hydrogenated polyisobutene, squalane, isohexadecane, isododecane and others from plant and animal kingdom.

Silicones or Siloxanes (Organosubstituted Polysiloxanes)

Dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear poly-siloxanes, dimethicone (Dow Corning 200 fluid, Rhodia Mirasil DM), dimethiconol, cyclic silicone fluids, cyclopentasiloxanes volatiles (Dow Corning 345 fluid), phenyltrimethicone (Dow Corning 556 fluid). Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Fluorinated or Perfluorinated Oils

Perfluorhexane, dimethylcyclohexane, ethylcyclopentane, polyperfluoromethylisopropyl ether.

Emulsifiers

Any conventionally usable emulsifier can be used for the compositions. Emulsifier systems may comprise for example: carboxylic acids and their salts: alkaline soap of sodium, potassium and ammonium, metallic soap of calcium or magnesium, organic basis soap such as Lauric, palmitic, stearic and oleic acid etc. Alkyl phosphates or phosphoric acid esters, acid phosphate, diethanolamine phosphate, potassium cetyl phosphate. Ethoxylated carboxylic acids or polyethyleneglycol esters, PEG-n acylates. Linear fatty alcohols having from 8 to 22 carbon atoms, branched from 2 to 30 mol of ethylene oxide and/or from 0 to 5 mol propylene oxide with with fatty acids having from 12 to 22 carbon atoms and with alkylphenols having from 8 to 15 carbon atoms in the alkyl group. Fatty alcohol polyglycolether such as laureth-n, ceteareth-n, steareth-n, oleth-n. Fatty acid polyglycolether such as PEG-n stearate, PEG-n oleate, PEG-n cocoate. Monoglycerides and polyol esters. C12-C22 fatty acid mono- and di-esters of addition products of from 1 to 30 mol of ethylene oxide with polyols. Fatty acid and polyglycerol ester such as monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as monostearate diethylene glycol, fatty acid and polyethylene glycol esters, fatty acid and saccharose esters such as sucro esters, glycerol and saccharose esters such as sucro glycerides. Sorbitol and sorbitan, sorbitan mono- and di-esters of saturated and unsaturated fatty acids having from 6 to 22 carbon atoms and ethylene oxide addition products. Polysorbate-n series, sorbitan esters such as sesquiisostearate, sorbitan, PEG-(6)-isostearate sorbitan, PEG-(10)-sorbitan laurate, PEG-17-dioleate sorbitan. Glucose derivatives, C8-C22 alkyl-mono and oligo-glycosides and ethoxylated analogues with glucose being preferred as the sugar component. O/W emulsifiers such as methyl gluceth-20 sesquistearate, sorbitan stearate/sucrose cocoate, methyl glucose sesquistearate, cetearyl alcohol/cetearyl glucoside. W/O emulsifiers such as methyl glucose dioleate/methyl glucose isostearate. Sulfates and sulfonated derivatives, dialkylsulfosuccinates, dioctyl succinate, alkyl lauryl sulfonate, linear sulfonated parafins, sulfonated tetraproplyne sulfonate, sodium lauryl sulfates, amonium and ethanolamine lauryl sulfates, lauyl ether sulfates, sodium laureth sulfates, sulfosuccinates, aceyl isothionates, alkanolamide sulfates, taurines, methyl taurines, imidazole sulfates. Amine derivatives, amine salts, ethoxylated amines, oxide amine with chains containing an heterocycle such as alkyl imidazolines, pyridine derivatives, isoquinoteines, cetyl pyridinium chlorure, cetyl pyridinium bromide, quaternary ammonium such as cetyltrimethyl-broide amonium broide (CTBA), stearylalkonium. Amide derivatives, alkanolamides such as acylamide DEA, ethoxylated amides such as PEG-n acylamide, oxydeamide. Polysiloxane/polyalkyl/polyether copolymers and derivatives, dimethicone, copolyols, silicone polyethylene oxide copolymer, silicone glycol copolymer. Propoxylated or POE-n ethers (Meroxapols), Polaxamers or poly(oxyethylene)m-block-poly(oxypropylene)n-block(oxyethylene). Zwitterionic surfactants that carry at least one quaternary ammonium group and at least one carboxylate and/or sulfonate group in the molecule. Zwitterionic surfactants that are especially suitable are betaines, such as N-alkyl-N,N-dimethylammonium glycinates, cocoalkyldimethylammonium glycinate, N-acylamino-propyl-N,N-dimethylammonium glycinates, cocoacylaminopropyidimethylammonium glycinate and 2-alkyl-3-carboxymethyl-3-hydroxyethylimidazolines each having from 8 to 18 carbon atoms in the alkyl or acyl group and also cocoacylaminoethylhydroxyethylcarboxy-methylglycinate, N-alkylbetaine, N-alkylaminobetaines. Alkylimidazolines, alkylopeptides, lipoaminoacides, self emulsifying bases and the compounds as described in K. F. DePolo, A short textbook of cosmetology, Chapter 8, Table 8-7, p250-251.

Non ionic emulsifiers such as PEG-6 beeswax (and) PEG-6 stearate (and) polyglyceryl-2-iso-stearate [Apifac], glyceryl stearate (and) PEG-100 stearate. [Arlacel 165], PEG-5 glyceryl stearate [arlatone 983 S], sorbitan oleate (and) polyglyceryl-3 ricinoleate.[Arlacel 1689], sorbitan stearate and sucrose cocoate [arlatone 2121], glyceryl stearate and laureth-23 [Cerasynth 945], cetearyl alcohol and ceteth-20 [Cetomacrogol Wax], cetearyl alcohol and colysorbate 60 and PEG-150 and stearate-20[Polawax GP 200, Polawax NF], cetearyl alcohol and cetearyl polyglucoside [Emulgade PL 1618], cetearyl alcohol and ceteareth-20 [Emulgade 1000NI, Cosmowax], cetearyl alcohol and PEG40 castor oil [Emulgade F Special], cetearyl alcohol and PEG-40 castor oil and sodium cetearyl sulfate [Emulgade F], stearyl alcohol and steareth-7 and steareth-10 [Emulgator E 2155], cetearyl alcohol and szareth-7 and steareth-10 [Emulsifying wax U.S.N.F], glyceryl stearate and PEG-75 stearate [Gelot 64], propylene glycol ceteth-3 acetate [Hetester PCS], propylene glycol isoceth-3 acetate [Hetester PHA], cetearyl alcohol and ceteth-12 and oleth-12 [Lanbritol Wax N 21], PEG-6 stearate and PEG-32 stearate [Tefose 1500], PEG-6 stearate and ceteth-20 and steareth-20 [Tefose 2000], PEG-6 stearate and ceteth-20 and glyceryl stearate and steareth-20 [Tefose 2561], glyceryl stearate and ceteareth-20 [Teginacid H, C, X].

Anionic emulsifiers such as PEG-2 stearate SE, glyceryl stearate SE [Monelgine, Cutina K D], propylene glycol stearate [Tegin P], cetearyl Alcohol and Sodium cetearyl sulfate [Lanette N, Cutina L E, Crodacol G P], cetearyl alcohol and sodium lauryl sulfate [Lanette W], trilaneth-4 phopshate and glycol stearate and PEG-2 stearate [Sedefos 75], glyceryl stearate and sodium lauryl Sulfate [Teginacid Special]. Cationic acid bases such as cetearyl alcohol and cetrimonium bromide.

The emulsifiers may be used in an amount of, for example, from 1 to 30% by weight, especially from 4 to 20% by weight and preferably from 5 to 10% by weight, based on the total weight of the composition.

When formulated in O/W emulsions, the preferably amount of such emulsifier system could represent 5% to 20% of the oil phase.

Adjuvants and Additives

The cosmetic/pharmaceutical preparations, for example creams, gels, lotions, alcoholic and aqueous/alcoholic solutions, emulsions, wax/fat compositions, stick preparations, powders or ointments, may in addition contain, as further adjuvants and additives, mild surfactants, super-fatting agents, consistency regulators, thickeners, polymers, stabilisers, biogenic active ingredients, deodorising active ingredients, anti-dandruff agents, film formers, swelling agents, further UV light-protective factors, antioxidants, hydrotropic agents, preservatives, insect repellents, self-tanning agents, solubilisers, perfume oils, colourants, bacteria-inhibiting agents and the like.

Super-fatting Agents

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Surfactants

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ethercarboxylic acids, alkyl oligoglucosides, fatty acid glucamides, alkylamidobetaines and/or protein fatty acid condensation products, the latter preferably being based on wheat proteins.

Consistency Regulators/Thickeners and Rheology Modifiers

Silicium dioxide, magnesium silicates, aluminium silicates, polysaccharides or derivatives thereof for example hyaluronic acid, xanthan gum, guar-guar, agar-agar, alginates, carraghenan, gellan, pectines, or modified cellulose such as hydroxycellulose, hydroxypropyl-methylcellulose. In addition polyacrylates or homopolymer of reticulated acrylic acids and polyacrylamides, carbomer (carbopol types 980, 981, 1382, ETD 2001, ETD2020, Ultrez 10) or Salcare range such as Salcare SC80(steareth-10 allyl ether/acrylates copolymer), Salcare SC81 (acrylates copolymer), Salcare SC91 and Salcare AST(sodium acrylates copolymer/PPG-1 trideceth-6), sepigel 305(polyacrylamide/laureth-7), Simulgel NS and Simulgel EG (hydroxyethyl acrylate/sodium acryloyldimethyl taurate copolymer), Stabilen 30 (acrylates/vinyl isodecanoate crosspolymer), Pemulen TR-1 (acrylates/C10-30 alkyl acrylate crosspolymer), Luvigel EM (sodium acrylates copolymer), Aculyn 28 (acrylates/beheneth-25 methacrylate copolymer), etc.

Polymers

Suitable cationic polymers are, for example, cationic cellulose derivatives, for example a quaternised hydroxymethyl cellulose obtainable under the name Polymer JR 400 from Amerchol, cationic starches, copolymers of diallylammonium salts and acrylamides, quarternised vinylpyrrolidone/vinyl imidazole polymers, for example Luviquat® (BASF), condensation products of polyglycols and amines, quaternised collagen polypeptides, for example lauryldimonium hydroxypropyl hydrolyzed collagen (Lamequat®L/Grünau), quaternised wheat polypeptides, polyethyleneimine, cationic silicone polymers, for example amidomethicones, copolymers of adipic acid and dimethylaminohydroxypropyldiethylenetriamine (Cartaretin/Sandoz), copolymers of acrylic acid with dimethyldiallylammonium chloride (Merquat 550/Chemviron), polyaminopolyamides, as described, for example, in FR-A-2 252 840, and the crosslinked water-soluble polymers thereof, cationic chitin derivatives, for example of quaternised chitosan, optionally distributed as microcrystals; condensation products of dihaloalkyls, for example dibromobutane, with bisdialkylamines, for example bisdimethylamino-1,3-propane, cationic guar gum, for example Jaguar C-17, Jaguar C-16 from Celanese, quaternised ammonium salt polymers, for example Mirapol A-15, Mirapol AD-1, Mirapol AZ-1 from Miranol. As anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyl-trimethyl-ammonium chloride /acrylate copolymers, octyl acrylamide/methyl methacrylate-tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatised cellulose ethers and silicones. Furthermore the polymers as described in EP 1093796 (pages 3-8, paragraphs 17-68) may be used.

Biogenic Active Ingredients

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Deodorising Active Ingredients

As deodorising active ingredients there come into consideration, for example, anti-perspirants, for example aluminium chlorohydrates (see J. Soc. Cosm. Chem. 24, 281 (1973)). Under the trade mark Locron® of Hoechst AG, Frankfurt (FRG), there is available commercially, for example, an aluminium chlorohydrate corresponding to formula $Al_2(OH)_5Cl \times 2.5\ H_2O$, the use of which is especially preferred (see J. Pharm. Pharmacol. 26, 531 (1975)). Besides the chlorohydrates, it is also possible to use aluminium hydroxyacetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen CAT, Henkel), which inhibit enzyme activity and hence reduce odour formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the germ flora and kill or inhibit the growth of sweat-decomposing bacteria can likewise be present in the preparations (especially in stick preparations). Examples include chitosan, phenoxyethanol and chlor-hexidine gluconate. 5-chloro-2-(2,4-dichlorophenoxy)-phenol (Triclosan, Irgasan, Ciba Specialty Chemicals Inc.) has also proved especially effective.

Anti-dandruff Agents

As anti-dandruff agents there may be used, for example, climbazole, octopirox and zinc pyrithione. Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

Antioxidants

In addition to the primary light-protective substances it is also possible to use secondary light-protective substances of the antioxidant kind that interrupt the photochemical reaction chain triggered when UV radiation penetrates the skin or hair. Typical examples of such anti-oxidants are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes, lycopene and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine), also (metal) chelating agents (e.g. hydroxy fatty acids, palmitic acid phytic acid, lactoferrin), hydroxy acids (e.g. citric acid, lactic acid, malic acid), humic acid, bile acid, bile extracts, bilirubin, biliverdin, EDTA, EDDS, EGTA and derivatives thereof, unsaturated fatty acids and derivatives thereof (e.g. linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, glycosylrutin, ferulic acid, furfurylidene glucitol, carnosine, butyl hydroxytoluene, butyl hydroxyanisole, nordihydroguaiaretic acid, trihydroxybutyrophenone, uric acid and derivatives thereof, mannose and derivatives thereof, superoxide dismutase, N-[3-(3,5-di-tert-butyl-4-hydroxy-phenyl)propionyl]sulfanilic acid (and salts thereof, for example the disodium salts), zinc and derivatives thereof (e.g. ZnO, $ZnSO_4$), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. HALS (="Hindered Amine Light Stabilizers") compounds may also be mentioned.

Further synthetic and natural antioxidants are listed e.g. in patent WO 0025731: Structures 1-3 (page 2), structure 4 (page 6), structures 5-6 (page 7) and compounds 7-33 (page 8-14).

The amount of antioxidants present is usually from 0.001 to 30% by weight, preferably from 0.01 to 3% by weight, based on the weight of the UV absorber of formula (1).

Hydrotropic Agents

To improve the flow behaviour it is also possible to employ hydrotropic agents, for example ethoxylated or non ethoxylated mono-alcohols, diols or polyols with a low number of carbon atoms or their ethers (e.g. ethanol, isopropanol, 1,2-dipropanediol, propyleneglycol, glyerin, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols that come into consideration for that purpose have preferably from 2 to 15 carbon atoms and at least two hydroxy groups. The polyols may also contain further functional groups, especially amino groups, and/or may be modified with nitrogen. Typical examples are as follows: glycerol, alkylene glycols, for example ethylene glycol, diethylene glycol, propylene glycol, butylene glycol, hexylene glycol and also polyethylene glycols having an average molecular weight of from 100 to 1000 Dalton; technical oligoglycerol mixtures having an intrinsic degree of condensation of from 1.5 to 10, for example technical diglycerol mixtures having a diglycerol content of from 40 to 50% by weight; methylol compounds, such as, especially, trimethylolethane, trimethylol-propane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanolamine or 2-amino-1,3-propanediol.

Preservatives and Bacteria-inhibiting Agents

Suitable preservatives include, for example,Methyl-, Ethyl-, Propyl-, Butyl-parabens, Benzal-konium chloride, 2-Bromo-2-nitro-propane-1,3-diol, Dehydroacetic acid, Diazolidinyl Urea, 2-Dichloro-benzyl alcohol, DMDM hydantoin, Formaldehyde solution, Methyldibromoglutanitrile, Phenoxyethanol, Sodium Hydroxymethylglycinate, Imidazolidinyl Urea, Triclosan and further substance classes listed in the following reference: K. F. DePolo—A short textbook of cosmetology, Chapter 7, Table 7-2, 7-3, 7-4 and 7-5, p210-219.

Bacteria-inhibiting Agents

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-tri-methyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations.

Perfume Oils

There may be mentioned as perfume oils mixtures of natural and/or synthetic aromatic substances. Natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type. Aromatic substance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the iononones, isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

Colourants

There may be used as colourants the substances that are suitable and permitted for cosmetic purposes, as compiled, for example, in the publication "Kosmetische Farbemittel" of the Farbstoffkommission der Deutschen Forschungsgemeinschaft, Verlag Chemie, Weinheim, 1984, pages 81 to 106. The colourants are usually used in concentrations of from 0.001 to 0.1% by weight, based on the total mixture.

Other Adjuvants

It is furthermore possible for the cosmetic preparations to contain, as adjuvants, anti-foams, such as silicones, structurants, such as maleic acid, solubilisers, such as ethylene glycol, propylene glycol, glycerol or diethylene glycol, opacifiers, such as latex, styrene/PVP or styrene/acrylamide copolymers, complexing agents, such as EDTA, NTA, alaninediacetic acid or phosphonic acids, propellants, such as propane/butane mixtures, $N_2O$, dimethyl ether, $CO_2$, $N_2$ or air, so-called coupler and developer components as oxidation dye precursors, reducing agents, such as thioglycolic acid and derivatives thereof, thiolactic acid, cysteamine, thiomalic acid or mercaptoethanesulfonic acid, or oxidising agents, such as hydrogen peroxide, potassium bromate or sodium bromate.

Suitable insect repellents are, for example, N,N-diethyl-m-toluamide, 1,2-pentanediol or insect repellent 3535; suitable self-tanning agents are, for example, dihydroxyacetone and/or erythrulose or dihydroxy acetone and/or dihydroxy acetone precursors as described in WO 01/85124 and/or erythrulose.

Polymeric Beads or Hollow Spheres as SPF Enhancers

The combination of the UV-absorbers and UV-absorber combinations, listed above, with SPF enhancers, such as non-active ingredients like Styrene/acrylates copolymer, silica beads, spheroidal magnesium silicate, crosslinked Polymethylmethacrylates (PMMA; Micopearl M305 Seppic), can maximize better the UV protection of the sun products. Holosphere additives (Sunspheres® ISP, Silica Shells Kobo.) deflect radiation and the effective path length of the photon is therefore increased.(EP0893119). Some beads, as mentioned previously, provide a soft feel during spreading. Moreover, the optical activity of such beads, e.g.Micropearl M305, cans modulate skin shine by eliminating reflection phenomena and indirectly may scatter the UV light.

Cosmetic or Pharmaceutical Preparations

Cosmetic or pharmaceutical formulations are contained in a wide variety of cosmetic preparations. There come into consideration, for example, especially the following preparations:

skin-care preparations, e.g. skin-washing and cleansing preparations in the form of tablet-form or liquid soaps, soapless detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

Presentation Forms

The final formulations listed may exist in a wide variety of presentation forms, for example:
in the form of liquid preparations as a W/O, O/W, O/W/O, W/O/W or PIT emulsion and all kinds of microemulsions,
in the form of a gel,
in the form of an oil, a cream, milk or lotion,
in the form of a powder, a lacquer, a tablet or make-up,
in the form of a stick,
in the form of a spray (spray with propellent gas or pump-action spray) or an aerosol,
in the form of a foam, or
in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber according to the invention, 12.0% by weight of sodium laureth-2-sulfate, 4.0% by weight of cocamidopropyl betaine, 3.0% by weight of sodium chloride, and water ad 100%.

For example, especially the following hair-cosmetic formulations may be used:

$a_1$) spontaneously emulsifying stock formulation, consisting of the UV absorber according to the invention, PEG-6-$C_{10}$oxoalcohol and sorbitan sesquioleate, to which water and any desired quaternary ammonium compound, for example 4% minkamidopropyl di-methyl-2-hydroxyethylammonium chloride or Quaternium 80 is added;

$a_2$) spontaneously emulsifying stock formulation consisting of the UV absorber according to the invention, tributyl citrate and PEG-20-sorbitan monooleate, to which water and any desired quaternary ammonium compound, for example 4% minkamidopropyl dimethyl-2-hydroxyethylammonium chloride or Quaternium 80 is added;

b) quat-doped solutions of the UV absorber according to the invention in butyl triglycol and tributyl citrate;

c) mixtures or solutions of the UV absorber according to the invention with n-alkylpyrrolidone.

Other typical ingredients in such formulations are preservatives, bactericides and bacteriostatic agents, perfumes, dyes, pigments, thickening agents, moisturizing agents, humectants, fats, oils, waxes or other typical ingredients of cosmetic and personal care formulations such as alcohols, poly-alcohols, polymers, electrolytes, organic solvents, silicon derivatives, emollients, emulsifiers or emulsifying surfactants, surfactants, dispersing agents, antioxidants, anti-irritants and anti-inflammatory agents etc.

Examples of Cosmetic and Pharmaceutical Preparations (X=Preferred Combinations)

| Ingredients | O/W systems: | | | | | | | |
|---|---|---|---|---|---|---|---|---|
| | 1 | 2 | 3 | 4 | 5 | 6 | 7 | 8 |
| Emulsifiers | | | | | | | | |
| Potassium Cetyl Phosphate 2%-5% | X | | | | | | | |
| Cetearyl Alcohol/Dicetyl Phosphate/Ceteth-10 Phosphate 2%-6% | | X | | | | | | |
| Sodium Stearyl Phtalamate 1%-2% | | | X | | | | | |
| Cetearyl Alcohol/Behentrimonium Methosulfate 1%-5% | | | | X | | | | |
| Quaternium-32 1%-5% | | | | | X | | | |
| Dimethicone copolyol/Caprylic/Capric Triglyceride (1%-4%) | | | | | | X | | |
| Steareth-2/Steareth-21 2%-5% | | | | | | | X | |
| Polyglyceryl Methyl Glucose Distearate 1%-4% | | | | | | | | X |
| Lipophilic emollient/dispersant oil 15%-20% | X | X | X | X | X | X | X | X |
| Fatty Alcohols and/or Waxes 1%-5% | X | X | X | X | X | X | X | X |
| Thickeners (water swellable thickeners) 0.5%-1.5% | X | X | X | X | X | X | X | X |
| Preservatives 0.5%-1% | X | X | X | X | X | X | X | X |
| Chelating agents (such as EDTA) 0%-0.2% | X | X | X | X | X | X | X | X |
| Antioxidants 0.05%-0.2% | X | X | X | X | X | X | X | X |
| Water deionized Qs 100% | X | X | X | X | X | X | X | X |
| Perfume oils 0.1%-0.4% | X | X | X | X | X | X | X | X |
| UV-absorber according to the invention 0.1%-20% | X | X | X | X | X | X | X | X |
| UV-absorber as described in table 1-3 0%-30% | X | X | X | X | X | X | X | X |

| W/O systems Ingredients | 1 | 2 | 3 | 4 | 5 |
|---|---|---|---|---|---|
| Emulsifiers | X | X | X | X | X |
| Polyglyceryl-2 Dipolyhydroxystearate 2%-4% | X | X | X | X | X |
| PEG-30 Dipolyhydroxystearate 2%-4% | | X | | | |
| Rapeseed Oil Sorbitol Esters 1%-5% | | | X | | |
| PEG-45/Dodecyl Glycol Copolymer 1%-5% | | | | X | |
| Sorbitan Oleate/Polycerol-3 ricinoleate 1%-5% | | | | | X |
| Lipophilic emollient/dispersant oil 10%-20% | X | X | X | X | X |
| Fatty Alcohols and/or Waxes 10%-15% | X | X | X | X | X |
| Electrolytes (NaCl, MgSO$_4$) 0.5%-1% | X | X | X | X | X |
| Polyol phase (Propylene glycol, glycerin) 1%-8% | X | X | X | X | X |
| Preservatives 0.3%-0.8% | X | X | X | X | X |
| Perfume oils 0.1%-0.4% | X | X | X | X | X |
| Chelating agents (such as EDTA) 0%-0.2% | X | X | X | X | X |
| Antioxidants 0.05%-0.2% | X | X | X | X | X |
| Water deionized Qs 100% | X | X | X | X | X |
| UV-absorber according to the invention 0.1%-20%. | X | X | X | X | X |
| UV-absorber as described in table 1-3 0%-30%. | X | X | X | X | X |

| W/Silicone systems Ingredients | 1 | 2 | 3 | 4 |
|---|---|---|---|---|
| Dimethicone Copolyol/Cyclomethicone 5%-10% | X | | X | |
| Laurylmethicone Copolyol 5%-10% | | X | | X |
| Cyclopentasiloxane 15%-25% | X | | | X |
| Dimethicone 15%-25% | | | X | X |
| Dimethicone/Vinyldimethicone Crosspolymer 1%-10% | X | X | X | X |
| Humectant/polyols (Propylene glycol, glycerin . . . ) 2%-8% | X | X | X | X |
| Chelating agents (such as EDTA) 0%-0.2% | X | X | X | X |
| Antioxidants 0.05%-0.2% | X | X | X | X |
| Preservatives 0.3%-0.8% | X | X | X | X |
| Perfume oils 0.1%-0.4% | X | X | X | X |
| Water deionized Qs 100% | X | X | X | X |
| UV-absorber according to the invention 0.1%-20% | X | X | X | X |
| UV-absorber as described in table 1-3 0%-30% | X | X | X | X |

| Multiple emulsions Ingredients | 1 | 2 | 3 | 4 | 5 | 6 | 7 | 8 | 9 | 10 | 11 | 12 |
|---|---|---|---|---|---|---|---|---|---|---|---|---|
| PEG-30 Dipolyhydroxystearate (2%-6%) | X | | | | | | | | | X | | X |
| Cetyl Dimethicone Copolyol 1%-3% | | X | | | | | | X | | | | |
| PEG-30 Dipolyhydroxystearate/ Steareth-2/Steareth-21 4%-6% | | | X | | | X | | | | | | |
| Polyglyceryl-2 Dipolyhydroxy-stearate 1%-3% | | | | X | | | X | | | | | |
| Polyglyceryl-6 Ricinoleate 1%-3% | | | | | X | X | | | | | X | |
| Oil phase 15%-30% | | | | | | | | | | | | |
| Fatty acid esters | X | X | X | X | X | | | | | | X | X |
| Natural and synthetic Triglycerides | | | | | | X | X | X | X | X | X | X |
| Hydrocarbon oils | X | X | X | X | X | | | | | | X | X |
| Silicone oils | | | | | | X | X | X | X | X | X | X |
| Preservatives 0.3%-0.8% | X | X | X | X | X | X | X | X | X | X | X | X |
| Water Deioniz. qs 100% | X | X | X | X | X | X | X | X | X | X | X | X |
| Sorbitan Stearate/Sucrose Cocoate 3%-7% | X | | | | | | | X | | | | X |
| Sucrose Laurate 3%-7% | | X | | | | | X | | X | | | |
| Poloxamer 407 3%-7% | | | X | | | X | | X | | | | |
| Polyoxyethylene(20)Sorbate Monoleate 3%-5% | | | | X | X | | | | | X | | |
| Primary emulsion W1/O 50% | X | X | X | X | X | X | X | X | X | X | | |
| Thickeners (water swellable polymers) 0.3%-1% | X | X | X | X | X | X | X | X | X | X | X | X |
| Water deionized Qs 100% | X | X | X | X | X | X | X | X | X | X | X | X |
| Perfume oils 0.1%-0.4% | X | X | X | X | X | X | X | X | X | X | X | X |
| UV-absorber according to the invention 0.1%-20% | X | X | X | X | X | X | X | X | X | X | X | X |
| UV-absorber as described in table 1-3 0%-30% | X | X | X | X | X | X | X | X | X | X | X | X |

O1/W/O2 emulsions

| Ingredients | 1 | 2 | 3 | 4 | 5 | 6 | 7 | 8 |
|---|---|---|---|---|---|---|---|---|
| Primary emulsion O1/W | | | | | | | | |
| PEG-60 Hydrogenated Castor Oil 25% | X | | | X | X | | | X |
| Steareth-25 25% | | | X | X | | | X | X |
| Oil phase 75% | | | | | | | | |
| Fatty acid esters | X | | X | | | | | |
| Natural and synthetic Triglycerides | | X | | X | | | | |
| Hydrocarbon oils | | | | | X | | X | |
| Silicone oils | | | | | | X | | X |
| Preservatives 0.3%-0.8% | X | X | X | X | X | X | X | X |
| Water deionized Qs 100% | X | X | X | X | X | X | X | X |
| Non ionic multifunctional W/O emulsifier 2%-5% | X | X | X | X | X | X | X | X |
| Waxes 1%-5% | X | X | X | X | X | X | X | X |
| Oil phase 20%-30% | X | X | X | X | X | X | X | X |
| Silicone oils | | | | | | | | |
| Primary emulsion O1/W 15% | X | X | X | X | X | X | X | X |
| Electrolytes (NaCl, MgSO$_4$) 0.1%-0.5% | X | X | X | X | X | X | X | X |
| Water deionized Qs 100% | X | X | X | X | X | X | X | X |
| Perfume oils 0.1%-0.4% | X | X | X | X | X | X | X | X |
| UV-absorber according to the invention 0.1%-20% | X | X | X | X | X | X | X | X |
| UV-absorber as described in table 1-3 0%-30% | X | X | X | X | X | X | X | X |

O/W Spray emulsions

| Ingredients | 1 | 2 | 3 | 4 | 5 | 6 |
|---|---|---|---|---|---|---|
| Alkyl Phosphates 0.1%-5% | X | | | X | X | |
| Glucosidic derivatives 0.1%-5% Solubilisants | | X | X | | | X |
| Ethoxylated Glyceryl ethers 0.1%-1% | X | | X | | | |
| Polysorbates 0.1%-1% | | X | | X | | |
| Ethoxylated Oleyl ethers 0.1%-1% | | | | | X | X |
| PVP/VA Coplymer 1%-10% | X | | X | | X | |
| PVM/MA Copolymer 1%-10% | | X | | X | | X |
| Oil phase 5%-20% | X | X | X | X | X | X |
| Natural oils (Meadowfoam, Jojoba, Macadamia . . .) | X | X | X | X | X | X |
| Fatty acids esters | X | X | X | X | X | X |
| Mineral oils | X | X | X | X | X | X |
| Silicone oils | X | X | X | X | X | X |
| Alcohol 0%-50% | X | X | X | X | X | X |
| Thickeners 0.1%-0.5% | X | X | X | X | X | X |
| Polyacrylates | X | X | X | X | X | X |
| Aluminium/Magnesium Silicates | X | X | X | X | X | X |
| Gums | X | X | X | X | X | X |
| Neutralizing agents 0%-1% | X | X | X | X | X | X |
| Polyalcohols/Humectants 1%-5% | X | X | X | X | X | X |
| Chelating agents (such as EDTA) 0%-0.2% | X | X | X | X | X | X |
| Antioxidants 0.05%-0.2% | X | X | X | X | X | X |
| Water Deioniz. qs 100% | X | X | X | X | X | X |
| Perfume oils 0.1%-0.5% | X | X | X | X | X | X |
| Preservatives 0.4%-1% | X | X | X | X | X | X |
| UV-absorber according to the invention 0.1%-20% | X | X | X | X | X | X |
| UV-absorber as described in table 1-3 0%-30% | X | X | X | X | X | X |

Microemulsions

| Ingredients | 1 | 2 | 3 | 4 | 5 | 6 | 7 | 8 | 9 | 10 |
|---|---|---|---|---|---|---|---|---|---|---|
| PEG-B Caprylic/Capric Glycerides 10%-25% | X | | | X | X | | | X | X | |
| PPG-5-ceteth-20 10%-25% | | X | X | | | X | X | | | X |
| Polyglyceryl-6 Isostearate 5%-15% | X | | X | | | | | | | |
| Polyglyceryl-3 Diisostearate 5%-15% | | X | | X | | | | | | |
| Polyglyceryl-6 Dioleate 5%-15% | | | | | X | | X | | | |
| PPG-10 Cetyl Ether 5%-15% | | | | | | X | | X | | |
| Ethoxydiglycol 5%-15% | | | | | | | | | X | X |
| Oil phase 10%-80% | X | X | X | X | X | X | X | X | X | X |
| Isostearyl Benzoate | X | X | X | X | X | X | X | X | X | X |
| Isostearyl Isostearate | X | X | X | X | X | X | X | X | X | X |
| PEG-7 Glyceryl Cocoate | X | X | X | X | X | X | X | X | X | X |
| Cyclomethicone | X | X | X | X | X | X | X | X | X | X |
| Polyalcohols/Humectants 1%-10% | X | X | X | X | X | X | X | X | X | X |
| Preservatives 0.3-0.8% | X | X | X | X | X | X | X | X | X | X |
| Perfume oils 0.1%-0.4% | X | X | X | X | X | X | X | X | X | X |
| Water Deioniz. qs 100% | X | X | X | X | X | X | X | X | X | X |
| UV-absorber according to the invention 0.1%-20% | X | X | X | X | X | X | X | X | X | X |
| UV-absorber as described in table 1-3 0%-30% | X | X | X | X | X | X | X | X | X | X |

| Ingredients | G - Aqueous | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Thickeners | | | | | | | | | | | | |
| Natural Thickener 1%-5% | X | | | | | X | X | | | | | X |
| Semi-synthetic Thickener 1%-5% | | X | | | X | | | X | | | X | |
| Synthetic Thickener 0.3%-1.3% | | | X | X | | | | | X | X | | |
| Neutralizing Agents 0.5%-1.5% | X | X | X | X | X | X | X | X | X | X | X | X |
| Polyols - Humectants 5%-50% | X | X | X | X | X | X | X | X | X | X | X | X |
| Polyquaternium series 1%-5% | X | X | X | | | | X | X | X | | | |
| PVM/MA Copolymer 1%-5% | | | | X | X | X | | | | X | X | X |
| Preservatives 0.5%-1% | X | X | X | X | X | X | X | X | X | X | X | X |
| Chelating Agents (as EDTA) <0.1% | X | X | X | X | X | X | X | X | X | X | X | X |
| Water Deioniz. qs 100% | X | X | X | X | X | X | X | X | X | X | X | X |
| Perfume oils 0.05%-0.4% | X | X | X | X | X | X | X | X | X | X | X | X |
| Ethoxylated Glyceryl ethers 0.1%-5% | X | X | X | | | | | | | | | |
| Polysorbates 0.1%-5% | | | | X | X | X | | | | | | |
| Ethoxylated Oleyl ethers 0.1%-5% | | | | | | | X | X | X | X | X | X |
| UV-absorber according to the invention 0.1%-20% | X | X | X | X | X | X | X | X | X | X | X | X |
| UV-absorber as described in table 1-3 0%-30% | X | X | X | X | X | X | X | X | X | X | X | X |

| Ingredients | Oleogels | | | | | | | | | |
|---|---|---|---|---|---|---|---|---|---|---|
| | 1 | 2 | 3 | 4 | 5 | 6 | 7 | 8 | 9 | 10 |
| Hydrogenated Lecithin 1%-10% | X | | | | | | | | | X |
| Silica Dimethyl Silylate 1%-10% | | X | | | | | | | X | |
| Silica 1%-5% | | | X | | | | | X | | |
| $C_{24-28}$ Alkyl Dimethicone 1%-5% | | | | X | | | X | | | |
| Aluminium or Magnesium Stearate 1%-5% | | | | | X | X | | | | |
| Polyols - Humectants 5%-70% | X | X | X | X | X | X | X | X | X | X |
| Oil phase 20%-90% | | | | | | | | | | |
| Dicaprylyl Ether | X | | | | | | X | X | | |
| Phenyl Trimethicone | | X | | | | | X | | | |
| Hydrogenated Polyisobutene | | | | X | | | | | | |
| Isopropyl Isostearate | | | | | X | | | | X | |
| Oleogel basis (Mineral oil and hydrogenated Butylene/Ethylene or Ethylene/Propylene Styrene Copolymer) | | | | | | X | | | | X |
| Silicone wax 1%-10% | X | X | X | X | X | X | X | X | X | X |
| Dimethiconol Behenate | X | X | X | X | X | X | X | X | X | X |
| Dimethiconol Stearate | X | X | X | X | X | X | X | X | X | X |
| Perfume oils 0.1%-0.5% | X | X | X | X | X | X | X | X | X | X |
| Antioxidants 0.05%-0.2% | X | X | X | X | X | X | X | X | X | X |
| UV-absorber according to the invention 0.1%-20% | X | X | X | X | X | X | X | X | X | X |
| UV-absorber as described in table 1-3 0%-30%) | X | X | X | X | X | X | X | X | X | X |

| Ingredients | Light/dry cosmetic oils | | | |
|---|---|---|---|---|
| | 1 | 2 | 3 | 4 |
| Hydrocarbon oils 30%-70% | X | | | X |
| Fatty acid esters branched or not 10%-50% | | X | X | |
| Silicones/Siloxanes 0%-10% | X | | X | |
| Perfluorinated oils and Perfluoroethers 0%-10% | | X | | X |
| Viscosifying agents 0%-10% | X | X | X | X |
| Esters of long chain acids and alcohols 0%-2% | X | X | X | X |
| Antioxidants 0.1%-1% | X | X | X | X |
| Solubilisants/dispersing agents 0%-5% | X | X | X | X |
| Perfume oils 0.1%-0.5% | X | X | X | X |
| UV-absorber according to the invention 0.1%-20%. | X | X | X | X |
| UV-absorber as described in table 1-3 0%-30% | X | X | X | X |

| Foaming/mousse products | |
|---|---|
| Ingredients | 1 |
| SD Alcohol 40 0%-8% | X |
| Propellant 8%-15% | X |
| Nonionic Emulsifier/Surfactant 0.5%-3% | X |
| Corrosion Inhibitor 0%-1% | X |
| Perfume oils 0.1%-0.5% | X |
| Preservatives 0.1%-1% | X |
| Miscellaneous 0%-1% | X |
| UV-absorber according to the invention 0.1%-20%. | X |
| UV-absorber as described in table 1-3 0%-30% | X |

| Stick products | |
|---|---|
| Ingredients | 1 |
| Waxes 15%-30% | X |
| Natural and silicone oils 20%-75% | X |
| Lanoline derivatives 5%->50% | X |
| Esters of lanolin | x |
| Acetylated lanolin | x |
| Lanolin oil | x |
| Colorants and pigments 10%-15% | X |
| Antioxidants 0.1%-0.8% | X |
| Perfume oils 0.1%-2% | X |
| Preservatives 0.1%-0.7% | X |
| UV-absorber according to the invention 0.1%-20% | X |
| UV-absorber as described in table 1-3 0%-30% | X |

| Liquid and compact | | |
|---|---|---|
| Ingredients | 1 | 2 |
| Liquid foundation | | |
| Powder phase 10%-15% | X | |
| Oil phase 30%-40%; 75% (only for anhydrous form) | X | |
| Thickener/suspending agents 1%-5% | X | |
| Film forming polymers 1%-2% | X | |
| Antioxidants 0.1%-1% | X | |
| Perfume oils 0.1%-0.5% | X | |
| Preservatives 0.1%-0.8% | X | |
| Water deionized Qs 100% | X | |
| Compact powder | | |
| Powder phase 15%-50% | | X |
| Oil phase 15%-50% | | X |
| Polyol phase 5%-15% | | X |
| Antioxidants 0.1%-1% | | X |
| Perfume oils 0.1%-0.5% | | X |
| Preservatives 0.1%-0.8% | | X |
| For the two product forms | | |
| UV-absorber according to the invention 0.1%-20% | X | X |
| UV-absorber as described in table 1-3 0%-30% | X | X |

| Conditioning Shampoos | |
|---|---|
| Ingredients | 1 |
| Primary surfactants (listed previously) 5%-10% | X |
| Secondary surfactants (listed previously) 5%-15% | X |
| Foam Stabilizers (listed previously) 0%-5% | X |
| Water deionized 40%-70% | X |

-continued

| Conditioning Shampoos | |
|---|---|
| Ingredients | 1 |
| Actives 0-10% | X |
| Conditioners | x |
| Refatting agents | x |
| Moisturizing agents | x |
| Thickeners/Rheology mofifiers 0%-3% | X |
| Humectants 0%-2% | X |
| PH adjusting agents 0%-1% | X |
| Preservatives 0.05%-1% | X |
| Perfume oils 0.1%-1% | X |
| Antioxidants 0.05%-0.20% | X |
| Chelating Agents (EDTA) 0%-0.2% | X |
| Opascifying agents 0%-2% | X |
| UV-absorber according to the invention 0.1%-20% | X |
| UV-absorber as described in table 1-3 0%-30% | X |

The cosmetic preparation according to the invention is distinguished by excellent protection of human skin against the damaging effect of sunlight.

EXAMPLES

Preparation of UV Absorbers

Example 1

Preparation of the Compound of Formula (101)

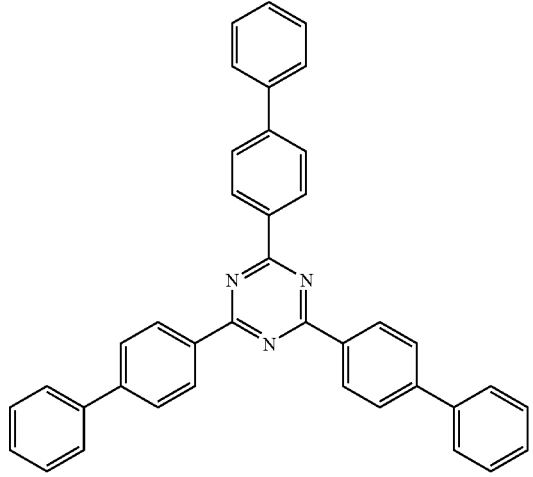

(101)

Cyanuric chloride (36.9 g, 0.20 mol) is dissolved in 1,2-dichlorobenzene (500 ml). Aluminum chloride (96.0 g, 0.72 mol) is added and the reaction mixture is heated up to 140° C. Biphenyl (111.0 9, 0.72 mol), dissolved in 200 ml 1,2-dichlorobenzene, is added slowly dropwise and the temperature is maintained at 140-145° C. for 1 to 4 hours.

The reaction mixture is cooled down to about 60° C. and added to a mixture of 150 ml conc. HCl and 350 g ice. After phase separation at about 110° C. the dichloro benzene phase is removed, stirred with Na$_2$CO$_3$ and filtered hot at 100-110° C. The desired compound restallizes from the filtrate.

For purification the compound is recrystallized from dichlorobenzene and dioxane.

$^{13}$C NMR (90 MHz, CDCl$_3$, TMS):

|  | δ (ppm) | % Int. |
|---|---|---|
| Peak |  |  |
| 1 | 171.8 | 15.6 |
| 2 | 145.6 | 21.6 |
| 3 | 140.8 | 18.3 |
| 4 | 135.6 | 26.4 |
| 5 | 129.9 | 62.2 |
| Peak Nr. |  |  |
| 6 | 129.3 | 98.6 |
| 7 | 128.4 | 32.5 |
| 8 | 127.8 | 62.9 |
| 9 | 127.7 | 100.0 |

Example 2

Biphenyl (200.0 g, 1.28 mol) is submitted and melted at 70-75° C. Cyanuric chloride (9.2 g, 0.05 mol) is added and hydrogen chloride is discharged for 10 minutes. Aluminum chloride (20.0 g, 0.1 5 mol) is added within 40 minutes in 5 equal portions, whereby hydrogen chloride is discharged again after the first two additions. After termination of the reaction 95 per cent ethanol (200 ml) is added dropwise slowly. The reaction mixture is heated up for 1 h under reflux. Finally, acetone (400 ml) is added and agitated for 1 h, cooled down to room temperature and the failed product is filterd under suction.

Yield of tris(biphenyl)-1,3,5-triazin (formula 101): approx. 65%

Example 3

Preparation of the Compound of Formula (102)

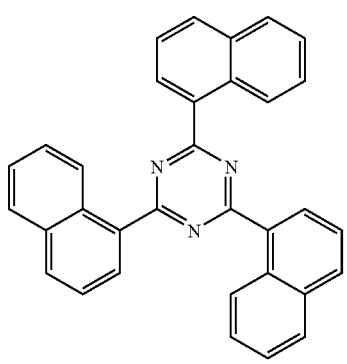

According to the procedure described in Example 1 the compound of formula (102) is obtained, if naphthalene is used instead of biphenyl.

Example 4

Preparation of the Compound of Formula (103)

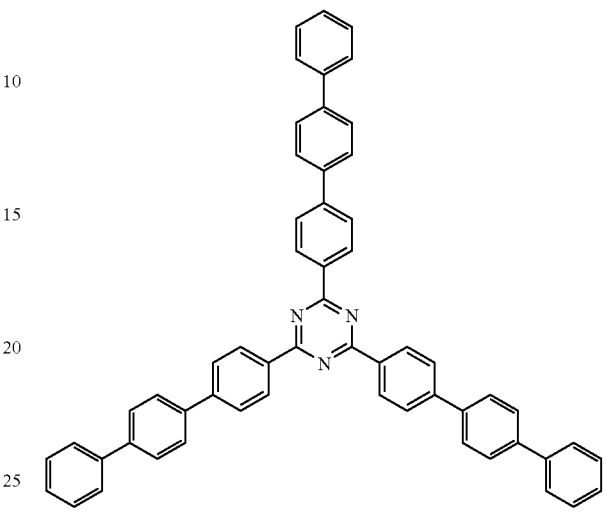

Reaction Scheme:

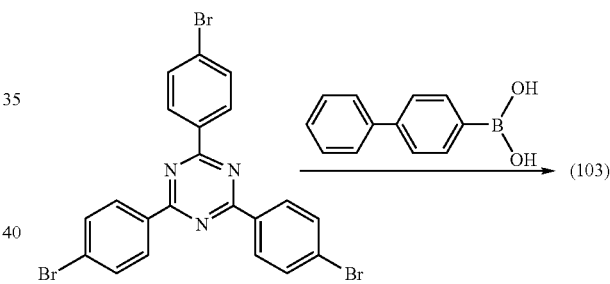

Example 4a 0.5 g 2,4,6-Tris-(4-Bromophenyl)-1,3,5-triazin (CAS Nr. 30363-03-2) and 0.816 g of 4-biphenylboronic acid are added to 10 ml of toluene under argon. 2.238 g of Cesium carbonate are dissolved in 3.5 ml water and added to the reaction mixture. After the addition of 0.03 equivalents of a palladium(I) catalyst, the reaction mixture is heated under reflux for 4 h. The reaction mixture is cooled down to room temperature and then filtered. The filter cake is dissolved in hot DMF, filtered and under cooling the desired product crystallized out. The white fine needles have a melting point of 360° C. and the $^1$H-NM confirmed the structure.

NMR-Data: 1H-NMR (340 MHz, CDCl3): δ=8.83 (d, 6H), 7.82 (d, 6H), 7.75 (d, 6H), 7.67 (d, 6H), 7.62-7.60 (m, 6H), 7.44-7.40 (m, 6H), 7.34-7.30 ppm (m, 3H).

Instead of the bromide, also the chloride, iodide or tosylate might be used as starting material. Bromide is preferred.

Example 4b

The compound of formula (103) can be synthesized alternatively via the following pathway:

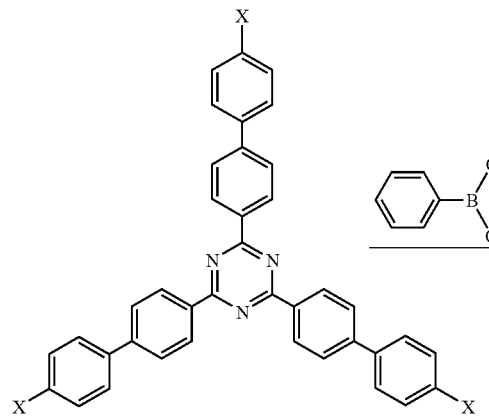

X = Cl, Br, I, O-Tosyl ( X = preferably Br)

Example 4c

Another pathway for the preparation of the compound of formula (103) is as follows:

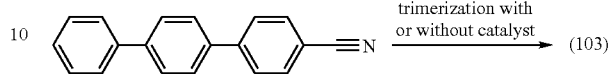

Example 4d

According to the procedure described in Example 1 the compound of formula (103) is obtained, if p-terphenyl is used instead of biphenyl.

Example 5

Preparation of the Compound of Formula (104)

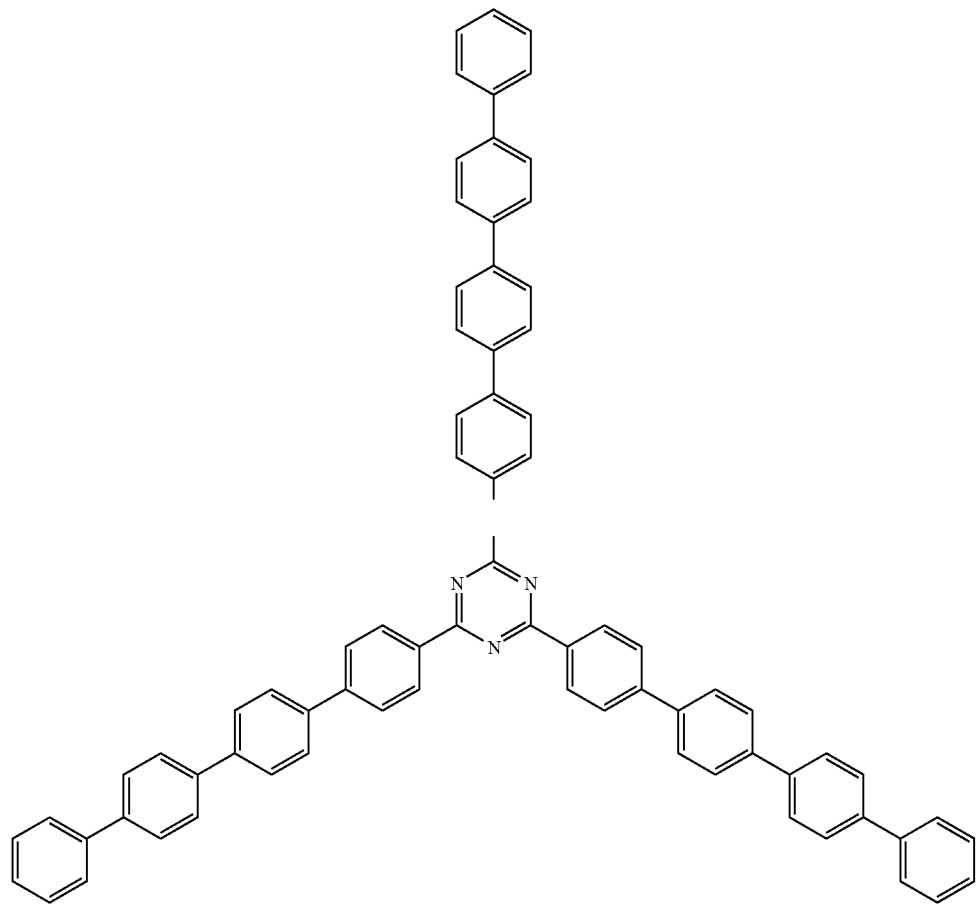

According to the procedure described in Example 1 the compound of formula (104) is obtained, if p,p-quarterphenyl is used instead of biphenyl as starting compound.

Example 6

Preparation of a Micronized UV Absorber 100 parts of the compound of formula (101), (102), (103) or (104) respectively are milled together with zirconium silicate bells (diameter: 0,1 to 4 mm) as grinding aids, a dispersing agent (15 parts of $C_8$-$C_{16}$polyglucoside) and water (85 parts) in a ball mill to a mean particle size of $d_{50}$=130 nm.

With this method a micropigment dispersion of a UV absorber is obtained.

Example 7

Preparation of a Micronized UV Absorber 100 parts of the compound of formula (101), (102), (103) or (104) respectively are milled together with zirconium silicate bells (diameter: 0.1 to 4 mm) as grinding aids, a dispersing agent (15 parts $C_{12}$gyceride-PEG10) and water (85 parts) in a ball mill to a mean particle size of $d_{50}$=130 nm.

With this method a micropigment dispersion of a UV absorber is obtained.

Application Examples

| | INCI-Name | % w/w (as supplied) | | | | | |
|---|---|---|---|---|---|---|---|
| | | 8a | 8b | 8c | 8d | 8e | 8f |
| Part A | Oleth-3 Phosphate | 0.60 | 0.60 | 0.60 | 0.60 | 0.60 | 0.60 |
| | Steareth-21 | 2.50 | 2.50 | 2.50 | 2.50 | 2.50 | 2.50 |
| | Steareth-2 | 1.00 | 1.00 | 1.00 | 1.00 | 1.00 | 1.00 |
| | Cetyl Alcohol | 0.80 | 0.80 | 0.80 | 0.80 | 0.80 | 0.80 |
| | Stearyl Alcohol | 1.50 | 1.50 | 1.50 | 1.50 | 1.50 | 1.50 |
| | Tribehenin | 0.80 | 0.80 | 0.80 | 0.80 | 0.80 | 0.80 |
| | Isohexadecane | 8.00 | 8.00 | 8.00 | 8.00 | 8.00 | 8.00 |
| | Ethylhexyl Methoxycinnamate | 3.00 | 3.00 | 3.00 | 3.00 | 3.00 | 3.00 |
| | Compound of the formula ($a_4$) | 2.00 | | | | | |
| | Compound of the formula ($d_4$) as described in claim 18 | | 1.30 | | | | |
| | Compound of the formula ($h_2$, 1) as described in claim 21 | | | 1.50 | | | |
| | Compound of the formula ($i_2$) (Mexoryl DTS) | | | | 2.00 | | |
| | Compound of the formula (l2) as described in claim 26 | | | | | 1.50 | |
| | Compound of the formula ($b_4$) | | | | | | 2.00 |
| Part B | Water | qs to 100 | qs to 100 | qs to 100 | qs to 100 | qs to 100 | qs to 100 |
| | Glycerin | 2.00 | 2.00 | 2.00 | 2.00 | 2.00 | 2.00 |
| | UV-absorber dispersion as described in example 6; compound of formula (101) | 3.00 | 3.00 | 3.00 | 3.00 | 3.00 | 3.00 |
| | Phenylbenzimidazolsulfonic acid (Eusolex 232) | | | | 2.00 | | |
| | Disodium EDTA | 0.10 | 0.10 | 0.10 | 0.10 | 0.10 | 0.10 |
| Part C | Water | 20.00 | 20.00 | 20.00 | 20.00 | 20.00 | 20.00 |
| | Diazolidinyl Urea (and) Iodopropynyl Butylcarbamate | 0.15 | 0.15 | 0.15 | 0.15 | 0.15 | 0.15 |
| | Propylene Glycol | 4.00 | 4.00 | 4.00 | 4.00 | 4.00 | 4.00 |
| Part D | Sodium Acrylates Copolymer (and) Paraffinium Liquidum (and) PPG-1 Trideceth-6 | 1.50 | 1.50 | 1.50 | 1.50 | 1.50 | 1.50 |
| | Cyclopentasiloxane | 4.00 | 4.00 | 4.00 | 4.00 | 4.00 | 4.00 |
| | PEG-12 Dimethicone | 2.00 | 2.00 | 2.00 | 2.00 | 2.00 | 2.00 |
| | Tocopheryl Acetate | 0.45 | 0.45 | 0.45 | 0.45 | 0.45 | 0.45 |
| | Water (and) Citric Acid | Qs | Qs | Qs | Qs | Qs | Qs |
| Part E | Fragrance | Qs | Qs | Qs | Qs | Qs | Qs |

| | INCI-Name | % w/w (as supplied) | | | | | |
|---|---|---|---|---|---|---|---|
| | | 8a | 8b | 8c | 8d | 8e | 8f |
| Part A | Oleth-3 Phosphate | 0.60 | 0.60 | 0.60 | 0.60 | 0.60 | 0.60 |
| | Steareth-21 | 2.50 | 2.50 | 2.50 | 2.50 | 2.50 | 2.50 |
| | Steareth-2 | 1.00 | 1.00 | 1.00 | 1.00 | 1.00 | 1.00 |

-continued

|  | INCI-Name | 8a | 8b | 8c | 8d | 8e | 8f |
|---|---|---|---|---|---|---|---|
|  | Cetyl Alcohol | 0.80 | 0.80 | 0.80 | 0.80 | 0.80 | 0.80 |
|  | Stearyl Alcohol | 1.50 | 1.50 | 1.50 | 1.50 | 1.50 | 1.50 |
|  | Tribehenin | 0.80 | 0.80 | 0.80 | 0.80 | 0.80 | 0.80 |
|  | Isohexadecane | 8.00 | 8.00 | 8.00 | 8.00 | 8.00 | 8.00 |
|  | Ethylhexyl Methoxycinnamate | 3.00 | 3.00 | 3.00 | 3.00 | 3.00 | 3.00 |
|  | Compound of the formula ($a_4$) | 2.00 |  |  |  |  |  |
|  | Compound of the formula ($d_4$) as described in claim 18 |  | 1.30 |  |  |  |  |
|  | Compound of the formula ($h_2$, 1) as described in claim 21 |  |  | 1.50 |  |  |  |
|  | Compound of the formula ($i_2$) (Mexoryl DTS) |  |  |  | 2.00 |  |  |
|  | Compound of the formula (l2) as described in claim 26 |  |  |  |  | 1.50 |  |
|  | Compound of the formula ($b_4$) |  |  |  |  |  | 2.00 |
| Part B | Water | qs to 100 | qs to 100 | qs to 100 | qs to 100 | qs to 100 | qs to 100 |
|  | Glycerin | 2.00 | 2.00 | 2.00 | 2.00 | 2.00 | 2.00 |
|  | UV-absorber dispersion as described in example 6; compound of formula (103) | 3.00 | 3.00 | 3.00 | 3.00 | 3.00 | 3.00 |
|  | Phenylbenzimidazolsulfonic acid (Eusolex 232) | 2.00 |  |  |  |  |  |
|  | Disodium EDTA | 0.10 | 0.10 | 0.10 | 0.10 | 0.10 | 0.10 |
| Part C | Water | 20.00 | 20.00 | 20.00 | 20.00 | 20.00 | 20.00 |
|  | Diazolidinyl Urea (and) Iodopropynyl Butylcarbamate | 0.15 | 0.15 | 0.15 | 0.15 | 0.15 | 0.15 |
|  | Propylene Glycol | 4.00 | 4.00 | 4.00 | 4.00 | 4.00 | 4.00 |
| Part D | Sodium Acrylates Copolymer (and) Paraffinium Liquidum (and) PPG-1 Trideceth-6 | 1.50 | 1.50 | 1.50 | 1.50 | 1.50 | 1.50 |
|  | Cyclopentasiloxane | 4.00 | 4.00 | 4.00 | 4.00 | 4.00 | 4.00 |
|  | PEG-12 Dimethicone | 2.00 | 2.00 | 2.00 | 2.00 | 2.00 | 2.00 |
|  | Tocopheryl Acetate | 0.45 | 0.45 | 0.45 | 0.45 | 0.45 | 0.45 |
|  | Water (and) Citric Acid | Qs | Qs | Qs | Qs | Qs | Qs |
| Part E | Fragrance | Qs | Qs | Qs | Qs | Qs | Qs |

|  | INCI-Name | 8a | 8b | 8c | 8d | 8e | 8f |
|---|---|---|---|---|---|---|---|
| Part A | Oleth-3 Phosphate | 0.60 | 0.60 | 0.60 | 0.60 | 0.60 | 0.60 |
|  | Steareth-21 | 2.50 | 2.50 | 2.50 | 2.50 | 2.50 | 2.50 |
|  | Steareth-2 | 1.00 | 1.00 | 1.00 | 1.00 | 1.00 | 1.00 |
|  | Cetyl Alcohol | 0.80 | 0.80 | 0.80 | 0.80 | 0.80 | 0.80 |
|  | Stearyl Alcohol | 1.50 | 1.50 | 1.50 | 1.50 | 1.50 | 1.50 |
|  | Tribehenin | 0.80 | 0.80 | 0.80 | 0.80 | 0.80 | 0.80 |
|  | Isohexadecane | 8.00 | 8.00 | 8.00 | 8.00 | 8.00 | 8.00 |
|  | Ethylhexyl Methoxycinnamate | 3.00 | 3.00 | 3.00 | 3.00 | 3.00 | 3.00 |
| Part B | Water | qs to 100 | qs to 100 | qs to 100 | qs to 100 | qs to 100 | qs to 100 |
|  | Glycerin | 2.00 | 2.00 | 2.00 | 2.00 | 2.00 | 2.00 |
|  | UV-absorber dispersion as described in example 6; compound of formula (101) | 3.00 | 3.00 | 3.00 | 3.00 | 3.00 | 3.00 |
|  | Compound of the formula ($m_2$) (Mexoryl SL) | 2.00 |  |  |  |  |  |
|  | Compound of the formula (n2) (Mexoryl SO) |  | 1.50 |  |  |  |  |
|  | Ubiquinone |  |  | 0.01 |  |  |  |
|  | Micronized compound of the formula ($c_4$) |  |  |  | 2.00 |  |  |
|  | Phenylbenzimidazolsulfonic acid (Eusolex 232) |  |  |  |  |  | 2.00 |
|  | Disodium EDTA | 0.10 | 0.10 | 0.10 | 0.10 | 0.10 | 0.10 |

-continued

|  | INCI-Name | % w/w (as supplied) | | | | | |
|---|---|---|---|---|---|---|---|
|  |  | 8a | 8b | 8c | 8d | 8e | 8f |
| Part C | Water | 20.00 | 20.00 | 20.00 | 20.00 | 20.00 | 20.00 |
|  | Diazolidinyl Urea (and) Iodopropynyl Butylcarbamate | 0.15 | 0.15 | 0.15 | 0.15 | 0.15 | 0.15 |
|  | Propylene Glycol | 4.00 | 4.00 | 4.00 | 4.00 | 4.00 | 4.00 |
| Part D | Sodium Acrylates Copolymer (and) Paraffinium Liquidum (and) PPG-1 Trideceth-6 | 1.50 | 1.50 | 1.50 | 1.50 | 1.50 | 1.50 |
|  | Cyclopentasiloxane | 4.00 | 4.00 | 4.00 | 4.00 | 4.00 | 4.00 |
|  | PEG-12 Dimethicone | 2.00 | 2.00 | 2.00 | 2.00 | 2.00 | 2.00 |
|  | Tocopheryl Acetate | 0.45 | 0.45 | 0.45 | 0.45 | 0.45 | 0.45 |
|  | Water (and) Citric Acid | Qs | Qs | Qs | Qs | Qs | Qs |
| Part E | Fragrance | Qs | Qs | Qs | Qs | Qs | Qs |

|  | INCI-Name | % w/w (as supplied) | | | | | |
|---|---|---|---|---|---|---|---|
|  |  | 8a | 8b | 8c | 8d | 8e | 8f |
| Part A | Oleth-3 Phosphate | 0.60 | 0.60 | 0.60 | 0.60 | 0.60 | 0.60 |
|  | Steareth-21 | 2.50 | 2.50 | 2.50 | 2.50 | 2.50 | 2.50 |
|  | Steareth-2 | 1.00 | 1.00 | 1.00 | 1.00 | 1.00 | 1.00 |
|  | Cetyl Alcohol | 0.80 | 0.80 | 0.80 | 0.80 | 0.80 | 0.80 |
|  | Stearyl Alcohol | 1.50 | 1.50 | 1.50 | 1.50 | 1.50 | 1.50 |
|  | Tribehenin | 0.80 | 0.80 | 0.80 | 0.80 | 0.80 | 0.80 |
|  | Isohexadecane | 8.00 | 8.00 | 8.00 | 8.00 | 8.00 | 8.00 |
|  | Ethylhexyl Methoxycinnamate | 3.00 | 3.00 | 3.00 | 3.00 | 3.00 | 3.00 |
| Part B | Water | qs to 100 | qs to 100 | qs to 100 | qs to 100 | qs to 100 | qs to 100 |
|  | Glycerin | 2.00 | 2.00 | 2.00 | 2.00 | 2.00 | 2.00 |
|  | UV-absorber dispersion as described in example 6; compound of formula (103) | 3.00 | 3.00 | 3.00 | 3.00 | 3.00 | 3.00 |
|  | Compound of the formula ($m_2$) (Mexoryl SL) | 2.00 |  |  |  |  |  |
|  | Compound of the formula ($n2$) (Mexoryl SO) |  | 1.50 |  |  |  |  |
|  | Ubiquinone |  |  | 0.01 |  |  |  |
|  | Micronized compound of the formula ($c_4$) |  |  |  | 2.00 |  |  |
|  | Phenylbenzimidazolsulfonic acid (Eusolex 232) |  |  |  |  |  | 2.00 |
|  | Disodium EDTA | 0.10 | 0.10 | 0.10 | 0.10 | 0.10 | 0.10 |
| Part C | Water | 20.00 | 20.00 | 20.00 | 20.00 | 20.00 | 20.00 |
|  | Diazolidinyl Urea (and) Iodopropynyl Butylcarbamate | 0.15 | 0.15 | 0.15 | 0.15 | 0.15 | 0.15 |
|  | Propylene Glycol | 4.00 | 4.00 | 4.00 | 4.00 | 4.00 | 4.00 |
| Part D | Sodium Acrylates Copolymer (and) Paraffinium Liquidum (and) PPG-1 Trideceth-6 | 1.50 | 1.50 | 1.50 | 1.50 | 1.50 | 1.50 |
|  | Cyclopentasiloxane | 4.00 | 4.00 | 4.00 | 4.00 | 4.00 | 4.00 |
|  | PEG-12 Dimethicone | 2.00 | 2.00 | 2.00 | 2.00 | 2.00 | 2.00 |
|  | Tocopheryl Acetate | 0.45 | 0.45 | 0.45 | 0.45 | 0.45 | 0.45 |
|  | Water (and) Citric Acid | Qs | Qs | Qs | Qs | Qs | Qs |
| Part E | Fragrance | Qs | Qs | Qs | Qs | Qs | Qs |

Manufacturing Instruction for Examples 8a-8d

Part A and part B are heated separately to 75° C. Part A is poured into part B under continuous stirring. Immediately after the emulsification, cyclopentasiloxane and PEG-12 Dimethicone from part D are incorporated into the mixture. Afterwards the mixture is homogenized with an Ultra Turrax at 11 000 rpm for 30 sec. After cooling down to 65° C. Sodium Acrylates Copolymer (and) Paraffinium Liquidum (and) PPG-1 Trideceth-6 are incorporated. Part C is added at a temperature <50° C. At a temperature ≦35° C. Tocopheryl Acetate is incorporated and subsequently the pH is adjusted with Water (and) Citric Acid. At room temperature part E is added.

Example 9

UV Day Lotion

| | INCI-Name | % w/w (as supplied) |
|---|---|---|
| Part A | Cetyl Phosphate | 1.75 |
| | C12-C15 Alkyl Benzoate | 4.00 |
| | Cetearyl Alcohol/PEG-20 Stearate | 2.00 |
| | Ethoxydiglycol Oleate | 2.00 |
| | Stearic Acid | 1.50 |
| | Ethylhexyl Methoxycinnamate | 3.00 |
| | Isononyl Isononanoate | 2.00 |
| | Bis-ethylhexyloxyphenol methoxyphenyl triazine (Tinosorb S) | 1.00 |
| Part B | Aqua | qs to 100 |
| | Xanthan Gum | 0.35 |
| | UV-absorber dispersion as described in example 6 | 5.00 |
| | Disodium EDTA | 0.20 |
| | Propylene Glycol | 2.00 |
| | Diazolidinyl Urea (and) Methylparaben (and) Propylparaben (and) Propylene Glycol | 0.70 |
| | Glycerin | 1.50 |
| Part C | Cyclopentasiloxane (and) Dimethiconol | 1.00 |
| | Ethoxydiglycol | 3.00 |
| | Dimethicone | 2.00 |
| Part D | Triethanolamine | qs |

Manufacturing Instruction:

Part A by is prepared by incorporating all ingredients, then stirred under moderate speed and heated to 75° C. Part B s prepared and heated to 75° C. At this temperature part B is poured into part A under progressive stirring speed. Then the mixture is homogenized (30 sec., 15000 rpm ). At a temperature <55° C. the ingredients of part C are incorporated. The mixture is cooled down under moderate stirring, then the pH is checked and adjusted with triethanolamine.

Example 10

Sun Protection Emulsion

| | INCI-Name | % w/w (as supplied) |
|---|---|---|
| Part A | Cetearyl Alcohol (and) Dicetyl Phosphate (and) Ceteth-10 Phosphate | 4.00 |
| | C12-15 Alkyl Benzoate | 2.00 |
| | Dicaprylyl Ether | 3.00 |
| | Ethoxydiglycol Oleate | 2.00 |
| | Stearic Acid | 1.00 |
| | Ethylhexyl Methoxycinnamate | 3.00 |
| | Sodium Acrylates Copolymer (and) Glycine Soja (and) PPG-1 Trideceth-6 | 0.30 |
| | Squalane | 3.50 |
| Part B | Aqua | qs to 100 |
| | UV-absorber dispersion as described in example 6 | 5.00 |
| Part C | Diazolidinyl Urea (and) Iodopropynyl Butylcarbamate | 0.15 |
| | Propylene Glycol | 2.50 |
| | Aqua | 10.00 |
| Part D | Cyclopentasiloxane, Dimethiconol | 2.00 |
| | Ethoxydiglycol | 5.00 |
| | Cyclopentasiloxane (and) Dimethicone/Vinyl-dimethicone Crosspolymer | 2.00 |
| Part E | Sodium Hydroxide | 0.10 |

Manufacturing Instruction:

Part A is prepared by incorporating all ingredients, then stirred under moderate speed and heated to 75° C. Part B is prepared and heated to 75° C. At this temperature, part B is poured into part A under progressive stirring speed. Below 65° C. the ingredients of part D are added separately. After cooling down under moderate stirring to 55° C. part C is added. The pH is then checked and adjusted with sodium hydroxide. The mixture is homogenized for 30 sec at 16000 rpm.

Example 11

Every Day Lotion

| | INCI-Name | % w/w (as supplied) |
|---|---|---|
| Part A | Stearyl Phosphate | 5.00 |
| | Tricontanyl PVP | 1.00 |
| | Ethoxydiglycol Oleate | 3.00 |
| | Squalane | 5.00 |
| | C12-15 Alkyl Benzoate | 5.00 |
| | Ethylhexyl Methoxycinnamate | 3.00 |
| | Glyceryl Stearate | 2.00 |
| | Cetyl Alcohol | 2.00 |
| | Butyl methoxydibenzoylmethane (Parsol 1789) | 1.50 |
| Part B | Aqua | 20.00 |
| | UV-absorber dispersion as described in example 5 | 3.00 |
| | Methylene bis-benzotriazolyl tetramethylbutylphenol (TinosorbM) | 2.00 |
| Part C | Aqua | qs to 100 |
| | Steareth-10 Allyl Ether/Acrylates Copolymer | 0.50 |
| | Glycerin | 2.50 |
| | Diazolidinyl Urea (and) Iodopropynyl Butylcarbamate | 0.15 |
| | Sodium Lauroyl Glutamate | 0.70 |
| Part D | Cyclopentasiloxane (and) Dimethiconol | 1.50 |
| | Triethanolamine | 1.85 |

Manufacturing Instruction:

Part A is prepared by incorporating all ingredients, then stirred under moderate speed and heated to 75° C. Part C is prepared and heated to 75° C. Part C is poured into the part A under moderate stirring. Immediately after the emulsification part B is added, then neutralized with a part of the triethanolamine. The mixture is homogenized for 30 sec. After cooling down under moderate stirring Cyclopentasiloxane (and) Dimethiconol are added. Below 35° C. the pH is checked and adjusted with triethanolamine.

Example 12

Sprayable Sunscreen Emulsion

| | INCI-Name | % w/w (as supplied) |
|---|---|---|
| Part A | Ceteareth-15 (and) Glyceryl Stearate | 3.00 |
| | Stearyl Alcohol | 1.00 |
| | Cetyl Ricinoleate | 0.80 |
| | Dicaprylyl Ether | 3.00 |
| | C12-15 Alkyl Benzoate | 3.00 |
| | Isohexadecane | 2.50 |
| | Stearyl Dimethicone | 1.00 |
| | Ethylhexyl Methoxycinnamate | 4.00 |
| | Cetyl Alcohol | 0.80 |
| | Di-C12-13 Alkyl Tartrate | 3.00 |

-continued

| | INCI-Name | % w/w (as supplied) |
|---|---|---|
| Part B | Aqua | qs to 100 |
| | Steareth-10 Allyl Ether/Acrylates Copolymer | 0.45 |
| | PEG-7 Glyceryl Cocoate | 2.50 |
| | Glycerin | 2.00 |
| | Propylene Glycol | 3.00 |
| Part C | Diazolidinyl Urea (and) Iodopropynyl Butylcarbamate | 0.15 |
| | Aqua | 20.00 |
| | UV-absorber dispersion as described in example 6 | 12.00 |
| | Titanium Dioxide (and) Silica (and) Sodium Polyacrylate | 8.00 |
| Part D | Cyclopentasiloxane (and) Dimethiconol | 0.85 |
| Part E | Sodium Hydroxide (and) Water | qs to pH 6.50-7.00 |
| Part F | Fragrance | qs |

Manufacturing Instruction

Part A and part B are heated up to 80° C. Part A is blended into part B under stirring and homogenized with an UltraTurrax at 11 000 rpm for 30 sec. Part C is heated to 60° C. and added slowly to the emulsion. After cooling down to 40° C. part D is incorporated at room temperature and part E is added.

Example 13

Daily Care Lotion

| | INCI-Name | % w/w (as supplied) |
|---|---|---|
| Part A | Polyglyceryl Methyl Glucose Distearate | 2.50 |
| | Cetearyl Alcohol | 2.00 |
| | Octyl Stearate | 3.00 |
| | Caprylic/Capric Triglyceride | 4.00 |
| | Isohexadecane | 4.00 |
| | Ethylhexyl Methoxycinnamate | 2.70 |
| Part B | Aqua | 64.80 |
| | Glycerin | 5.00 |
| | Phenoxyethanol (and) Methylparaben (and) Butylparaben (and) Ethylparaben (and) Propylparaben | 0.50 |
| | UV-absorber dispersion as described in example 6 | 8.00 |
| Part C | Cyclomethicone (and) Dimethicone | 3.00 |
| Part D | Steareth-10 Allyl Ether/Acrylates Copolymer | 0.50 |

Manufacturing Instruction

Part A and B are heated to 75° C. Part A is added into part B under continuous stirring and homogenized with 11000 rpm for 1 minute. After cooling down to 50° C. part C is added under continuous stirring. After cooling further down to 30° C. part D is added. Afterwards the pH is adjusted between 6.00-6.50.

Example 14

Daily Care with UV Protection

| | INCI-Name | % w/w (as supplied) |
|---|---|---|
| Part A | Glyceryl Stearate SE | 3.00 |
| | Glyceryl Stearate and PEG-100 Stearate | 3.50 |
| | Cetyl Alcohol | 1.50 |
| | Myristyl Myristate | 2.00 |
| | Isopropyl Palmitate | 2.50 |
| | Paraffinum Perliquidum | 5.00 |
| | Octyl Dimethyl PABA | 3.00 |
| Part B | Aqua | qs to 100 |
| | Propylene Glycol | 7.50 |
| | Phenoxyethanol (and) Methylparaben (and) Butylparaben (and) Ethylparaben (and) Propylparaben | 1.00 |
| Part C | Aqua | 30.00 |
| | UV-absorber dispersion as described in example 6 | 10.00 |
| Part D | Sodium Acrylates Copolymer (and) Paraffinium Liquidum (and) PPG-1 Trideceth-6 | 2.00 |
| Part E | Citric Acid | 0.30 |

Manufacturing Instruction:

Part A and B are heated separately to 75° C. After adding part B into part A the mixture is homogenized with Ultra Turrax for one minute at 11000 rpm. After cooling down to 50° C. part C is added. Afterwards the mixture is homogenized for one minute at 16000 rpm. At a temperature <40° C. part D is added. At room temperature the pH-value is adjusted with part E between 6.00 and 6.50.

Example 15

O/W Every Day UV Protection Lotion

| | INCI-Name | % w/w (as supplied) |
|---|---|---|
| Part A | Glyceryl Stearate (and) PEG-100 Stearate | 5.00 |
| | Stearyl Alcohol | 1.00 |
| | Tripalmitin | 0.70 |
| | Dimethicone | 2.00 |
| | C12-15 Alkyl Benzoate | 5.00 |
| | Isopropyl Palmitate | 5.00 |
| | Ethylhexyl Methoxycinnamate | 3.00 |
| Part B | Water | qs to 100 |
| | Polysorbate 60 | 0.50 |
| | Glycerin | 3.00 |
| Part C | Water | 10.00 |
| | UV-absorber dispersion as described in example 6 | 8.00 |
| Part D | Phenoxyethanol (and) Methylparaben (and) Ethylparaben (and) Butylparaben (and) Propylparaben (and) Isobutylparaben | 0.70 |
| | Steareth-10 Allyl Ether/Acrylates Copolymer | 1.50 |
| Part E | Water (and) Sodium Hydroxide | qs |
| Part F | Fragrance | qs |

Manufacturing Instruction:

Part A and B are heated separately up to 75° C., part C is heated to 60° C. Afterwards part B is poured into part A under stirring. The mixture is homogenized with an Ultra Turrax for 30 sec. at 11 000 rpm and part C is incorporated. After cooling down to 40° C. part D is added. At room temperature the pH-value is adjusted with Sodium Hydroxide between 6.30 and 6.70 and part F is added.

Example 16

O/W Every Day UV Protection

| | INCI-Name | % w/w (as supplied) |
|---|---|---|
| Part A | Glyceryl Stearate (and) PEG-100 Stearate | 5.00 |
| | Stearyl Alcohol | 1.00 |
| | Tripalmitin | 0.70 |
| | Dimethicone | 2.00 |
| | C12-15 Alkyl Benzoate | 4.00 |
| | Isopropyl Palmitate | 4.00 |
| | Ethylhexyl Methoxycinnamate | 3.00 |
| | Benzophenone-3 | 1.00 |
| | Benzophenone-4 | 1.00 |
| Part B | Water | qs to 100 |
| | Polysorbate 60 | 0.50 |
| | Glycerin | 3.00 |
| Part C | Water | 10.00 |
| | UV-absorber dispersion as described in example 6 | 8.00 |
| Part D | Phenoxyethanol (and) Methylparaben (and) Ethylparaben (and) Butylparaben (and) Propylparaben (and) Isobutylparaben | 0.70 |
| | Steareth-10 Allyl Ether/Acrylates Copolymer | 1.50 |
| Part E | Water (and) Sodium Hydroxide | qs |
| Part F | Fragrance | qs |

Manufacturing Instruction:

Part A and B are heated separately up to 75° C., part C is heated to 60° C. Afterwards part B is poured into part A under stirring. The mixture is homogenized with an Ultra Turrax for 30 sec. at 11 000 rpm and part C is incorporated. After cooling down to 40° C. part D is added. At room temperature the pH-value is adjusted with Sodium Hydroxide between 6.30 and 6.70 and part F is added.

Example 17

Sunscreen Cream

| | INCI-Name | % w/w (as supplied) |
|---|---|---|
| Part A | Cetearyl Alcohol (and) Dicetyl Phosphate (and) Ceteth-10 Phosphate | 4.50 |
| | C12-15 Alkyl Benzoate | 6.00 |
| | Caprylic/Capric Triglyceride | 7.00 |
| | Pentaerythritol Tetraisostearate | 2.00 |
| | Ethylhexyl Methoxycinnamate | 3.00 |
| | Isoamyl p-Methoxycinnamate | 2.00 |
| Part B | Aqua | qs to 100 |
| | Glycerin | 2.00 |
| | Propylene Glycol | 1.50 |
| | Magnesium Aluminium Silicate | 1.20 |
| Part C | Steareth-10 Allyl Ether/Acrylates Copolymer | 0.50 |
| | UV-absorber dispersion as described in example 5 | 12.00 |
| Part D | Phenyl Trimethicone | 1.50 |
| | Phenoxyethanol (and) Methylparaben (and) Butylparaben (and) Ethylparaben (and) Propylparaben | 0.70 |
| Part E | Sodium Hydroxide | 0.90 |

Manufacturing Instructions:

Part A and part B are heated separately to 75° C. Part B is added into part A under continuous stirring and afterwards homogenized with Ultra Turrax for 30 sec at 11000 rpm. After cooling down to 60° C. part C is added. At 40° C. part C is added and homogenized for 15 sec at 11000 rpm. At room temperature the pH-value is adjusted with part E.

Example 18

UVA/UVB Daily Care Lotion, Type O/W

| | INCI-Name | % w/w (as supplied) |
|---|---|---|
| Part A | Glyceryl Stearate (and) PEG-100 Stearate | 5.00 |
| | Stearyl Alcohol | 1.00 |
| | Tripalmitin | 0.70 |
| | Mineral Oil | 15.00 |
| Part B | Water | qs to 100 |
| | Polysorbate 60 | 0.50 |
| | Glycerin | 3.00 |
| Part C | Water | 10.00 |
| | UV-absorber dispersion as described in example 6 | 8.00 |
| Part D | Steareth-10 Allyl Ether/Acrylates Copolymer | 1.50 |
| | Phenoxyethanol (and) Methylparaben (and) Ethylparaben (and) Butylparaben (and) Propylparaben (and) Isobutylparaben | 0.70 |
| Part E | Water (and) Sodium Hydroxide | qs |
| Part F | Fragrance | qs |

Manufacturing Instructions:

Part A and B are heated separately to 75° C.; part C to 60° C. Part B is poured into part A under stirring. After one-minute of homogenization at 11000 rpm part C is added to the mixture of A/B. After cooling down to 40° C. part D is incorporated. At room temperature the pH value is adjusted with part E between 6.3 and 7.0. Finally part F is added.

Example 19

UVA/UVB Daily Care Lotion, Type O/W

| | INCI-Name | % w/w (as supplied) |
|---|---|---|
| Part A | Oleth-3 Phosphate | 0.60 |
| | Steareth-21 | 2.50 |
| | Steareth-2 | 1.00 |
| | Cetyl Alcohol | 0.80 |
| | Stearyl Alcohol | 1.50 |
| | Tribehenin | 0.80 |
| | Isohexadecane | 8.00 |
| Part B | Water | qs to 100 |
| | Glycerin | 2.00 |
| | Disodium EDTA | 0.10 |
| Part C | Cyclopentasiloxane | 4.50 |
| | PEG-12 Dimethicone | 2.00 |
| Part D | Sodium Acrylates Copolymer (and) Mineral Oil (and) PPG-1 Trideceth-6 | 1.50 |
| Part E | UV-absorber dispersion as described in example 6 | 10.00 |
| Part F | Tocopheryl Acetate | 0.45 |
| | DMDM Hydantoin (and) Iodopropynyl Butylcarbamate (and) Aqua (and) Butylene Glycol | 0.85 |
| Part G | Water (and) Citric Acid | qs |
| | Fragrance | qs |

Manufacturing Instructions:

Part A and part B are heated separately to 75° C. Part A is poured into part B under stirring. Immediately after the emulsification, part C is added to the mixture and homogenized with an Ultra Turrax at 11000 rpm for 30 sec. After cooling down to 65° C. Sodium Acrylates Copolymer (and) Mineral Oil (and) PPG-1 Trideceth-6 At 50° C. is added slowly to the UV absorber dispersion. At about 35-30° C. part F is incorporated. The pH is adjusted with part G between 5.5 and 6.5.

Example 20

UV-A/UV-B Every Day Protection Lotion O/W

| | INCI-Name | % w/w (as supplied) |
|---|---|---|
| Part A | Glyceryl Dilaurate | 2.00 |
| | Ethylhexyl Palmitate | 6.00 |
| | Cetyl Alcohol | 1.00 |
| | Glyceryl Stearate | 2.00 |
| | Laureth-23 | 1.00 |
| | Isopropyl Palmitate | 2.00 |
| | Tribehenin | 0.80 |
| | Beeswax | 1.50 |
| | Lanolin Oil | 1.00 |
| Part B | Water | qs to 100 |
| | Propylene Glycol | 4.00 |
| | Water (and) Titanium Dioxide (and) Alumina (and) Sodium Meta-phosphate (and) Phenoxyethanol (and) Sodium Methylparaben | 4.00 |
| Part C | Steareth-10 Allyl Ether/Acrylates Copolymer | 1.00 |
| Part D | Phenoxyethanol (and) Methylparaben (and) Ethylparaben (and) Butylparaben (and) Propylparaben (and) Isobutylparaben | 1.00 |
| | UV-absorber dispersion as described in example 6 | 8.00 |
| Part E | Water (and) Sodium Hydroxide | qs |

Manufacturing Instructions:

Part A and part B are heated separately up to 80° C. Part A is poured into part B while stirring and homogenized with an Ultra Turrax by 11000 rpm for 30 sec. After cooling down to 60° C. part C is incorporated. At 40° C. part D is added slowly under continuous stirring. The pH is adjusted with part E between 6.50-7.00.

Example 21

Sprayable Sunscreen Lotion

| | INCI-Name | % w/w (as supplied) |
|---|---|---|
| Part A | Potassium Cetyl Phosphate | 0.20 |
| | Isohexadecane | 7.00 |
| | VP/Eicosene Copolymer | 1.50 |
| | Di-C12-13 Alkyl Tartrate | 6.00 |
| | Ethylhexyl Triazone | 2.50 |
| | C12-15 Alkyl Benzoate | 4.50 |
| Part B | Water | qs to 100 |
| | Sorbeth-30 | 2.00 |
| | Sorbitan Stearate (and) Sucrose Cocoate | 4.00 |
| | Titanium Dioxide (and) Alumina (and) Silica (and) Sodium Polyacrylate | 2.50 |
| Part C | Water | 30.00 |
| | UV-absorber dispersion as described in example 6 | 12.00 |
| Part D | Phenoxyethanol (and) Methylparaben (and) Ethylparaben (and) Butylparaben (and) Propylparaben (and) Isobutylparaben | 0.70 |
| Part E | Water (and) Citric Acid | qs |

Manufacturing Instructions:

Part A and part B are heated separately up to 80° C., part C is heated to 50° C. Part B is poured into part A and homogenized with an Ultra Turrax for 1 minute at 11000 rpm. After cooling down to 50° C. part C is added under continuous stirring. At 40° C. part D is incorporated and homogenized again for 10 sec. at 11000 rpm. The pH is adjusted with part E.

Example 22

O/W Every Day UV Protection Lotion

| | INCI-Name | % w/w (as supplied) |
|---|---|---|
| Part A | Glyceryl Stearate (and) PEG-100 Stearate | 5.00 |
| | Stearyl Alcohol | 1.00 |
| | Tripalmitin | 0.70 |
| | Dimethicone | 2.00 |
| | Caprylic/Capric Triglyceride | 5.00 |
| | Isopropyl Palmitate | 5.00 |
| | Ethylhexyl Methoxycinnamate | 3.00 |
| Part B | Water | qs to 100 |
| | Polysorbate 60 | 0.50 |
| | Glycerin | 3.00 |
| Part C | Water | 10.00 |
| | UV-absorber dispersion as described in example 6 | 8.00 |
| | ZnO (Nanox Zinc Oxide) | 3.00 |
| Part D | Phenoxyethanol (and) Methylparaben (and) Ethylparaben (and) Butylparaben (and) Propylparaben (and) Isobutylparaben | 0.70 |
| | Steareth-10 Allyl Ether/Acrylates Copolymer | 1.50 |
| Part E | Water (and) Sodium Hydroxide | qs |
| Part F | Fragrance | qs |

Manufacturing Instructions:

Part A and part B are heated separately up to 75° C., part C is heated to 60° C. Afterwards part B is poured into part A under stirring. The mixture is homogenized with an Ultra Turrax for 30 sec. at 11 000 rpm and part C is incorporated. After cooling down to 40° C. part D is added. At room temperature the pH-value is adjusted with Sodium Hydroxide between 6.30 and 6.70 and part F is added.

Example 23

Water Resistant Sunscreen Emulsion

| | INCI-Name | % w/w (as supplied) |
|---|---|---|
| Part A | Polyglyceryl-10 Pentastearate (and) Behenyl Alcohol (and) Sodium Stearoyl Lactylate | 2.50 |
| | VP/Eicosene Copolymer | 1.50 |
| | Stearyl Alcohol | 1.50 |
| | Squalane | 4.00 |
| | C12-15 Alkyl Benzoate | 5.50 |
| | Octocrylene | 1.50 |
| | 4-Methylbenzylidene Camphor | 3.00 |
| | Ethylhexyl Methoxycinnamate | 2.00 |
| | Ethyl hexyl salicylate (Neoheliopan OS) | 2.00 |
| Part B | Water | qs to 100 |
| | Glycerin | 1.80 |
| | Steareth-10 Allyl Ether/Acrylates Copolymer | 0.80 |
| Part C | UV-absorber dispersion as described in example 6 | 9.00 |

-continued

| | INCI-Name | % w/w (as supplied) |
|---|---|---|
| Part D | VP/Hexadecene Copolymer | 2.70 |
| | Cyclomethicone | 1.50 |
| | Phenoxyethanol (and) Methylparaben (and) Ethylparaben (and) Butylparaben (and) Propylparaben (and) Isobutylparaben | 0.70 |
| Part E | Aqua (and) Tocopheryl Acetate (and) Caprylic/Capric Triglyceride (and) Polysorbate 80 (and) Lecithin | 3.50 |
| Part F | Fragrance | qs |
| | Water (and) Sodium Hydroxide | qs |

Manufacturing Instructions:

Part A and part B are heated separately to 80° C. Part A is poured into part B under continuous stirring. Afterwards the mixture is homogenized with an Ultra Turrax at 11 000 rpm for 1 min. After cooling down to 60° C. part C is incorporated. At 40° C. part D is added and the mixture homogenized for a short time again. At 35° C. part E is added and at room temperature Fragrance is added. Finally the pH is adjusted with Sodium Hydroxide.

Example 24

UVA/UVB Sun Protection Lotion, O/W Type

| | INCI-Name | % w/w (as supplied) |
|---|---|---|
| Part A | Potassium Cetyl Phosphate | 2.00 |
| | Tricontanyl PVP | 1.00 |
| | Caprylic/Capric Triglyceride | 5.00 |
| | C12-15 Alkyl Benzoate | 5.00 |
| | Cetearyl Isononanoate | 5.00 |
| | Glyceryl Stearate | 3.00 |
| | Cetyl Alcohol | 1.00 |
| | Dimethicone | 0.10 |
| | Ethylhexyl Methoxycinnamate | 5.00 |
| Part B | Water | qs to 100 |
| | Glycerin | 3.00 |
| | 2,2'-bis(1,4-phenylene)-1H-benzimidazole-4,6-disulphonic acid mono sodium salt (Neoheliopan AP) | 2.00 |
| Part C | Steareth-10 Allyl Ether/Acrylates Copolymer | 0.50 |
| Part D | UV-absorber dispersion as described in example 6 | 8.00 |
| Part E | Phenoxyethanol (and) Methylparaben (and) Ethylparaben (and) Butylparaben (and) Propylparaben (and) Isobutylparaben | 1.00 |
| Part F | Water (and) Sodium Hydroxide | qs to pH 7.00 |
| Part G | Fragrance | qs |

Manufacturing Instructions:

Part A and part B are heated separately up to 80° C. Part B is poured into part A under moderate stirring. The mixture is homogenized with an Ultra Turrax at 11 000 rpm for 1 minute. After cooling down to 70° C. part C is added under stirring. After cooling further down to 50° C. part D is incorporated very slowly. At 40° C. part E is added. At room temperature the pH adjusted with part F to 7.00 and part G is added.

Example 25

UVA/UVB Sun Protection Lotion, O/W type

| | INCI-Name | % w/w (as supplied) |
|---|---|---|
| Part A | Potassium Cetyl Phosphate | 2.00 |
| | Tricontanyl PVP | 1.00 |
| | Caprylic/Capric Triglyceride | 5.00 |
| | C12-15 Alkyl Benzoate | 5.00 |
| | Cetearyl Isononanoate | 5.00 |
| | Glyceryl Stearate | 3.00 |
| | Cetyl Alcohol | 1.00 |
| | Dimethicone | 0.10 |
| | Ethylhexyl Methoxycinnamate | 4.00 |
| | Diethylhexyl butamido triazone (UVASORB HEB) | 1.00 |
| Part B | Water | qs to 100 |
| | Glycerin | 3.00 |
| Part C | Steareth-10 Allyl Ether/Acrylates Copolymer | 0.50 |
| Part D | UV-absorber dispersion as described in example 6 | 20.00 |
| Part E | Phenoxyethanol (and) Methylparaben (and) Ethylparaben (and) Butylparaben (and) Propylparaben (and) Isobutylparaben | 1.00 |
| Part F | Water (and) Sodium Hydroxide | qs to pH 7.00 |
| Part G | Fragrance | qs |

Manufacturing Instructions:

Part A and part B are heated separately up to 80° C. Part B is poured into part A under moderate stirring. The mixture is homogenized with an Ultra Turrax at 11000 rpm for 1 minute. After cooling down to 70° C. add part C is added under stirring. After cooling further down to 50° C. part D is incorporated very slowly. At 40° C. part E is added. At room temperature the pH is adjusted with part F to 7.00 and part G is added.

Example 26

Sunscreen Lotion

| | INCI-Name | % w/w (as supplied) |
|---|---|---|
| Part A | Cetearyl Alcohol (and) Dicetyl Phosphate (and) Ceteth-10 Phosphate | 4.00 |
| | C12-15 Alkyl Benzoate | 2.00 |
| | Dicaprylyl Ether | 3.00 |
| | Ethoxydiglycol Oleate | 2.00 |
| | Stearic Acid | 1.00 |
| | Ethylhexyl Methoxycinnamate | 2.00 |
| | Sodium Acrylates Copolymer (and) Glycine Soja (and) PPG-1 Trideceth-6 | 0.30 |
| | Squalane | 3.50 |
| | VP/Eicosene Copolymer | 2.00 |
| | Benzylidene malonate polysiloxane (Parsol SLX) | 2.00 |
| Part B | Water | qs to 100 |
| | UV-absorber dispersion as described in example 6 | 5.00 |
| Part C | Diazolidinyl Urea (and) Iodopropynyl Butylcarbamate | 0.15 |
| | Propylene Glycol | 2.50 |
| | Water | 10.00 |
| Part D | Cyclopentasiloxane (and) Dimethiconol | 2.00 |
| | Ethoxydiglycol | 5.00 |
| | Cyclopentasiloxane (and) Dimethicone/Vinyl Dimethicone Crosspolymer | 2.00 |
| Part E | Aqua (and) Sodium Hydroxide | qs |
| Part F | Fragrance | qs |

Manufacturing Instruction

Part A and part B are heated separately up to 75° C. Part B is poured into part A under progressive stirring speed. At a temperature <65° C. the ingredients of part D are added separately. After cooling down to 55° C. under moderate stirring part C is added. At a temperature <35° C. the pH is checked and adjusted with Sodium Hydroxide and homogenized with an Ultra Turrax for 30 sec. at 11 000 rpm. At room temperature part F is added.

Example 27

W/O Sunscreen Lotion

|  | INCI-Name | % w/w (as supplied) |
|---|---|---|
| Part A | PEG-7 Hydrogenated Castor Oil | 3.00 |
|  | Polyglyceryl-3 Diisostearate | 4.00 |
|  | Microcrystalline Wax | 1.00 |
|  | Magnesium Stearate | 1.50 |
|  | Propylparaben | 0.10 |
|  | Mineral Oil | 15.00 |
|  | Octyldodecanol | 8.00 |
|  | Ethylhexyl Triazone | 1.00 |
|  | Ethylhexyl Methoxycinnamate | 2.00 |
|  | Diethylamino Hydroxybenzoyl Hexyl Benzoate (Uvinul A+) | 1.50 |
| Part B | Water | qs to 100 |
|  | Water (and) Citric Acid | 0.05 |
|  | Methylparaben | 0.15 |
|  | Magnesium Sulfate | 0.50 |
| Part C | UV-absorber dispersion as described in example 6 | 9.00 |
|  | Fragrance | qs |

Manufacturing Instructions:

Part A is heated to 80° C. whilst stirring. Part B is added into part A and homogenized with an Ultra Turrax at 11 000 rpm for one minute. After cooling down to 30° C. part C is incorporated.

Example 28

Skin Protection Sunscreen Lotion W/O

|  | INCI-Name | % w/w (as supplied) |
|---|---|---|
| Part A | Polyglyceryl-2 Dipolyhydroxystearate | 3.00 |
|  | Glyceryl Oleate | 3.00 |
|  | Cetearyl Isononanoate | 7.00 |
|  | Hexyl Laurate | 6.00 |
|  | Dicaprylyl Ether | 6.00 |
|  | Propylparaben | 0.10 |
|  | Hexyldecanol | 3.00 |
|  | Magnesium Stearate | 1.00 |
|  | Beeswax | 1.00 |
|  | Ethylhexyl Methoxycinnamate | 4.00 |
| Part B | Water | qs to 100 |
|  | Methylparaben | 0.15 |
|  | Magnesium Sulfate | 1.00 |
| Part C | UV-absorber dispersion as described in example 6 | 6.00 |

Manufacturing Instructions:

Part A is heated separately to 80° C. under gentle stirring. Part B is added to part A and homogenized for one minute at 11000 rpm. After cooling down to 30° C. part C is added under continuous stirring.

Example 29

Sunscreen

|  | INCI-Name | % w/w (as supplied) |
|---|---|---|
| Part A | Hexyldecanol | 2.70 |
|  | Polyoxyethylen-2-stearylalkohol | 2.20 |
|  | PEG-30 Dipolyhydroxystearate | 1.10 |
| Disp. | UV-absorber as described in example 6; pH = 7 adjusted with citric acid | 6 |
| Part B | Cetyl Ethylhexanoate | 4.00 |
|  | Isohexadecane | 4.00 |
|  | Ethxlhexyl methoxy cinnamate | 0.00 |
|  | Bis-ethylhexyloxyphenol methoxyphenyl triazine (Tinosorb S) | 0.00 |
|  | Phenoxyethanol (and) Methylparaben (and) Ethylparaben (and) Butylparaben (and) Propylparaben (and) Isobutylparaben | 0.60 |
| Part C | Water | Qs. 100 |
|  | Glycerin | 3.00 |
| Part D | Sodium Acrylates Copolymer (and) Mineral Oil (and) PPG-1 Trideceth-6 | 2.00 |
| Part E | Cyclopentasiloxane | 2.00 |

This Sunscreen may also be used as an anti-wrinkle perception modifier.

Manufacturing Instruction

Mix part A and heat up to 60° C. to 65° C. and add Disp. Slowly under fast stirring Add part B under moderate stirring at 60° C.

Add part B into part A under stirring at 60° C.-75° C.

Add part C under stirring until homogenization (emulsification at fast stirring, may be with ultra turrax)

Add part D under moderate stirring (60° C.)

Finally add part E under stirring (60° C.) and cool down under moderate stirring Example 30

PEG-free Sunscreen

|  | INCI-Name | w/w (as supplied %) |
|---|---|---|
| Part A | Hexyldecanol | 2.30 |
|  | Polyglyceryl-3 Methylglucose Distearate | 1.40 |
|  | Polyglyceryl polyhydroxy stearate | 1.40 |
| Disp. | UV-absorber as described in example 6; pH = 7 adjusted with citric acid | 5.00 |
| Part B | Cetyl Ethylhexanoate | 3.00 |
|  | Isohexadecane | 3.00 |
|  | Ethylhexyl methoxy cinnamate | 3.00 |
|  | Bis-ethylhexyloxyphenol methoxyphenyl triazine (Tinosorb S) | 2.00 |
|  | Phenoxyethanol (and) Methylparaben (and) Ethylparaben (and) Butylparaben (and) Propylparaben (and) Isobutylparaben | 0.60 |
| Part C | Water | Qs 100 |
|  | Glycerin | 3.00 |
| Part D | Sodium Acrylates Copolymer (and) Mineral Oil (and) PPG-1 Trideceth-6 | 1.50 |
| Part E | Cyclopentasiloxane | 1.50 |

The invention claimed is:

1. A method for the protection of human and animal hair and skin against the damaging effect of UV radiation, which comprises applying an effective protecting amount to said hair or skin of at least one compound of formula

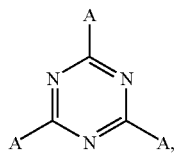
(1)

wherein
A is a radical of formula

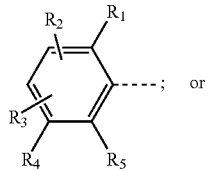
(1a)

or

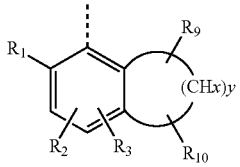
(1b)

$R_1$ and $R_5$ independently from each other are hydrogen; $C_1$-$C_{18}$alkyl; or $C_6$-$C_{12}$aryl;

$R_2$, $R_3$ and $R_4$ independently from each other are hydrogen; or a radical of formula

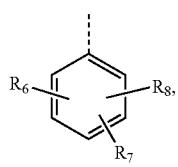
(1c)

wherein, in formula (1a), at least one of the radicals $R_2$, $R_3$ and $R_4$ are a radical of formula (1c);

$R_6$, $R_7$, $R_8$, $R_9$ and $R_{10}$ independently from each other are hydrogen; hydroxy; halogen; $C_1$-$C_{18}$alkyl; $C_1$-$C_{18}$alkoxy; $C_6$-$C_{12}$aryl; biphenylyl; $C_6$-$C_{12}$aryloxy; $C_1$-$C_{18}$alkylthio; carboxy; —COOM; $C_1$-$C_{18}$-alkylcarboxyl; aminocarbonyl; or mono- or di-$C_1$-$C_{18}$alkylamino; $C_1$-$C_{10}$acylamino; —COOH;

M is an alkali metal ion;

x is 1 or 2; and y is a number from 2 to 10.

2. A method according to claim 1, which relates to compounds of formula

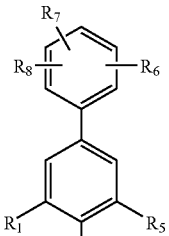
(2)

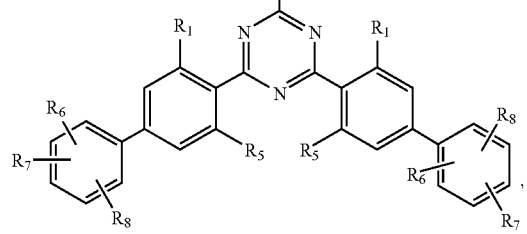

wherein
$R_1$, $R_5$, $R_6$, $R_7$ und $R_8$ are defined as in claim 1.

3. A method according to claim 1, wherein $R_1$ and $R_5$ are hydrogen.

4. A method according to claim 1, wherein $R_6$ and $R_8$ are hydrogen.

5. A method according to claim 1, wherein
$R_7$ is hydrogen; hydroxy; $C_1$-$C_5$alkyl; $C_1$-$C_5$alkoxy; —COOM; —COOH; or COOR$_{10}$;
M is an alkali metal ion; and
$R_{10}$ is $C_1$-$C_5$alkyl.

6. A method according to claim 1, which relates to compounds of formula

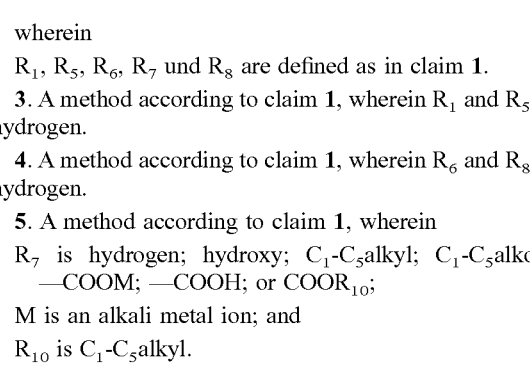
(3)

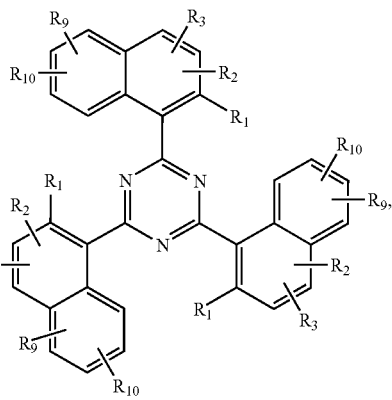

wherein
$R_1$, $R_2$, $R_3$, $R_9$ and $R_{10}$ are defined as in claim 1.

7. A method according to claim 6, wherein
$R_1$, $R_2$, $R_3$, $R_9$ and $R_{10}$ are hydrogen; or, independently from each other, $C_1$-$C_{18}$alkyl.

8. A method according to claim 1, wherein the compound of formula (6)

[structure: 2,4,6-tris(4-biphenylyl)-1,3,5-triazine]

is used.

9. A cosmetic preparation comprising at least one compound of formula (1) according to claim 1 together with cosmetically tolerable carriers or adjuvants.

10. Cosmetic preparation according to claim 9 comprising the UV filter combination (A) comprising
   ($a_1$) at least one symmetrical triazine derivative of formula (1) and
   ($a_2$) at least one aminobenzophenone derivative of formula $$\left[ \begin{array}{c} R_1 \\ \diagdown \\ N \\ \diagup \\ R_2 \end{array} \!\!- \!\!\!\! \underset{\displaystyle}{\text{Ar}}(OH)\text{—C(O)—Ar—C(O)—A} \!\!-\!\! R_3 \right]_{n_1}$$

wherein
   $R_1$ and $R_2$ independently from each other are; $C_1$-$C_{20}$alkyl; $C_2$-$C_{20}$alkenyl; $C_3$-$C_{10}$cycloalkyl; $C_3$-$C_{10}$cycloalkenyl; or $R_1$ and $R_2$ together with the linking nitrogen atom form a 5- or 6-membered heterocyclic ring;
   $n_1$ is a number from 1 to 4;
   when $n_1$=1,
   $R_3$ is a saturated or unsaturated heterocyclic radical; hydroxy-$C_1$-$C_5$alkyl; cyclohexyl optionally substituted with one or more $C_1$-$C_5$alkyl; phenyl optionally substituted with a heterocyclic radical, aminocarbonyl or $C_1$-$C_5$alkylcarboxy;
   when $n_1$ is 2,
   $R_3$ is an alkylene-, cycloalkylene, alkenylene or phenylene radical which is optionally substituted by a carbonyl- or carboxy group; a radical of formula *—$CH_2$—C≡C—$CH_2$—* or $R_3$ together with A forms a bivalent radical of the formula $$-\!\!\!\underset{(CH_2)_{n_2}}{\overset{(CH_2)_{n_2}}{\text{A}\diagup\!\!\!\diagdown\text{A}}}\!\!\!- ;$$ (1a)

wherein
   $n_2$ is a number from 1 to 3;
   when $n_1$ is 3,
   $R_3$ is an alkanetriyl radical;
   when $n_1$ is 4,
   $R_3$ is an alkanetetrayl radical;
   A is —O—; or —N($R_5$)—; and
   $R_5$ is hydrogen; $C_1$-$C_5$alkyl; or hydroxy-$C_1$-$C_5$alkyl.

11. Cosmetic preparation according to claim 10 comprising the UV filter combination (A1) comprising
   ($a_3$) the compound of formula (6) or (9)

(6)

[structure: 2,4,6-tris(4-biphenylyl)-1,3,5-triazine]

(9)

[structure: 2,4,6-tris(4-(4-biphenylyl)phenyl)-1,3,5-triazine / terphenyl-substituted triazine]

and ($a_4$) the compound of formula

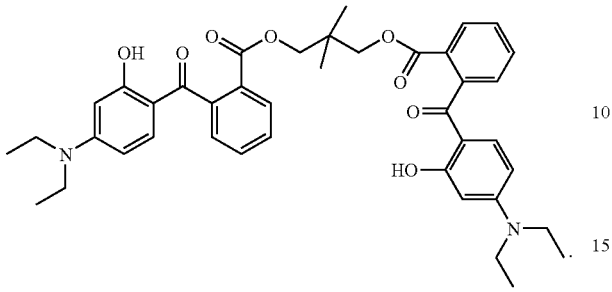

12. Cosmetic preparation according to claim 9 comprising the UV filter combination (B) comprising ($b_1$) at least one symmetrical triazine derivative of formula (1); and ($b_2$) at least one aminobenzophenone derivative of the formula

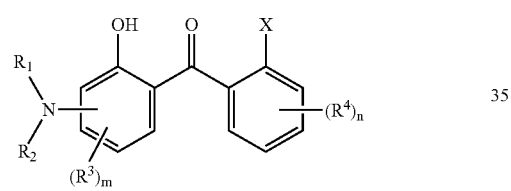

wherein $R^1$ and $R^2$ independently from each other are hydrogen, $C_1$-$C_{20}$alkyl; $C_2$-$C_{20}$alkenyl; $C_3$-$C_{10}$cycloalkenyl; wherein $R^1$ and $R^2$ may form a five- or six-membered ring;

$R^3$ and $R^4$ independently from each other are $C_1$-$C_{20}$alkyl; $C_2$-$C_{20}$alkenyl; $C_3$-$C_{10}$cycloalkenyl, $C_1$-$C_{20}$alkoxy, $C_1$-$C_{20}$alkoxycarbonyl, $C_1$-$C_{20}$alkylamino, di($C_1$-$C_{20}$alkyl)amino, optionally substituted aryl or heteroaryl;

X is hydrogen; $COOR^5$; $CONR^6R^7$;

$R^5$, $R^6$, $R^7$ independently from each other are hydrogen, $C_1$-$C_{20}$alkyl; $C_2$-$C_{20}$alkenyl; $C_3$-$C_{10}$cycloalkyl; $C_3$-$C_{10}$cycloalkenyl; (Y—O)$_q$-Z; optionally substituted aryl;

Y is —(CH$_2$)$_2$—; —(CH$_2$)$_3$—; —(CH$_2$)$_4$—; —CH(CH$_3$)—CH$_2$—;

Z is —CH$_2$—CH$_3$; —CH$_2$—CH$_2$—CH$_3$; —CH$_2$—CH$_2$—CH$_2$—CH$_3$; CH(CH$_3$)—CH$_3$;

M is 0; 1; 2; or 3;

n is 0; 1; 2; 3; or 4; and q is a number from 1 to 20.

13. Cosmetic preparation according to claim 12 comprising the UV filter combination (B1) comprising ($b_3$) the compound of formula (6) or (9)

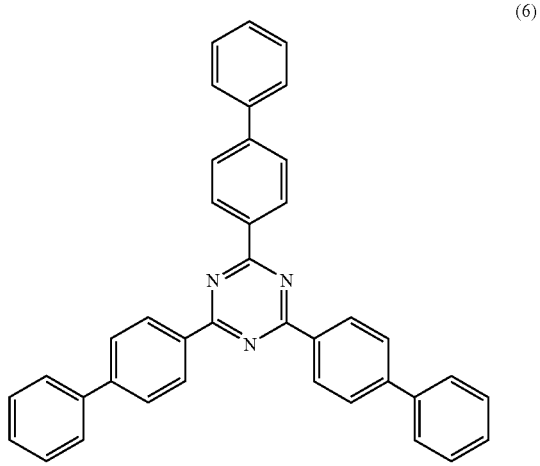

and ($b_4$) the compound of formula

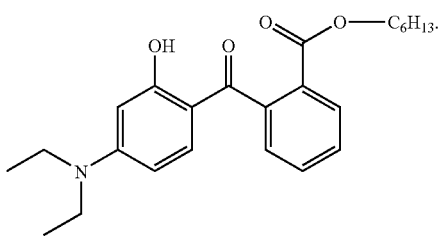

14. Cosmetic preparation according to claim 9 comprising the UV filter combination (C) comprising
- ($c_1$) at least one symmetrical triazine derivative of formula (1); and
- ($c_2$) at least one benzotriazole derivative of formula

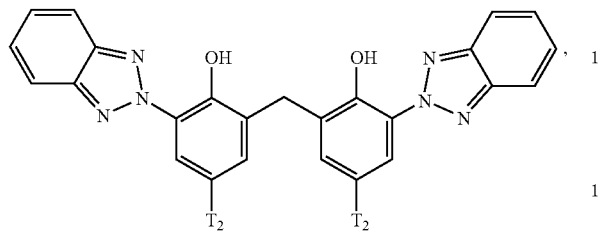

wherein
$T_2$ is $C_1$-$C_{10}$alkyl, or phenyl-substituted $C_1$-$C_4$alkyl.

15. Cosmetic preparation according to claim 14 comprising the UV filter combination (C1) comprising
- ($C_3$) the compound of formula (6) or (9)

(6)

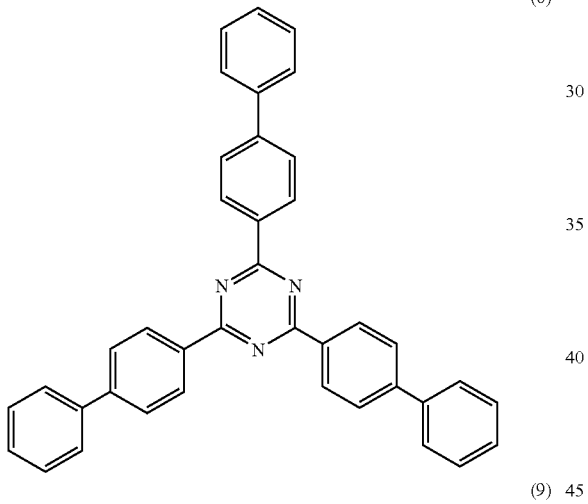

(9)

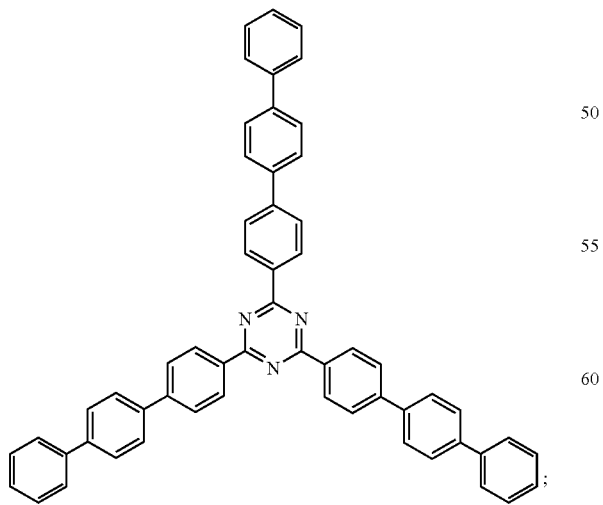

and ($c_4$) the compound of formula

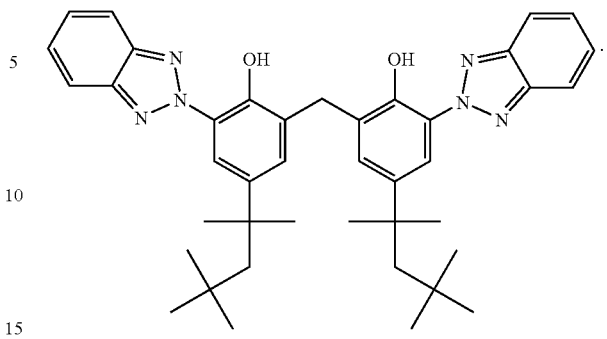

16. Cosmetic preparation according to claim 9 comprising the UV filter combination (D) comprising
- ($d_1$) at least one symmetrical triazine derivative of formula (1); and
- ($d_2$) at least one compound of formula

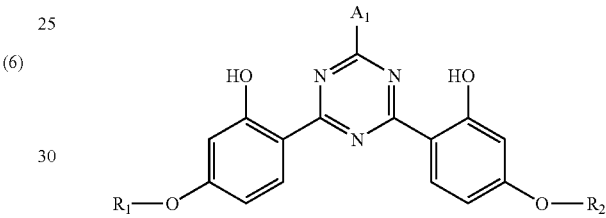

in which
$R_1$ and $R_2$, independently of one another, are $C_3$-$C_{18}$alkyl; $C_2$-$C_{18}$alkenyl; a radical of the formula —$CH_2$—CH(—OH)—$CH_2$—O-$T_1$; or
$R_1$ and $R_2$ are a radical of the formula (4a)

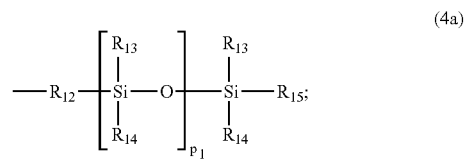

$R_{12}$ is a direct bond; a straight-chain or branched $C_1$-$C_4$alkylene radical or a radical of the formula —$C_{m_1}H_{2m_1}$— or —$C_{m_1}H_{2m_1}$—O—;
$R_{13}$, $R_{14}$ and $R_{15}$, independently of one another, are $C_1$-$C_{18}$alkyl; $C_1$-$C_{18}$alkoxy or a radical of the formula

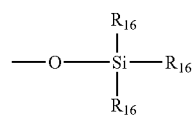

$R_{16}$ is $C_1$-$C_5$alkyl;
$m_1$ and $m_3$, independently of one another, are 1 to 4;
$p_1$ is 0 or a number from 1 to 5;

$A_1$ is a radical of the formula

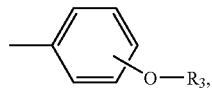 (1b)

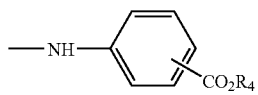 (1c)

or of the formula

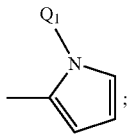 (1d)

$R_3$ is hydrogen; $C_1$-$C_{10}$alkyl, —$(CH_2CHR_5$—$O)_{n_1}$—$R_4$; or a radical of the formula —$CH_2$—$CH(-OH)$—$CH_2$—$O$-$T_1$;

$R_4$ is hydrogen; M; $C_1$-$C_5$alkyl; or a radical of the formula —$(CH_2)_{m_2}$—$O$-$T_1$;

$R_5$ is hydrogen; or methyl;

$T_1$ is hydrogen; or $C_1$-$C_8$alkyl;

$Q_1$ $C_1$-$C_{18}$alkyl;

M is a metal cation;

$m_2$ is 1 to 4; and $n_1$ is 1-16.

17. Cosmetic preparation according to claim 16 comprising the UV filter combination (D1) comprising ($d_3$) the compound of formula (6) or (9)

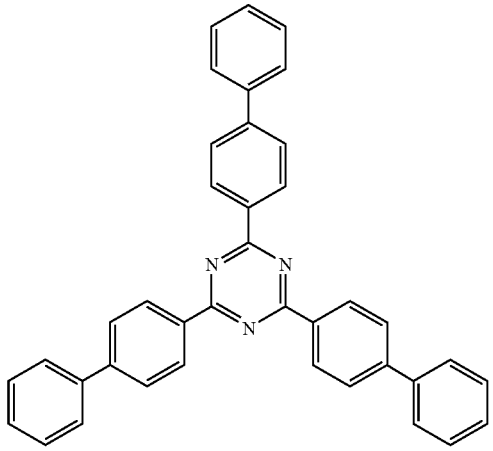 (6)

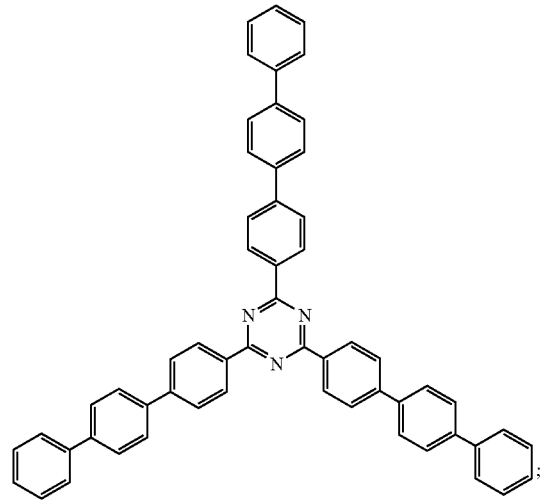 (9)

and ($d_4$) the compound of formula

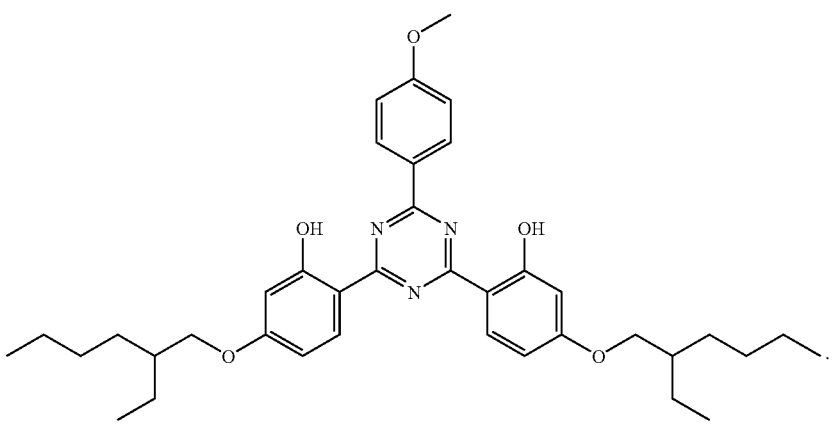

18. Cosmetic preparation according to claim 9 comprising the UV filter combination (E) comprising ($e_1$) at least one symmetrical triazine derivative of formula (1); and ($e_2$) at least one hydroxyphenyltriazine compound of formula

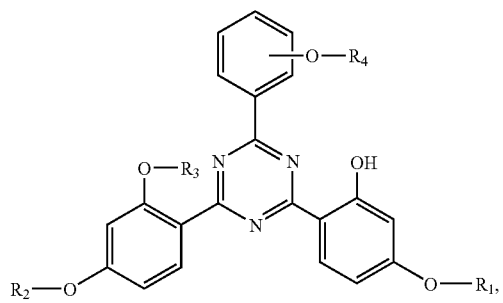

(1)

wherein $R_1$, $R_2$ and $R_3$ are each independently of the others $C_1$-$C_{18}$alkyl; $C_2$-$C_{10}$alkenyl; or phenyl-$C_1$-$C_4$alkyl; and $R_4$ is hydrogen; or $C_1$-$C_5$alkyl.

19. Cosmetic preparation according to claim 18 comprising the UV filter combination (E1) comprising ($d_3$) the compound of formula (6) or (9)

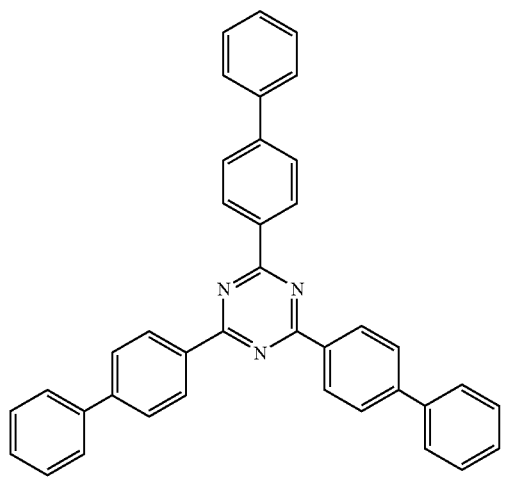

(6)

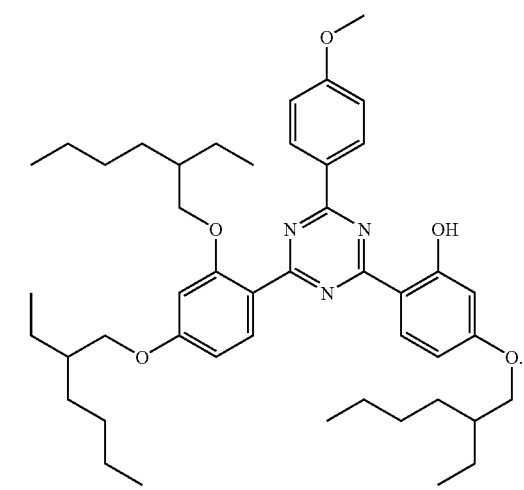

(9)

and ($d_4$) the compound of formula

20. Cosmetic preparation according to claim 9 comprising the UV filter combination (F) comprising ($f_1$) at least one symmetrical triazine derivative of formula (1); and ($f_2$) at least one dibenzoylmethane derivative of formula

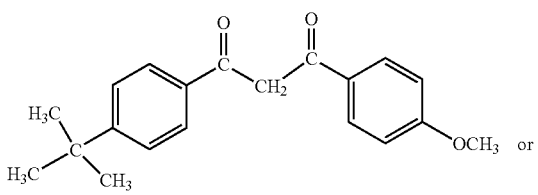

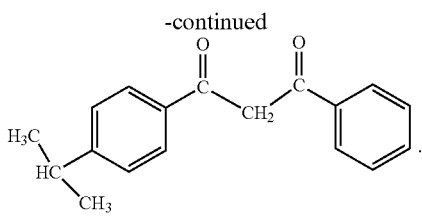

21. Cosmetic preparation according to claim 9 comprising the UV filter combination (G) comprising
- ($g_1$) at least one symmetrical triazine derivative of formula (1); and
- ($g_2$) disodium phenyl dibenzimidazole tetrasulfonate.

22. Cosmetic preparation according to claim 9 comprising the UV filter combination (H) comprising
- ($h_1$) at least one symmetrical triazine derivative of formula (1); and
- ($h_2$) at least one benzoxazole-substituted triazine of the formula

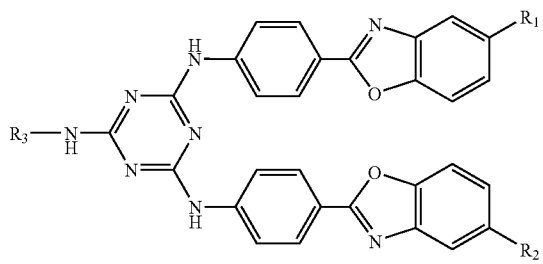

($h_21$)

wherein $R_1$, $R_2$ and $R_3$ independently from each other are branched or unbranched $C_1$-$C_{12}$alkyl.

23. Cosmetic preparation according to claim 22 comprising the UV filter combination (H1) comprising
- ($h_3$) the compound of formula (6) or (9)

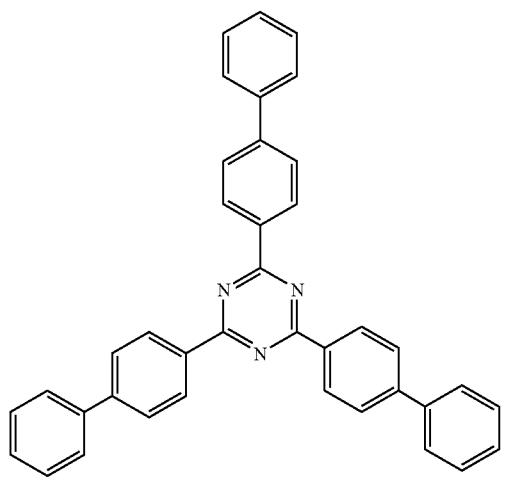

(6)

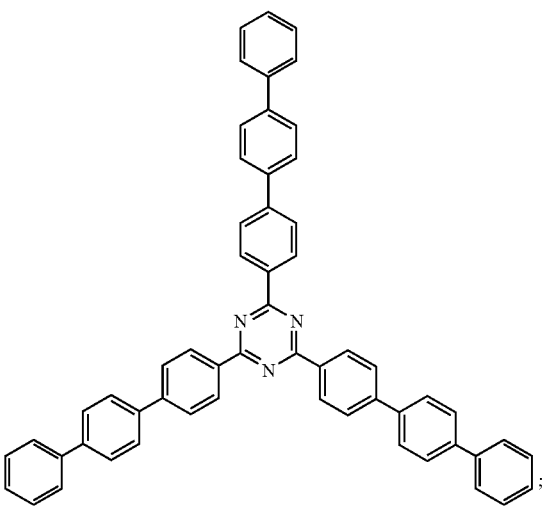

(9)

and
- ($h_4$) at least one compound of formula ($h_21$), wherein $R_1$ and $R_2$ independently from each other are tert. butyl; or tert. amyl; and
  $R_2$ is tert.butyl, tert.octyl; or 2-ethylhexyl.

24. Cosmetic preparation according to claim 23 comprising the UV filter combination (H2) comprising
- ($h_5$) the compound of formula (6) or (9); and
- ($h_6$) at least one compound of formula ($h_21$), wherein
  - ($h_{61}$) $R_1$ and $R_2$ are tert.amyl; and $R_3$ is tert.butyl; or wherein
  - ($h_{62}$) $R_1$ and $R_2$ are tert.butyl and $R_3$ is tert.octyl; or wherein
  - ($h_{63}$) $R_1$ and $R_2$ are tert.butyl; and $R_3$ is 2-ethylhexyl; or wherein
  - ($h_{64}$) $R_1$ and $R_2$ are tert.amyl; and $R_3$ is 2-ethylhexyl.

25. Cosmetic preparation according to claim 9 comprising the UV filter combination (I) comprising
- ($i_1$) at least one symmetrical triazine derivative of formula (1); and
- ($i_2$) 2-(2H-benzotriazol-2-yl)-4-methyl-6-[2-methyl-3-[1,3,3,3-tetramethyl-1-[(trimethylsily)oxy]-disiloxanyl]propyl]-.

26. Cosmetic preparation according to claim 9 comprising the UV filter combination (K) comprising
- ($k_1$) at least one symmetrical triazine derivative of formula (1); and
- ($k_2$) siloxanes and silicones, di-Me, 1-[[4-[3-ethoxy-2-(ethoxycarbonyl)-3-oxo-1-propenyl]phenoxy]-methyl]ethenyl Me, 3-[4-[3-ethoxy-2-(ethoxycarbonyl)-3-oxo-1-propenyl]phenoxy]-1-propenyl Me, Me hydrogen.

27. Cosmetic preparation according to claim 9 comprising the UV filter combination (L) comprising
- ($l_1$) at least one symmetrical triazine derivative of formula (1); and
- ($l_2$) (+/−)-1,7,7-trimethyl-3-[(4-methylphenyl)methylene]bicyclo[2.2.1]heptan-2-one.

28. Cosmetic preparation according to claim 9 comprising the UV filter combination (M) comprising
- ($m_1$) at least one symmetrical triazine derivative of formula (1); and
- ($m_2$) α-(2-oxoborn-3-ylidene)toluene-4-sulphonic acid and its salts.

29. Cosmetic preparation according to claim 9 comprising the UV filter combination (N) comprising
($n_1$) at least one symmetrical triazine derivative of formula (1); and
($n_2$) methyl N,N,N-trimethyl-4-[(4,7,7-trimethyl-3-oxobicyclo[2,2,1]hept-2-ylidene)methyl]anilinium sulphate.

30. Cosmetic preparation according to claim 9 comprising the UV filter combination (O) comprising
($o_1$) at least one symmetrical triazine derivative of formula (1); and
($o_2$) 2-ethylhexyl 2-cyano,3,3-diphenylacrylate.

31. Cosmetic preparation according to claim 9 comprising the UV filter combination (P) comprising
($p_1$) at least one symmetrical triazine derivative of formula (1); and
($p_2$) 2-ethylhexyl 4-methoxycinnamate.

32. Cosmetic preparation according to claim 9 comprising the UV filter combination (Q) comprising
($q_1$) at least one symmetrical triazine derivatives derivative of formula (1); and
($q_2$) benzoic acid, 4,4',4''-(1,3,5-triazine-2,4,6-triyltriimino)tris-,tris(2-ethylhexyl)ester; 2,4,6-Trianilino-(p-carbo-2'-ethylhexyl-1'-oxi)-1,3,5-triazine.

33. Cosmetic preparation according to claim 9 comprising the UV filter combination (R) comprising
($r_1$) at least one symmetrical triazine derivative of formula (1); and
($r_2$) 2-phenyl-1H-benzimidazole-5-sulphonic acid.

34. Cosmetic preparation according to claim 9 comprising the UV filter combination (S) comprising
($s_1$) at least one symmetrical triazine derivative of formula (1); and
($s_2$) Benzoic acid,4,4'-[[6-[[4-[[(1,1-dimethylethyl)amino]carbonyl]phenyl]amino]1,3,5-triazine-2,4-diyl]diimino]bis-,bis(2-ethylhexyl)ester.

35. Cosmetic composition according claim 9 wherein the compound of formula (1), formula (6) or formula (9)

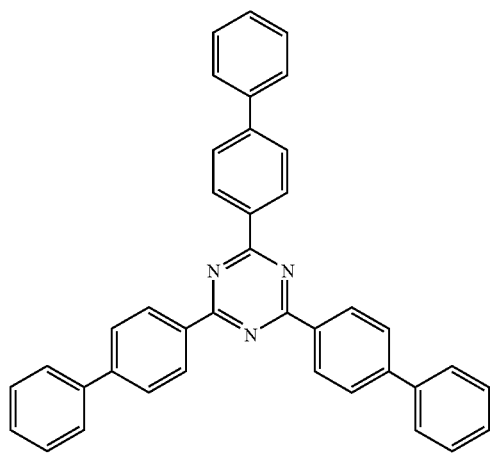

(6)

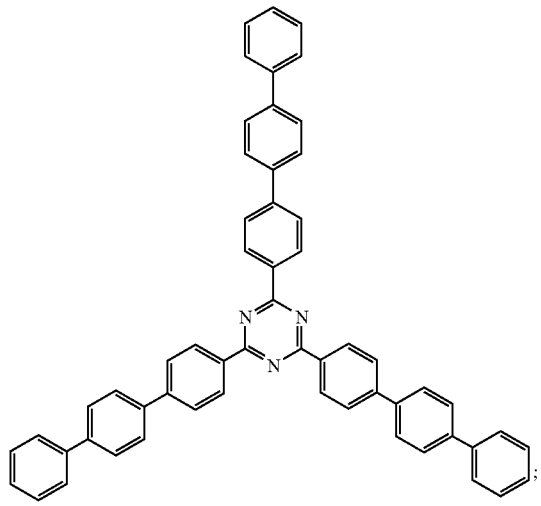

(9)

is present in the composition in the micronized state.

36. A method of reducing the perception of wrinkles on human skin, which comprises applying an effective amount of at least one compound of formula (1) according to claim 1 to said skin as an anti-wrinkle perception modifier.

37. A process for the preparation of the compound of formula (1) according to claim 1, comprising reacting a halogen triazine compound of formula (1d) in a Friedel-Crafts-reaction with an optionally substituted aromatic hydrocarbon of formula (1e) or (1f) to the compound of formula (1) according to the following reaction scheme:

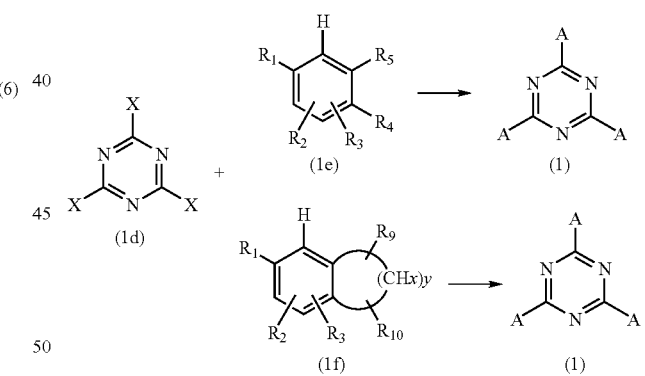

wherein
X is fluoro; chloro; or bromo; and
$R_1$, $R_2$, $R_3$, $R_9$, $R_{10}$, x and y are defined as in claim 1.

* * * * *

UNITED STATES PATENT AND TRADEMARK OFFICE
CERTIFICATE OF CORRECTION

PATENT NO. : 7,311,897 B2  Page 1 of 1
APPLICATION NO. : 10/804676
DATED : December 25, 2007
INVENTOR(S) : Thomas Ehlis et al.

It is certified that error appears in the above-identified patent and that said Letters Patent is hereby corrected as shown below:

On the title page Item (30) should read:

-- (30)     Foreign Application Priority Data
   Mar. 24, 2003    (EP)            03100758
   Jul. 29, 2003    (EP)            03102325 --.

Signed and Sealed this

Twenty-ninth Day of April, 2008

JON W. DUDAS
*Director of the United States Patent and Trademark Office*